(12) United States Patent
Pevarello et al.

(10) Patent No.: US 9,718,812 B2
(45) Date of Patent: Aug. 1, 2017

(54) SUBSTITUTED THIAZOLE OR OXAZOLE P2X7 RECEPTOR ANTAGONISTS

(71) Applicant: Axxam S.P.A., Bresso (IT)

(72) Inventors: Paolo Pevarello, Bresso (IT); Stefan Lohmer, Bresso (IT); Chiara Llberati, Bresso (IT); Pierfausto Seneci, Milan (IT); Cristina Pesenti, Milan (IT); Adolfo Prandi, Milan (IT)

(73) Assignee: Axxam S.P.A., Bresso (MI) (IT)

( * ) Notice: Subject to any disclaimer, the term of this patent is extended or adjusted under 35 U.S.C. 154(b) by 0 days.

(21) Appl. No.: 15/115,963

(22) PCT Filed: Feb. 4, 2015

(86) PCT No.: PCT/EP2015/052316
§ 371 (c)(1),
(2) Date: Aug. 2, 2016

(87) PCT Pub. No.: WO2015/118019
PCT Pub. Date: Aug. 13, 2015

(65) Prior Publication Data
US 2017/0008883 A1    Jan. 12, 2017

(30) Foreign Application Priority Data

Feb. 5, 2014 (EP) .................................. 14154038

(51) Int. Cl.
| | |
|---|---|
| C07D 417/06 | (2006.01) |
| C07D 413/14 | (2006.01) |
| C07D 277/30 | (2006.01) |
| C07D 417/14 | (2006.01) |
| C07F 7/18 | (2006.01) |
| C07D 277/28 | (2006.01) |
| C07D 263/32 | (2006.01) |
| C07D 413/06 | (2006.01) |

(52) U.S. Cl.
CPC ......... *C07D 417/06* (2013.01); *C07D 263/32* (2013.01); *C07D 277/28* (2013.01); *C07D 277/30* (2013.01); *C07D 413/06* (2013.01); *C07D 413/14* (2013.01); *C07D 417/14* (2013.01); *C07F 7/18* (2013.01)

(58) Field of Classification Search
CPC ........................... C07D 417/06; C07D 413/14
See application file for complete search history.

(56) References Cited

FOREIGN PATENT DOCUMENTS

| WO | 2004099146 A1 | 11/2004 |
|---|---|---|
| WO | 2008055840 A1 | 5/2008 |
| WO | 2009058299 A1 | 5/2009 |
| WO | 2009108551 A2 | 9/2009 |
| WO | 2009110985 A2 | 9/2009 |
| WO | 2009132000 A1 | 10/2009 |
| WO | 2010051188 A1 | 5/2010 |
| WO | 2010111058 A1 | 9/2010 |
| WO | 2010111059 A1 | 9/2010 |
| WO | 2010111060 A1 | 9/2010 |
| WO | 2014091415 A1 | 6/2014 |

OTHER PUBLICATIONS

Search Report and Written Opinion of PCT/EP2015/052316 of Mar. 31, 2015.

*Primary Examiner* — Golam M M Shameem
(74) *Attorney, Agent, or Firm* — Silvia Salvadori, P.C.; Silvia Salvadori

(57) ABSTRACT

The present invention refers to novel substituted thiazole and oxazole compounds of formula (I) having P2X7 receptor (P2X7) antagonistic properties. The compounds are useful in the treatment or prophylaxis of diseases associated with P2X7 receptor activity in animals, in particular humans.

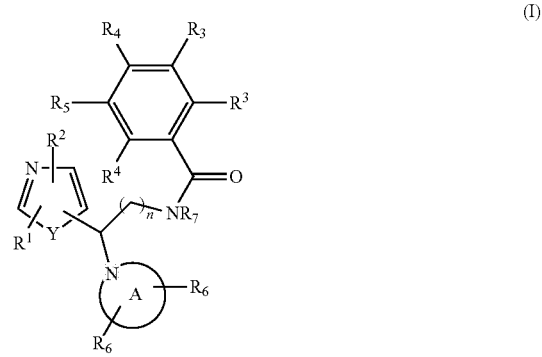

(I)

8 Claims, 1 Drawing Sheet

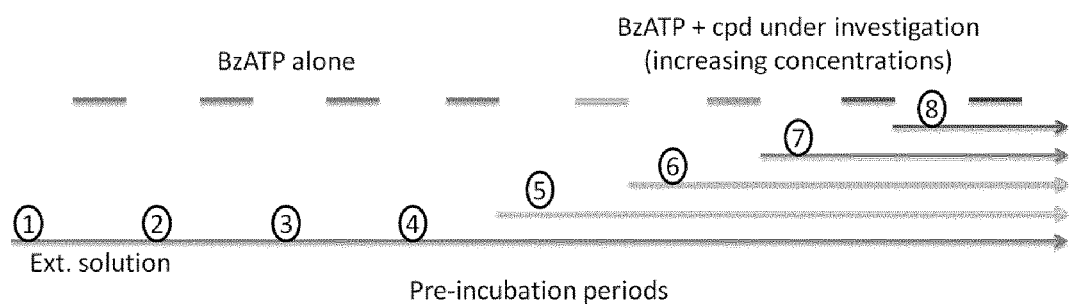

SUBSTITUTED THIAZOLE OR OXAZOLE P2X7 RECEPTOR ANTAGONISTS

This application is a U.S. national stage of PCT/EP2015/052316 filed on 4 Feb. 2015, which claims priority to and the benefit of European Application No. 14154038.5 filed on 5 Feb. 2014, the contents of which are incorporated herin by reference in their entireties.

The present invention is related to novel substituted thiazole and oxazole compounds of formula (I) having P2X7 receptor (P2X7) antagonistic properties, pharmaceutical compositions comprising these compounds, chemical processes for preparing these compounds and their use in the treatment or prophylaxis of diseases associated with P2X7 receptor activity in animals, in particular humans.

P2X7 belongs to the family of P2X ionotropic receptors. P2X7 is activated by extracellular nucleotides, notably adenosine triphosphate (ATP). P2X7 is distinguished from other P2X family members by the specific localization (CNS and immunocompetent cells in particular), by the high concentrations of ATP (in the mM range) required to activate it and by its ability to form a large pore upon prolonged or repeated stimulation. P2X7 is a ligand-gated ion channel and is present on a variety of cell types, largely those known to be involved in the inflammatory and/or immune process, specifically, macrophages, mast cells and lymphocytes (T and B). Activation of the P2X7 receptor by extracellular nucleotides, e.g., ATP, leads to the release of interleukin-1β (1Λ-1β) and giant cell formation (macrophages/microglial cells), degranulation (mast cells) and L-selectin shedding (lymphocytes). P2X7 receptors are also located on antigen-presenting cells (APC), keratinocytes, salivary acinar cells (parotid cells), hepatocytes, erythrocytes, erythroleukaemic cells, monocytes, fibroblasts, bone marrow cells, neurones, and renal mesangial cells. The P2X7 receptor is also known to be a pain sensor in the nervous system. Experiments using P2X7 deficient mice demonstrated the role of P2X7 in the development of pain as these mice were protected from the development of both adjuvant-induced inflammatory pain and partial nerve ligation induced neuropathic pain. There is also growing evidence that P2X7 or its downstream effectors, such as IL-1β, are involved in the pathophysiology of several neurological disorders, such as, Alzheimer's Disease (J. I. Diaz-Hernandez et al., Neurobiol. Aging 2012, 1816-1828: In vivo P2X7 inhibition reduces Aβ plaques in AD through GSK3β). P2X7 is thought to have an important function in neurotransmission within the CNS through its activation on postsynaptic and/or presynaptic neurons and glia. Data has emerged using in situ hybridization that P2X7 receptor mRNA is widely distributed throughout the rat brain. Specifically, areas of high P2X7 mRNA expression were found in the anterior olfactory nucleus, cerebral cortex, piriform cortex (Pir), lateral septal nucleus (LS), hippocampal pyramidal cell layers of CA1, CA3, CA4, pontine nuclei, external cuneate nucleus, and medial vestibular nucleus. P2X7 hybridization signals were also observed in the motor neurons of the trigeminal motor nucleus, facial nucleus, hypoglossal nucleus, and the anterior horn of the spinal cord.

Hence there is a therapeutic rationale for the use of P2X7 antagonists in the treatment of a variety of disease states. These states include but are not limited to diseases associated with the CNS such as Alzheimer's Disease, Parkinson's Disease, Huntington's Disease, Amyotrophic Lateral Sclerosis, spinal cord injury, cerebral ischemia, head trauma, meningitis, sleep disorders, mood and anxiety disorders, epilepsy, HIV-induced neuroinflammation and CNS damage, and chronic neuropathic and inflammatory pain. Furthermore, peripheral inflammatory disorders and autoimmune diseases including but not limited to rheumatoid arthritis, ostheoarthritis, psoriasis, allergic dermatitis, asthma, chronic obstructive pulmonary disease, airways hyper-responsiveness, septic shock, bronchitis, glomerulonephritis, irritable bowel syndrome, fatty liver disease, liver fibrosis, skin injury, lung emphysema, muscular dystrophy, fibrosis, atherosclerosis, burn injury, Crohn's Disease, ulcerative colitis, age-related macular degeneration, growth and metastasis of malignant cells, Sjogren's syndrome, myoblastic leukaemia, diabetes, osteoporosis, ischemic heart disease are all examples where the involvement of P2X7 receptors has been implicated. In view of the clinical importance of P2X7, the identification of compounds that modulate P2X7 receptor function represents an attractive avenue into the development of new therapeutic agents.

P2X7 inhibitors are described in in various patent applications such as:

WO2004/099146 that discloses benzamide inhibitors of the P2X7 receptor and their use in the treatment of inflammatory diseases.

WO2009/108551 that discloses heteroarylamide analogs and their use in P2X7 receptor mediated conditions.

WO2009/132000 that discloses quinoline and isoquinoline substituted P2X7 receptor antagonists and their use in P2X7 receptor mediated conditions.

However there is still an unmet need for compounds which are able to efficiently antagonize P2X7 and that can be delivered in the different target organs which are sites of a P2X7 mediated pathology, including the brain. Such compounds are provided herein.

BRIEF DESCRIPTION OF THE DRAWINGS

The FIG. shows the pre-incubation periods 5 to 8 contain increasing concentrations of the compound of interest.

Various embodiments of the invention are presented hereafter;

The present invention relates to thiazole or oxazole compounds of the following formula (I) or a pharmaceutically acceptable salt thereof:

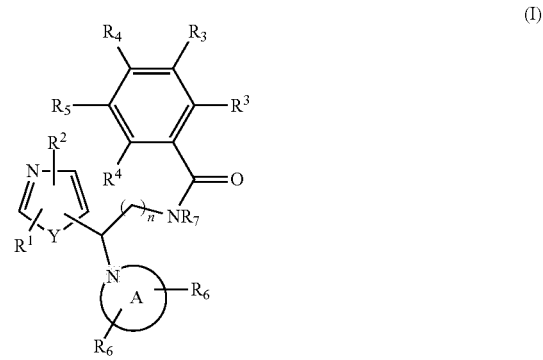

including any stereochemically isomeric form thereof, wherein n is 1 or 2;

Y represents oxygen or sulfur;

each of $R^1$ and $R^2$ is independently selected from the group consisting of hydrogen, deuterium, halogen, C1-C4 alkyl (optionally substituted with hydroxy or halogen, such as hydroxymethyl, fluoromethyl, difluoromethyl, trifluoromethyl), C3-C6 cycloalkyl (optionally substituted with hydroxy or halogen), or C1-C4 alkyloxy, each of $R^3$ and $R^4$ is independently selected from the group consisting of hydrogen, halogen, C1-C4 alkyl, difluoromethyl, trifluoromethyl, C1-C4 alkyloxy, $NR^9R^{10}$, wherein $R^9$ and $R^{10}$ independently are hydrogen or C1-C4 alkyl, or 2-thiazolidin-1,1-dione; or the two $R^3$ groups or the $R^3$ and $R^4$ groups taken together form a six membered heterocyclic ring containing a nitrogen atom;

$R^5$ is selected from hydrogen, halogen, or is an heterocyclic ring selected from pyrimidin-2-yl, pyridin-2-yl or pyrazin-2-yl, optionally substituted with halogen, C1-C4 alkyl, fluoromethyl, difluoromethyl, trifluoromethyl or C1-C4 alkyloxy;

$R^7$ is hydrogen or C1-C4 alkyl, preferably methyl; and ethyl;

the radical

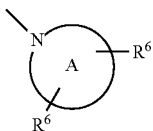

represents an optionally substituted azetidine, pyrrolidine, piperidine, morpholine, oxazepane, or 1,2,3,4-tetrahydroisoquinoline ring, wherein each of $R^6$ is independently selected from the group consisting of hydrogen, halogen, C1-C4 alkyl, C3-C6 cycloalkyl, C3-C6 spirocycloalkyl, difluoromethyl, trifluoromethyl, C1-C4 alkyloxy, aryl, hetaryl, C1-C4 aryloxy or C1-C4 arylalkoxy, wherein the aryl or hetaryl group is optionally substituted with halogen, C1-C4 alkyl, fluoromethyl, difluoromethyl, trifluoromethyl or C1-C4 alkyloxy;

The two groups R6 may be bound to the same carbon atom.

As used in the foregoing definitions:

The terms "halo", "halogen" and "halide", which may be used interchangeably, refer to a substituent fluoro, chloro, bromo, or iodo.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration.

Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, trifluoromethanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

A preferred embodiment of the invention relates to compounds of Formula (I) as defined above wherein Y and $R^1$-$R^6$ are as defined above, $R^7$ is hydrogen and n is 1.

Another embodiment of the invention relates to compounds of Formula (I) as defined above wherein n, Y and $R^3$-$R^7$ are as defined above, and both $R^1$ and $R^2$ are hydrogen or one is hydrogen and the other is methyl, ethyl, propyl, tert-butyl, optionally substituted with hydroxy or fluorine, C3-C6 cycloalkyl, optionally substituted with hydroxy or fluorine.

Another embodiment of the invention relates compounds of Formula (I) as defined above wherein n, Y and $R^1$, $R^2$, $R^6$ are as defined above, $R^5$ is hydrogen, $R^7$ is hydrogen, and each of $R^3$ and $R^4$ independently is hydrogen, halogen, preferably Cl or F, C1-C4 alkyl, preferably methyl, C1-C4 alkyloxy, preferably methoxy, $NR^9R^{10}$, wherein $R^9$ and $R^{10}$ independently are hydrogen or C1-C4 alkyl, or 2-thiazolidin-1,1-dione or the two $R^3$ groups taken together form a six membered heterocyclic ring containing a nitrogen atom.

Another embodiment of the invention relates compounds of Formula (I) as defined above wherein n, Y and $R^1$, $R^2$, $R^6$ are as defined above, $R^7$ is hydrogen, $R^4$ is hydrogen, the $R^3$ in meta position is hydrogen and the $R^3$ in ortho position is selected from the group consisting of halogen, preferably Cl or F, or C1-C4 alkyl, preferably methyl and $R^5$ is an heterocyclic ring selected from pyrimidin-2-yl, pyridin-2-yl or pyrazin-2-yl, optionally substituted with halogen, preferably pyrimidin-2-yl optionally substituted with fluoro;

Another embodiment of the invention relates compounds of Formula (I) as defined above wherein n, Y and $R^1$-$R^5$, are as defined above, $R^7$ is hydrogen, and the ring A is selected from the group consisting of

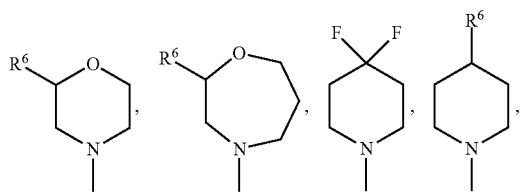

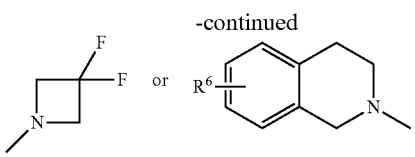

wherein R⁶ is hydrogen, halogen, benzyloxy or phenoxy, phenyl, pyrazole, C3-C6 cycloalkyl, optionally substituted with halogen, preferably substituted with fluoro.

Most preferably, a compound of formula 1 according to this invention is selected from the group consisting of:

| Compound | IUPAC NAME |
|---|---|
| 1 | 2-chloro-N-[2-(3,4-dihydro-1H-isoquinolin-2-yl)-2-(1,3-thiazol-2-yl)-ethyl]-6-fluoro-benzamide |
| 2 | 2-chloro-N-[2-(4,4-difluoro-piperidin-1-yl)-2-(1,3-thiazol-2-yl)-ethyl]-6-fluoro-benzamide |
| 3 | 2-chloro-6-fluoro-N-[2-(morpholin-4-yl)-2-(1,3-thiazol-2-yl)ethyl]benzamide |
| 4 | 2-chloro-N-[2-(4,4-difluoropiperidin-1-yl)-2-(1,3-thiazol-4-yl)ethyl]-6-fluorobenzamide |
| 5 | 2-chloro-6-fluoro-N-[2-(morpholin-4-yl)-2-(1,3-thiazol-4-yl)ethyl]benzamide |
| 6 | 2-chloro-N-[2-(3,4-dihydro-1H-isoquinolin-2-yl)-2-(1,3-thiazol-4-yl)-ethyl]-6-fluoro-benzamide |
| 7 | 2-chloro-6-fluoro-N-[2-(4-methyl-1,3-thiazol-5-yl)-2-(1,4-oxazepan-4-yl)ethyl]benzamide; 2-hydroxy-2-oxo-acetate |
| 8 | 2-chloro-N-[2-(4,4-difluoro-piperidin-1-yl)-2-(1,3-thiazol-5-yl)ethyl]-6-fluoro-benzamide |
| 9 | 2-chloro-N-[2-(3,4-dihydro-1H-isoquinolin-2-yl)-2-(1,3-thiazol-5-yl)-ethyl]-6-fluoro-benzamide |
| 10 | 2-chloro-6-fluoro-N(2-(morpholin-4-yl)-2-(thiazol-5-yl)-ethyl)benzamide |
| 11 | 2,6-dimethyl-N-[2-(morpholin-4-yl)-2-(1,3-thiazol-5-yl)ethyl]benzamide |
| 12 | 5-amino-2-chloro-N-[2-(morpholin-4-yl)-2-(1,3-thiazol-5-yl)ethyl]benzamide- |
| 13 | 2-chloro-6-methyl-N-[2-(morpholin-4-yl)-2-(1,3-thiazol-5-yl)ethyl]benzamide |
| 14 | N-[2-(4,4-difluoropiperidin-1-yl)-2-(1,3-thiazol-5-yl)ethyl]-2,6-dimethylbenzamide |
| 15 | 2-chloro-N-[2-(4,4-difluoropiperidin-1-yl)-2-(1,3-thiazol-5-yl)ethyl]-6-methylbenzamide |
| 16 | 5-amino-2-chloro-N-[2-(4,4-difluoropiperidin-1-yl)-2-(1,3-thiazol-5-yl)ethyl]benzamide |
| 17 | 5-amino-2-chloro-N-[2-(1,2,3,4-tetrahydroisoquinolin-2-yl)-2-(1,3-thiazol-5-yl)ethyl]benzamide |
| 18 | 2,6-dimethyl-N-[2-(1,2,3,4-tetrahydroisoquinolin-2-yl)-2-(1,3-thiazol-5-yl)ethyl]benzamide |
| 19 | 2-chloro-6-methyl-N-[2-(1,2,3,4-tetrahydroisoquinolin-2-yl)-2-(1,3-thiazol-5-yl)ethyl]benzamide |
| 20 | 2-chloro-N-[2-(4,4-difluoropiperidin-1-yl)-2-(1,3-thiazol-5-yl)ethyl]-5-(5-fluoropyrimidin-2-yl)-benzamide |
| 21 | N-[2-(4,4-difluoropiperidin-1-yl)-2-(1,3-thiazol-5-yl)ethyl]-2,3-dimethoxybenzamide |
| 22 | N-[2-(4,4-difluoropiperidin-1-yl)-2-(1,3-thiazol-5-yl)ethyl]-2,6-difluorobenzamide |
| 23 | N-{2-[4-(benzyloxy)piperidin-1-yl]-2-(1,3-thiazol-5-yl)ethyl}-2,6-dimethylbenzamide |
| 24 | N-{2-[4-(benzyloxy)piperidin-1-yl]-2-(1,3-thiazol-5-yl)ethyl}-2-chloro-6-methylbenzamide |
| 25 | N-{2-[4-(benzyloxy)piperidin-1-yl]-2-(1,3-thiazol-5-yl)ethyl}-2-chloro-6-fluorobenzamide |
| 26 | 2,6-dimethyl-N-[2-(4-phenoxypiperidin-1-yl)-2-(1,3-thiazol-5-yl)ethyl]benzamide |
| 27 | 2-chloro-6-fluoro-N-[2-(4-phenoxypiperidin-1-yl)-2-(1,3-thiazol-5-yl)ethyl]benzamide |
| 28 | 2-chloro-6-fluoro-N-[2-(piperidin-1-yl)-2-(1,3-thiazol-5-yl)ethyl]benzamide |
| 29 | 2-chloro-6-fluoro-N-[2-(4-methyl-1,3-thiazol-5-yl)-2-(1,2,3,4-tetrahydroisoquinolin-2-yl)ethyl]benzamide |
| 30 | 2,6-dimethyl-N-[2-(4-methyl-1,3-thiazol-5-yl)-2-(1,2,3,4-tetrahydroisoquinolin-2-yl)ethyl]benzamide |
| 31 | 2-chloro-N-[2-(4,4-difluoropiperidin-1-yl)-2-(4-methyl-1,3-thiazol-5-yl)ethyl]-6-fluorobenzamide |
| 32 | N-[2-(4,4-difluoropiperidin-1-yl)-2-(4-methyl-1,3-thiazol-5-yl)ethyl]-2,6-dimethylbenzamide |
| 33 | N-[2-(4,4-difluoropiperidin-1-yl)-2-(4-methyl-1,3-thiazol-5-yl)ethyl]quinoline-5-carboxamide |
| 34 | 2-chloro-N-[2-(4,4-difluoropiperidin-1-yl)-2-(4-methyl-1,3-thiazol-5-yl)ethyl]-5-(5-fluoropyrimidin-2-yl)benzamide |
| 35 | 2-chloro-6-fluoro-N-[2-(4-methyl-1,3-thiazol-5-yl)-2-(morpholin-4-yl)ethyl]benzamide |
| 36 | 2,6-dimethyl-N-[2-(4-methyl-1,3-thiazol-5-yl)-2-(morpholin-4-yl)ethyl]benzamide |
| 37 | 2-chloro-5-(5-fluoropyrimidin-2-yl)-N-[2-(4-methyl-1,3-thiazol-5-yl)-2-(morpholin-4-yl)ethyl]benzamide |
| 38 | 2-chloro-N-[2-(4,4-difluoropiperidin-1-yl)-2-(2-methyl-1,3-thiazol-5-yl)ethyl]-6-fluorobenzamide |
| 39 | 2-chloro-N-[2-(4,4-difluoropiperidin-1-yl)-2-(2-methyl-1,3-thiazol-5-yl)ethyl]-6-methylbenzamide |
| 40 | N-[2-(4,4-difluoropiperidin-1-yl)-2-(2-methyl-1,3-thiazol-5-yl)ethyl]-2,6-dimethylbenzamide |
| 41 | 2-chloro-6-methyl-N-[2-(2-methyl-1,3-thiazol-5-yl)-2-(1,2,3,4-tetrahydroisoquinolin-2-yl)ethyl]benzamide |
| 42 | 2,6-dimethyl-N-[2-(2-methyl-1,3-thiazol-5-yl)-2-(1,2,3,4-tetrahydroisoquinolin-2-yl)ethyl]benzamide |
| 43 | 2-chloro-6-fluoro-N-[2-(2-methyl-1,3-thiazol-5-yl)-2-(1,2,3,4-tetrahydroisoquinolin-2-yl)ethyl]benzamide |
| 44 | 2-chloro-6-fluoro-N-[2-(morpholin-4-yl)-2-(1,3-oxazol-5-yl)ethyl]benzamide |
| 45 | 2-chloro-N-[2-(4,4-difluoropiperidin-1-yl)-2-(1,3-oxazol-5-yl)ethyl]-6-fluorobenzamide |
| 46 | N-[2-(4,4-difluoropiperidin-1-yl)-2-(1,3-oxazol-5-yl)ethyl]-2,6-dimethylbenzamide |
| 47 | 2-chloro-N-[2-(4,4-difluoropiperidin-1-yl)-2-(1,3-oxazol-5-yl)ethyl]-5-(5-fluoropyrimidin-2-yl)benzamide |
| 48 | 2-chloro-6-fluoro-N-[2-(1,3-oxazol-5-yl)-2-(1,2,3,4-tetrahydroisoquinolin-2-yl)ethyl]benzamide |
| 49 | 2,6-dimethyl-N-[2-(1,3-oxazol-5-yl)-2-(1,2,3,4-tetrahydroisoquinolin-2-yl)ethyl]benzamide |
| 50 | N-[2-(4,4-difluoropiperidin-1-yl)-2-(4-methyl-1,3-oxazol-5-yl)ethyl]-2,3-dimethoxybenzamide |
| 51 | 2-chloro-N-[2-(4,4-difluoropiperidin-1-yl)-2-(4-methyl-1,3-oxazol-5-yl)ethyl]-5-(5-fluoropyrimidin-2-yl)benzamide |
| 52 | 2-chloro-N-[2-(4,4-difluoropiperidin-1-yl)-2-(4-methyl-1,3-oxazol-5-yl)ethyl]-6-fluorobenzamide |
| 53 | 2,3-dimethoxy-N-[2-(4-methyl-1,3-oxazol-5-yl)-2-(morpholin-4-yl)ethyl]benzamide |
| 54 | 2-chloro-5-(5-fluoropyrimidin-2-yl)-N-[2-(4-methyl-1,3-oxazol-5-yl)-2-(morpholin-4-yl)ethyl]benzamide |
| 55 | 2-chloro-6-fluoro-N-[2-(4-methyl-1,3-oxazol-5-yl)-2-(morpholin-4-yl)ethyl]benzamide |
| 56 | 2,3-dimethoxy-N-[2-(4-methyl-1,3-oxazol-5-yl)-2-(1,2,3,4-tetrahydroisoquinolin-2-yl)ethyl]benzamide |
| 57 | 2-chloro-4-(5-fluoropyrimidin-2-yl)-N-[2-(4-methyl-1,3-oxazol-5-yl)-2-(1,2,3,4-tetrahydroisoquinolin-2-yl)ethyl]benzamide |
| 58 | 2-chloro-N-[2-(4,4-difluoropiperidin-1-yl)-2-(2,4-dimethyl-1,3-oxazol-5-yl)ethyl]-5-(5-fluoropyrimidin-2-yl)benzamide |
| 59 | N-{2-[4-(benzyloxy)piperidin-1-yl]-2-(4-methyl-1,3-thiazol-5-yl)ethyl}-2-chloro-6-fluorobenzamide |
| 60 | 2-chloro-6-fluoro-N-[2-(4-methyl-1,3-thiazol-5-yl)-2-(4-phenoxypiperidin-1-yl)ethyl]benzamide |
| 61 | 2-chloro-N-[2-(4,4-difluoropiperidin-1-yl)-2-(2-methyl-1,3-thiazol-5-yl)ethyl]-5-(5-fluoropyrimidin-2-yl)benzamide |
| 62 | N-{2-[4-(benzyloxy)piperidin-1-yl]-2-(2-methyl-1,3-thiazol-5-yl)ethyl}-2-chloro-6-fluorobenzamide |
| 63 | N-{2-[4-(benzyloxy)piperidin-1-yl]-2-(1,3-oxazol-5-yl)ethyl}-2-chloro-6-fluorobenzamide |
| 64 | 2-chloro-N-[2-(3,3-difluoropiperidin-1-yl)-2-(4-methyl-1,3-thiazol-5-yl)ethyl]-6-fluorobenzamide |
| 65 | 2-chloro-N-[2-(3,3-difluoroazetidin-1-yl)-2-(4-methyl-1,3-thiazol-5-yl)ethyl]-5-(5-fluoropyrimidin-2-yl)benzamide |
| 66 | 2-chloro-N-[2-(3,3-difluoropiperidin-1-yl)-2-(4-methyl-1,3-thiazol-5-yl)ethyl]-5-(5-fluoropyrimidin-2-yl)benzamide |
| 67 | 2-chloro-N-[2-(4,4-difluoropiperidin-1-yl)-2-[4-(trifluoromethyl)-1,3-thiazol-5-yl]ethyl]-6-fluorobenzamide |
| 68 | 2-chloro-N-[2-(4,4-difluoropiperidin-1-yl)-2-[4-(trifluoromethyl)-1,3-thiazol-5-yl]ethyl]-5-(5-fluoropyrimidin-2-yl) |
| 69 | 2-chloro-N-[2-(4,4-difluoropiperidin-1-yl)-2-[4-methyl($^2$H)-1,3-thiazol-5-yl]ethyl]-5-(5-fluoropyrimidin-2-yl)benzamide |

| Compound | IUPAC NAME |
|---|---|
| 70 | N-[2-(4,4-difluoropiperidin-1-yl)-2-(4-methyl-1,3-thiazol-5-yl)ethyl]-2-fluoro-5-(5-fluoropyrimidin-2-yl)benzamide |
| 71 | N-[2-(4,4-difluoropiperidin-1-yl)-2-(4-methyl-1,3-thiazol-5-yl)ethyl]-5-(5-fluoropyrimidin-2-yl)-2-methoxybenzamide |
| 72 | 2-chloro-N-[2-(4,4-difluoropiperidin-1-yl)-2-(4-methyl-1,3-thiazol-5-yl)ethyl]-5-(pyrazin-2-yl)benzamide |
| 73 | 2-chloro-5-(5-fluoropyrimidin-2-yl)-N-[2-(4-methyl-1,3-thiazol-5-yl)-2-(4-phenoxypiperidin-1-yl)ethyl]benzamide |
| 74 | 2-chloro-N-[2-(4,4-difluoropiperidin-1-yl)-2-(4-methyl-1,3-thiazol-5-yl)ethyl]-5-(6-methylpyridin-2-yl)benzamide |
| 75 | (+)-2-chloro-N-[2-(4,4-difluoropiperidin-1-yl)-2-(4-methyl-1,3-thiazol-5-yl)ethyl]-5-(5-fluoropyrimidin-2-yl)benzamide |
| 76 | (−)-2-chloro-N-[2-(4,4-difluoropiperidin-1-yl)-2-(4-methyl-1,3-thiazol-5-yl)ethyl]-5-(5-fluoropyrimidin-2-yl)benzamide |
| 77 | 2-chloro-N-[2-(4,4-difluoropiperidin-1-yl)-2-(4-methyl-1,3-thiazol-5-yl)ethyl]-5-(5-fluoropyrimidin-2-yl)-N- |
| 78 | 2-chloro-N-[2-(4,4-difluoropiperidin-1-yl)-2-(2-methyl-1,3-thiazol-5-yl)ethyl]-5-(pyrazin-2-yl)benzamide |
| 79 | 2-chloro-N-[2-(4,4-difluoropiperidin-1-yl)-2-(2-methyl-1,3-thiazol-5-yl)ethyl]-5-(6-methylpyridin-2-yl)benzamide |
| 80 | N-[2-(4,4-difluoropiperidin-1-yl)-2-(2-methyl-1,3-thiazol-5-yl)ethyl]-2-fluoro-5-(5-fluoropyrimidin-2-yl)benzamide |
| 81 | 2-chloro-N-[2-(4,4-difluoropiperidin-1-yl)-2-[2-(trifluoromethyl)-1,3-thiazol-5-yl]ethyl]-6-fluorobenzamide |
| 82 | 2-chloro-N-[2-(4,4-difluoropiperidin-1-yl)-2-[2-(trifluoromethyl)-1,3--1,3-thiazol-5-yl]ethyl]-5-(5- |
| 83 | N-[2-(4,4-difluoropiperidin-1-yl)-2-(2-ethyl-1,3-thiazol-5-yl)ethyl]-2-fluoro-6-(5-fluoropyrimidin-2-yl)benzamide |
| 84 | 2-chloro-N-[2-(4,4-difluoropiperidin-1-yl)-2-(2-ethyl-1,3-thiazol-5-yl)ethyl]-6-(5-fluoropyrimidin-2-yl)benzamide |
| 85 | 2-chloro-N-[2-(4,4-difluoropiperidin-1-yl)-2-(2-ethyl-1,3-thiazol-5-yl)ethyl]-6-fluorobenzamide |
| 86 | N-[2-(2-cyclopropyl-1,3-thiazol-5-yl)-2-(4,4-difluoropiperidin-1-yl)ethyl]-2-fluoro-5-(5-fluoropyrimidin-2-yl)benzamide |
| 87 | 2-chloro-N-[2-(2-cyclopropyl-1,3-thiazol-5-yl)-2-(4,4-difluoropiperidin-1-yl)ethyl]-5-(5-fluoropyrimidin-2- |
| 88 | 2-chloro-N-[2-(2-cyclopropyl-1,3-thiazol-5-yl)-2-(4,4-difluoropiperidin-1-yl)ethyl]-6-fluorobenzamide |
| 89 | 2-chloro-4-(5-fluoropyrimidin-2-yl)-N-[2-(2-methyl-1,3-thiazol-5-yl)-2-(1,4-oxazepan-4-yl)ethyl]benzamide |
| 90 | 2-chloro-6-fluoro-N-[2-(4-methyl-1,3-thiazol-5-yl)-2-{2-[2-(trifluoromethyl)phenyl]morpholin-4-yl}ethyl]benzamide |
| 91 | 2-chloro-N-{2-[2-(2,4-difluorophenyl)morpholin-4-yl]-2-(4-methyl-1,3-thiazol-5-yl)ethyl}-6-fluorobenzamide |
| 92 | 2-chloro-6-fluoro-N-[2-(4-methyl-1,3-thiazol-5-yl)-2-[2-(1-methyl-1H-pyrazol-4-yl)morpholin-4-yl]ethyl]benzamide |
| 93 | 2-chloro-5-(5-fluoropyrimidin-2-yl)-N-[2-(4-methyl-1,3-thiazol-5-yl)-2-{5-oxa-8-azaspiro[3.5]nonan-8-yl}ethyl]benzamide |
| 94 | 2-fluoro-5-(5-fluoropyrimidin-2-yl)-N-[2-(4-methyl-1,3-thiazol-5-yl)-2-{5-oxa-8-azaspiro[3.5]nonan-8-yl}ethyl]benzamide |
| 95 | 2-chloro-N-{2-[4-(difluoromethyl)-1,3-thiazol-5-yl]-2-(4,4-difluoropiperidin-1-yl)ethyl}-6-fluorobenzamide |
| 96 | 2-chloro-6-fluoro-N-[2-(4-methyl-1,3-thiazol-5-yl)-2-{5-oxa-8-azaspiro[3.5]nonan-8-yl}ethyl]benzamide |
| 97 | 2-chloro-5-(5-fluoropyrimidin-2-yl)-N-[2-(4-methyl-1,3-thiazol-5-yl)-2-[2-(1-methyl-1H-pyrazol-4-yl)morpholin-4- |
| 98 | 2-fluoro-5-(5-fluoropyrimidin-2-yl)-N-[2-(4-methyl-1,3-thiazol-5-yl)-2-[2-(1-methyl-1H-pyrazol-4-yl)morpholin-4- |
| 99 | N-{2-[2-(2,4-difluorophenyl)morpholin-4-yl]-2-(4-methyl-1,3-thiazol-5-yl)ethyl}quinoline-5-carboxamide |
| 100 | 2-chloro-N-{2-[2-(2,4-difluorophenyl)morpholin-4-yl]-2-(4-methyl-1,3-thiazol-5-yl)ethyl}-6-methylbenzamide |
| 101 | 2-chloro-N-{2-[2-(2,4-difluorophenyl)morpholin-4-yl]-2-(4-methyl-1,3-thiazol-5-yl)ethyl}-6-methylbenzamide |
| 102 | 2-chloro-N-{2-[4-(difluoromethyl)-1,3-thiazol-5-yl]-2-(4,4-difluoropiperidin-1-yl)ethyl}-5-(5-fluoropyrimidin-2-yl)benzamide |
| 103 | 2-chloro-N-[2-(4,4-difluoro-2-methylpiperidin-1-yl)-2-(4-methyl-1,3-thiazol-5-yl)ethyl]-5-(5-fluoropyrimidin-2-yl)benzamide |
| 104 | 2-chloro-N-[2-(4,4-difluoro-2-methylpiperidin-1-yl)-2-(4-methyl-1,3-thiazol-5-yl)ethyl]-6-fluorobenzamide, |
| 105 | N-[2-(2-cyclobutyl-1,3-thiazol-5-yl)-2-(4,4-difluoropiperidin-1-yl)ethyl]quinoline-5-carboxamide |
| 106 | N-[2-(2-cyclobutyl-1,3-thiazol-5-yl)-2-(4,4-difluoropiperidin-1-yl)ethyl]-2-fluoro-5-(5-fluoropyrimidin-2-yl)benzamide |
| 107 | 2-chloro-N-[2-(4,4-difluoropiperidin-1-yl)-2-(2-propyl-1,3-thiazol-5-yl)ethyl]-5-(5-fluoropyrimidin-2-yl)benzamide |
| 108 | N-[2-(4,4-difluoropiperidin-1-yl)-2-(2-propyl-1,3-thiazol-5-yl)ethyl]quinoline-5-carboxamide |
| 109 | 2-chloro-N-[2-(4,4-difluoropiperidin-1-yl)-2-(2-propyl-1,3-thiazol-5-yl)ethyl]-6-fluorobenzamide |
| 110 | 2-chloro-N-[2-(2-cyclobutyl-1,3-thiazol-5-yl)-2-(4,4-difluoropiperidin-1-yl)ethyl]-6-fluorobenzamide |
| 111 | 2-chloro-N-[2-(2-cyclobutyl-1,3-thiazol-5-yl)-2-(4,4-difluoropiperidin-1-yl)ethyl]-5-(5-fluoropyrimidin-2- |
| 112 | 2-chloro-N-[2-(4,4-difluoropiperidin-1-yl)-2-[2-(hydroxymethyl)-1,3-thiazol-5-yl]ethyl]-5-(5-fluoropyrimidin-2- |
| 113 | 2-chloro-N-[2-(4,4-difluoro-2-methylpiperidin-1-yl)-2-(2-methyl-1,3-thiazol-5-yl)ethyl]-5-(5-fluoropyrimidin-2-yl) |
| 114 | 2-chloro-N-[2-(4,4-difluoropiperidin-1-yl)-2-(4-methyl-1,3-thiazol-5-yl)ethyl]-4-(1,1-dioxo-1☐⁶,2-thiazolidin-2- |
| 115 | N-{2-[2-(4,4-difluorocyclohexyl)-1,3-thiazol-5-yl]-2-(morpholin-4-yl)ethyl}quinoline-6-carboxamide |
| 116 | 2-chloro-N-{2-[2-(4,4-difluorocyclohexyl)-1,3-thiazol-5-yl]-2-(morpholin-4-yl)ethyl}-6-fluorobenzamide |
| 117 | 2-chloro-N-{2-[2-(4,4-difluorocyclohexyl)-1,3-thiazol-5-yl]-2-(4,4-difluoropiperidin-1-yl)ethyl}-6-fluorobenzamide |
| 118 | N-[2-(2-tert-butyl-1,3-thiazol-5-yl)-2-(4,4-difluoropiperidin-1-yl)ethyl]-2-chloro-6-fluoro-benzamide |
| 119 | 2-chloro-N-[2-(4-cyclopropyl-1,3-thiazol-5-yl)-2-(4,4-difluoropiperidin-1-yl)ethyl]-5-(5-fluoropyrimidin-2- |
| 120 | N-[2-(4,4-difluoropiperidin-1-yl)-2-(4-methyl-1,3-thiazol-5-yl)ethyl]-7-fluoro-2-oxo-1,2,3,4-tetrahydroquinoline-6- |
| 121 | N-[2-(4-cyclopropyl-1,3-thiazol-5-yl)-2-(4,4-difluoropiperidin-1-yl)ethyl]quinoline-5-carboxamide |
| 122 | N-[2-(2-tert-butyl-1,3-thiazol-5-yl)-2-(4,4-difluoropiperidin-1-yl)ethyl]-2-chloro-5-(5-fluoropyrimidin-2-yl)benzamide |
| 123 | 2-chloro-N-[2-(4-cyclopropyl-1,3-thiazol-5-yl)-2-(4,4-difluoropiperidin-1-yl)ethyl]-6-fluorobenzamide |
| 124 | N-[2-(2-tert-butyl-1,3-thiazol-5-yl)-2-(4,4-difluoropiperidin-1-yl)ethyl]quinoline-5-carboxamide |
| 125 | 2-chloro-N-{2-[2-(4,4-difluorocyclohexyl)-1,3-thiazol-5-yl]-2-(morpholin-4-yl)ethyl}-5-(5-fluoropyrimidin-2-yl)benzamide |
| 126 | 2-chloro-N-{2-[2-(4,4-difluorocyclohexyl)-1,3-thiazol-5-yl]-2-(4,4-difluoropiperidin-1-yl)ethyl}-5-(5-fluoropyrimidin-2- |
| 127 | (+)-2-chloro-N-[2-(4,4-difluoro-piperidin-1-yl)-2-(2-methylthiazol-5-yl)ethyl]-5-(5-fluoropyrimidin-2-yl)benzamide |
| 128 | (−)-2-chloro-N-[2-(4,4-difluoro-piperidin-1-yl)-2-(2-methylthiazol-5-yl)ethyl]-5-(5-fluoropyrimidin-2-yl)benzamide |
| 129 | 2-chloro-N-{2-[4-(difluoromethyl)-1,3-thiazol-5-yl]-2-(morpholin-4-yl)ethyl}-5-(5-fluoropyrimidin-2-yl)benzamide |
| 130 | 2-chloro-N-{2-[4-(difluoromethyl)-1,3-thiazol-5-yl]-2-(morpholin-4-yl)ethyl}-6-fluorobenzamide |

Compounds of formula (I) can generally be prepared by reacting a compound of formula (II):

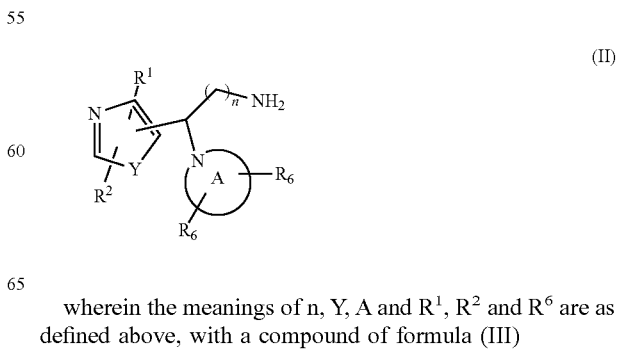

(II)

wherein the meanings of n, Y, A and $R^1$, $R^2$ and $R^6$ are as defined above, with a compound of formula (III)

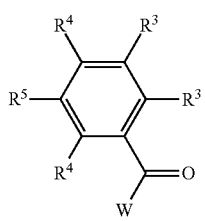

(III)

wherein the meanings of $R^3$, $R^4$ and $R^5$ are as defined above; or with a compound of Formula (IIIa):

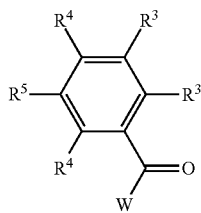

(IIIa)

wherein the meanings of $R^3$, $R^4$ and $R^5$ are as defined above, and W is a suitable leaving group;

and optionally converting the obtained compound of formula (I) into an addition salt thereof, and/or preparing stereochemically isomeric forms thereof.

The reaction of a compound of formula (II) with a compound of formula (III), may be carried out in a at least one reaction-inert solvent and optionally in the presence of at least one suitable coupling reagent and/or a suitable base thereof. It may be convenient to activate the carboxylic acid of formula (III) by adding an effective amount of a reaction promoter. Non-limiting examples of such reaction promoters include carbonyldiimidazole, N,N'-dicyclohexyl-carbodiimide or 1-(3-dimethylaminopropyl)-3-ethylcarbodiimide, hydroxybenzotriazole, benzotriazolyl-oxytris (dimethylamino)-phosphoniumhexafluorophosphate, tetrapyrrolidinophosphoniumhexafluorophosphate, bromotripyrrolidinophosphonium hexafluorophosphate, or a functional derivative thereof, such as disclosed by D. Hudson, (J. Org. Chem. (1988), 53, 617).

W in the compound of Formula (IIIa) is an appropriate leaving group such as, for example, halo, e.g. fluoro, chloro, bromo, iodo, or in some instances W may also be a sulfonyloxy group, e.g. methanesulfonyloxy, trifluoromethanesulfonyloxy, benzenesulfonyloxy and the like reactive leaving groups. The reaction of a compound of formula (II) with a compound of formula (III), may be performed in a reaction-inert solvent such as, for example, acetonitrile, dimethyl acetamide, N-methyl-pyrrolidone or DMF, and optionally in the presence of a suitable base such as, for example, sodium carbonate, potassium carbonate or triethylamine. Stirring may enhance the rate of the reaction. The reaction may conveniently be carried out at a temperature ranging between room temperature and the reflux temperature of the reaction mixture.

Compounds of formula (III) and (IIIa) are known in the art or can be prepared following the processes reported in the examples.

Compounds of formula (II) can be prepared according to the following scheme:

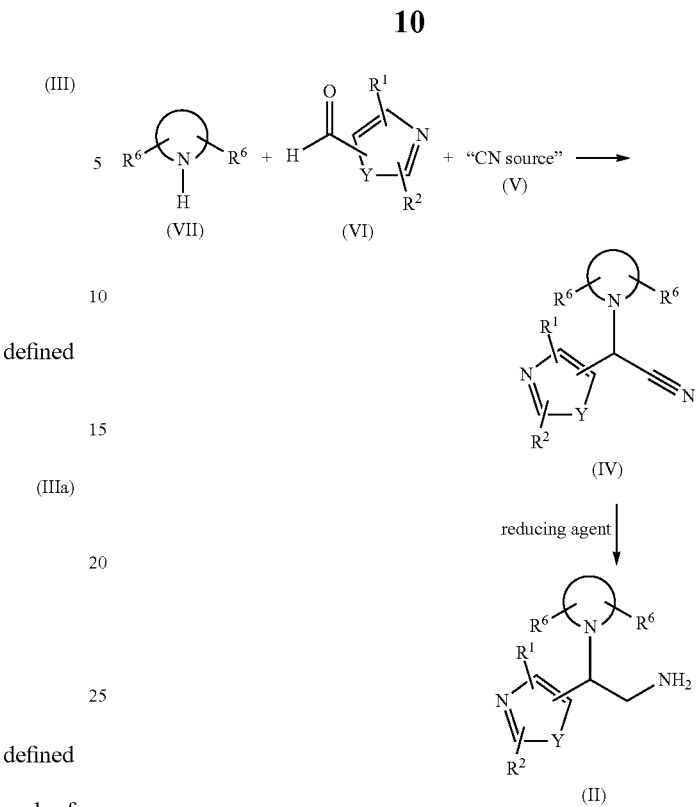

Primary amines (II) can be obtained by reduction of the respective nitrile derivatives (IV) in a nitrogen-hydrogen bond forming reaction. Non-limiting examples of such reaction include reduction with:

hydrogen or a hydrogen source in the presence of a metal such as nickel, platinum, palladium and cobalt or a derivative thereof such as Ni-Raney, platinum oxide, palladium oxide or Raney cobalt as catalyst;

a hydride such as lithium aluminum hydride, diisobutylaluminum hydride (DIBAL), boron hydride or a functional derivative thereof.

The reaction may be performed in a suitable solvent, such as methanol, tetrahydrofuran, acetic acid, diethyl ether, toluene or methanolic ammonia solution preferably at temperatures between −78° C. and RT.

Compounds of formula (IV), wherein R1, R2, and R6 are as defined in formula (I), can be prepared from aldehydes (VI) by a Strecker condensation reaction with the respective heterocyclyl intermediate (VII) in presence of a source of cyanide (V) for example TMSCN or a functional derivative thereof, in a solvent such as AcOH or MeCN, preferably at temperatures between 0° C. and RT.

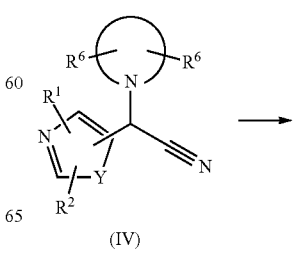

(IV)

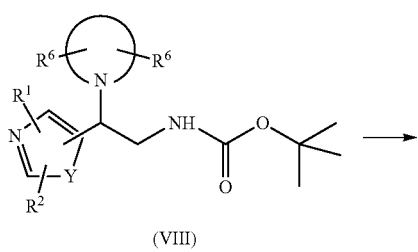

(VIII)

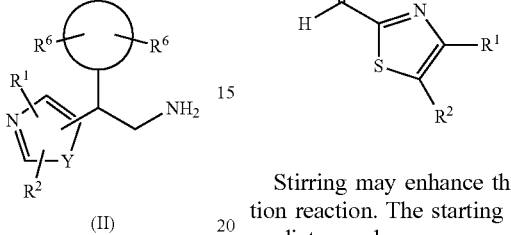

(II)

Alternatively, compounds of formula (II) can also be prepared by a two step procedure as reported above. Reaction of compounds of formula (IV) with a reducing reagent, preferably sodium borohydride in presence of nickel(II) chloride hexahydrate or cobalt(II) chloride hexahydrate and $Boc_2O$ in a solvent such as MeOH, preferably at temperatures between 0° C. and RT, yields the Boc-protected primary amine with formula (VIII). Deprotection with a suitable acid, preferably TFA, gives compounds (II).

Examples of compounds of formula (VI) are represented in the following scheme:

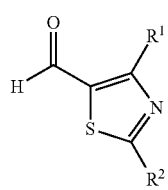

(VIa)

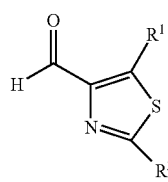

(VIb)

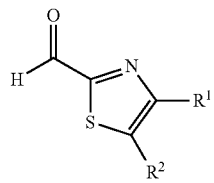

(VIc)

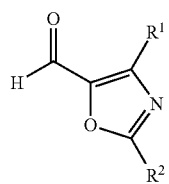

(VId)

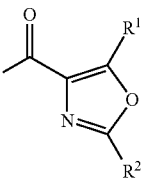

(VIe)

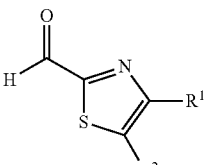

(VIf)

Stirring may enhance the rate of the Strecker condensation reaction. The starting materials and some of the intermediates are known compounds and are commercially available or may be prepared according to conventional reaction procedures generally known in the art.

The said process further optionally comprising asymmetric reaction using chiral auxiliaries based synthesis (using carbohydrate, chiral amine or cyclic ketimine) and/or catalytic asymmetric Strecker synthesis (using guanidine, chiral Schiff base or BINOL-based catalyst).

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example,by selective or fractional crystallization and the enantiomers are liberated there from by alkali. An alternative manner of separating the enantiomeric forms of the compounds of formula (1) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess P2X7 receptor antagonizing properties as demonstrated in the Pharmacological Examples. Other examples of art-known group transformation reactions to convert compounds of formula (I) into other compounds of formula (I) are hydrolysis of carboxylic esters to the corresponding carboxylic acid or alcohol; hydrolysis of amides to the corresponding carboxylic acids or amines; alcohols may be converted into esters and ethers; primary amines may be converted into secondary or tertiary amines; double bonds may be hydrogenated to the corresponding single bond. The starting materials and some of the intermediates are known compounds and are commercially available or may be prepared according to conventional reaction procedures generally known in the art. The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. In the preparation of the compounds of formula I and the starting materials and/or intermediates described herein it may be useful to protect certain groups which are sensitive to the reaction conditions. The evaluation of the usefulness of the optional protection, as well as the selection of the suitable protecting agent, according to the reaction carried out in the preparation of the compounds of the invention and the functional group to be protected, are within the common knowledge of the skilled person. The removal of the optional protective groups is carried out according to conventional techniques. For a general reference to the use of protective groups in orgamic chemistry, see Theodora W. Greene and Peter G. M. Wuts "Protective groups in organic synthesis", John Wiley & Sons, Inc., II Ed., 1991.

The preparation of the salts of the compounds of formula I is carried out according to known methods. Therefore the present compounds of formula (I) are useful as a medicine especially in the treatment of a condition or disease mediated by the P2X7 receptor, in particular P2X7 receptor antagonistic activity. Subsequently the present compounds may be used for the manufacture of a medicine for treatment of a condition or a disease mediated by P2X7 receptor activity, in particular P2X7 receptor antagonistic activity.

The present invention also provides the use of a compound of formula (I) or a pharmaceutically acceptable salt thereof for the manufacture of a medicament for the treatment of conditions or diseases selected from P2X7 receptor mediated conditions or diseases. In an embodiment, the present invention provides a compound of formula (I) for use as a medicine or for use in the treatment of conditions or diseases selected from P2X7 receptor mediated conditions or diseases. Further, the present invention also provides a method of treatment of a condition mediated by P2X7 receptor activity, in a mammalian subject, which method comprises administering to a mammal in need of such treatment a therapeutically effective amount of a compound of formula (I) or a pharmaceutically acceptable salt thereof. In view of the above described mechanisms of action, the compounds of the invention are useful for the treatment of neurodegenerative disorders of various origins such as Alzheimer's Disease and other dementia conditions such as Lewys body, fronto-temporal dementia and taupathies; amyotrophic lateral sclerosis, Multiple Sclerosis, Parkinson's Disease and other parkinsonian syndromes; HIV-induced neuroinflammation; essential tremors; other spino cerebellar degenerations and Charcot-Marie-Toot neuropathy. The compounds of the invention are also useful for the treatment of neurological conditions such as epilepsy including simple partial seizure, complex partial seizure, second-ary generalized seizure, further including absence seizure, myoclonic seizure, clonic seizure, tonic seizure, tonic clonic seizure and atonic seizure, and for prevention and treatment of Status Epilepticus (SE).

The compounds of the invention are also useful for the treatment of cognitive disorders and of psychiatric disorders. Psychiatric disorders include, and are not limited to major depression, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behaviour, delusional disorders, brief psychotic disorders, shared psychotic disorders, psychotic disorder due to a general medical condition, substance-induced psychotic disorders or a psychotic disorder not otherwise specified, anxiety disorders such as generalised anxiety disorder, panic disorders, post-traumatic stress disorder, impulse control disorders, phobic disorders, dissociative states and moreover in smoke, drug addiction and alcoholism. In particular bipolar disorders, psychosis, anxiety and addiction.

The compounds of the present invention are useful in the prevention or treatment of neuroinflammation and CNS damage induced by HIV infection and of HIV-associated neurocognitive deficits. The compounds of the present invention are useful in the prevention or treatment of neuropathic pain. Neuropathic pain syndromes include, and are not limited to: diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and peripheral forms of pain such as complex regional pain syndromes (CRPS) also called reflex sympathetic dystrophies.

The compounds of the invention are also useful for the treatment of chronic pain. Chronic pain includes, and is not limited to, chronic pain caused by inflammation or an inflammatory-related condition, ostheoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds of the invention are also useful in the treatment of acute pain caused by acute injury, illness, sport-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis or surgery (such as open heart or bypass surgery), post operative pain, kidney stone pain, gallbladder pain, gallstone pain, obstetric pain or dental pain.

The compounds of the invention are also useful in the treatment of headaches such as migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

Compounds of the invention are also useful in the treatment of diseases such as vertigo, tinnitus, muscle spasm, and other disorders including and not limited to cardiovascular diseases (such as cardiac arrhythmia, cardiac infarction or angina pectoris, hypertension, cardiac ischemia, cerebral ischemia) endocrine disorders (such as acromegaly or diabetes insipidus) diseases in which the pathophysiology of the disorder involves excessive or hypersecretory or otherwise inappropriate cellular secretion of an endogenous substance (such as catecholamine, a hormone or a growth factor).

The compounds of the invention are also useful in the selective treatment of liver disease, such as inflammatory liver diseases, for example chronic viral hepatitis B, chronic viral hepatitis C, alcoholic liver injury, primary biliary cirrhosis, autoimmune hepatitis, liver fibrosis, non-alcoholic steatohepatitis and liver transplant rejection.

The compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as alkylosing spondylitis, cervical arthritis, fibromyalgia, gout, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis nodosa, thyroiditis, aplastic anaemia, scleroderma, myasthenia gravis, multiple sclerosis and other demyelinizating disorders, encephalomyelitis, sarcoidosis, nephritic syndrome, Bechet's syndrome, polymyositis, gingivitis.

Compounds of the invention are also useful in the treatment of gastrointestinal (GI) tract disorders such as inflammatory bowel disorders (IBD) including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyrosis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhoea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexities, pelvic inflammation, bartholinities and vaginitis. In particular, overactive bladder and urinary incontinence.

The compounds of the invention are also useful in the treatment of ophthalmic diseases such as retinitis, retinopathies, uveitis and acute injury to the eye tissue, age-related macular degeneration or glaucoma, conjunctivitis.

The compounds of the invention are also useful in the treatment of eating disorders such as anorexia nervosa including the subtypes restricting type and binge-eating/purging type; bulimia nervosa including the subtypes purging type and non-purging type; obesity; compulsive eating disorders; binge eating disorder; and eating disorder not otherwise specified.

The compounds of the invention are also useful in the treatment of allergie dermatitis, hyperresponsiveness of the airway, chronic obstructive pulmonary disease (COPD), bronchitis, septic shock, Sjogren's syndrome, glomerulonephritis, atherosclerosis, growth and metastases of malignant cells, myoblastic leukaemia,diabetes, meningitis, osteoporosis, burn injury, ischaemic heart disease, stroke, peripheral vascular disease, varicose veins, glaucoma.

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oralliquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient.

Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (1), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage.

"Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulo se and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitarne, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume). The pharmaceutically acceptable flavours which can mask the bitter tasting ingredients in the low-dosage formulations comprise preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like.

Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the ligand-gated ion channels will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible P2X7 receptor antagonistic response.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

Nomenclature and Structures

In general, the nomenclature used in this Application is based on ChemSketch™ (ACDLabs) and generated according to the IUPAC systematic nomenclature. Chemical structures shown herein were prepared using ISIS® version 2.2. Any open valency appearing on a carbon, oxygen, sulfur, or nitrogen atom in the structures herein indicates the presence of a hydrogen atom unless indicated otherwise. Where a nitrogen-containing heteroaryl ring is shown with an open valency on a nitrogen atom and variables such as $R^1$, $R^2$, $R^3$ etc. are shown on the heteroaryl ring, such variables may be bound or joined to the open valency nitrogen. Where a chiral center exists in a structure but no specific stereochemistry is shown for the chiral center, both enentiomers associated with the chiral center are encompassed by the structure. Where a structure shown herein may exist in multiple tautomeric forms, all such tautomers are encompassed by the structure. The atoms represented in the structure herein are intended to encompass all naturally occurring isotopes of such atoms. Thus, for example, the hydrogen atoms represented herein are meant to include deuterium and tritium, and the carbon atoms are meant to include $^{13}C$ and $^{14}C$ isotopes.

Abbreviations

Abbreviations which are used in the description of the Schemes and the Examples that follows are:

AcOH: Acetic acid
Anh: Anhydrous
AcONa: Sodium acetate
Boc: Tert-butyl-carbonate
Boc$_2$O: Di-tert-butyl dicarbonate
CC: Column Chromatography
DAST: Diethylaminosulfur trifluoride
DCM: Dichloromethane
DEA: Diethylamine
DIAD: Diisopropylazodicarboxylate
DIBAL: Diisobutylaluminiumhydride
DIPEA: Diisopropylethylenamine
DMAP: Dimethylaminopyridine
DMF: Dimethylformamide
DMSO: Dimethylsulfoxide
Et$_2$O: Diethyl ether
EtOAc: Ethyl acetate
EtOH: Ethanol
ESI: Electrospray ionization
HBTU: N,N,N',N'-Tetramethyl-O-(1H-benzotriazol-1-yl) uronium hexafluorophosphate;
h: hour;
Hrs hours
M: Molar
MeCN: Acetonitrile
MeOH: Methanol
Min: Minute(s)
Ni-Raney: Nickel-Raney
NMR: Nuclear Magnetic Resonance
rt: Room Temperature
TFA Trifluoroacetic acid
THF: Tetrahydrofurane;
TLC: Thin Layer Chromatography
TMSCN Trimethylsilylcyanide;
UPLC-MS: UltraPerformance LiquidChromatography-Mass Spectrometry
XPhos: 4,5-bis(diphenylphosphino)-9,9-dimethylxantene.

EXPERIMENTAL PART

The following examples illustrate the present invention. Unless explicitly stated otherwise, all particulars (especially percentages and amounts) relate to the weight A Synthesis of the Intermediates Example A.1 a) Preparation of

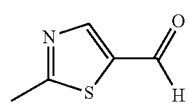

intermediate (1)

2-Bromomalonaldehyde (1.5 g, 9.94 mmol, 1 eq;) and thioacetamide (0.83 g, 11.05 mmol, 1.11 eq) were suspended in DCM (10 mL) and cooled to 0° C.; then DIPEA (1.75 mL, 10.05 mmol, 1.01 eq) was added dropwise. The resulting brown solution was left under stirring at room temperature for 3 days. Then the reaction mixture was diluted with water (50 mL), and the organic phase was collected. The aqueous phase was extracted three times with DCM (10 mL). The organic phase was dried over anh. Na$_2$SO$_4$, filtered and evaporated. The brown residue was dissolved in Et$_2$O (20 mL), washed twice with NaHCO$_3$ sat. solution (20 mL) and brine (20 mL), dried over anh. Na$_2$SO$_4$, filtered, and finally evaporated, to afford the pure title product as a brown oil (0.40 g, yield 31%).

Example A.2 a) Preparation of

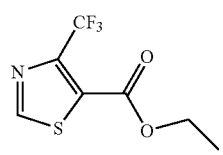

intermediate (2a)

Ethyl 2-amino-4-(trifluoromethyl)-5-thiazole-carboxylate (1.15 g, 4.79 mmol, 1 eq) was dissolved in 1.3-dioxane (27 mL) and isoamylnitrite (1.51 g, 12.93 mmol, 2.7 eq) was added dropwise at room temperature. The reaction mixture was heated at 80° C. and after 1 h, complete conversion of the starting material was observed by TLC (80/20 petroleum ether/EtOAc). The solvent was removed in vacuo and the crude purified by flash chromatography on direct phase (95/5→90/10 petroleum ether/EtOAc), giving pure 2a (0.94 g, yield 87%) as yellow oil.

b) Preparation of

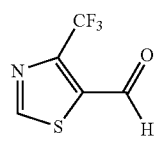

intermediate (2b)

Intermediate 2a (0.82 g, 3.66 mmol, 1 eq) was dissolved in dry DCM (18 mL) under argon atmosphere and cooled to −70° C. Then 1M DIBAL in DCM (4.1 mL, 4.10 mmol, 1.12 eq) was added dropwise over 10 minutes and the mixture stirred at the same temperature for 1.5 h. The reaction mixture was brought to 0° C., water (0.186 mL), 15% NaOH (0.186 mL) and a second portion of water (0.186 mL) were sequentially added and the mixture stirred until complete precipitation of the aluminium salt (5 min). The mixture was dried over anhydrous $Na_2SO_4$ and filtered. After solvent evaporation, the crude was purified by flash chromatography on direct phase (20/80→50/50 DCM/petroleum ether), giving pure intermediate (2b) as yellow oil (0.3 g, yield 45%).

Example A.3 a) Preparation of

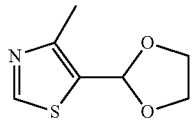

intermediate (3a)

p-Toluenesulfonic acid monohydrate (0.03 g, 0.16 mmol, 0.08 eq) was added to a mixture of 4-methyl-1,3-thiazole-5-carbaldehyde (0.25 g, 1.97 mmol, 1 eq) and 1,2-ethanediol (0.38 mL, 6.88 mmol, 3.5 eq) in anhydrous toluene (5.5 mL). The flask was fitted with a Dean-Stark trap and the mixture heated to reflux for 6 h. After cooling to ambient temperature, the reaction was quenched with 10% $Na_2CO_3$ solution (15 mL). The aqueous layer was extracted with ethyl acetate (10 mL×3). The combined extracts were dried over anhydrous $Na_2SO_4$, filtered, and concentrated. The residue was purified by silica gel column (100% DCM→30/70 EtOAc/DCM) to give the intermediate (3a) as yellow oil (0.29 g, yield 86%).

b) Preparation of

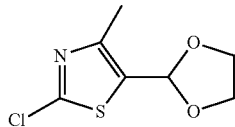

intermediate (3b)

1.6 M n-butyllithium in hexane (1.28 mL, 2.05 mmol, 1.5 eq) was dropwise added to a solution of intermediate (3a) (0.23 g, 1.37 mmol, 1 eq) in dry THF (4.5 mL) at −70° C. under argon atmosphere. The resulting dark solution was stirred at −70° C. for 30 min, than 1.05M carbon tetrachloride in dry THF (2 mL, 2.10 mmol, 1.5 eq) was dropwise added at the same temperature. After 1 h the reaction was quenched with a saturated aqueous solution of $NH_4Cl$ (1 mL) and was brought at room temperature. The mixture was partitioned between water (10 mL) and AcOEt (10 mL) and the aqueous layer was extracted with AcOEt (10 mL×3). The combined extracts were dried over anhydrous $Na_2SO_4$, filtered, and concentrated. The residue was purified by silica gel chromatography (100% DCM→5/95 EtOAc/DCM 0%) to give intermediate (3b) as dark oil (0.208 g, yield 74%).

c) Preparation of

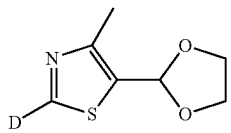

intermediate (3c)

1.6 M n-butyllithium in hexane (0.632 mL, 1.01 mmol, 2 eq) was dropwise added to a solution of (3b) (0.10 g, 0.51 mmol, 1 eq) in dry THF (2.4 mL) at −70° C. under argon atmosphere. The resulting dark solution was stirred at −70° C. for 30 min. The reaction was quenched with deuterium oxide (2 mL) and was brought to room temperature. The mixture was partitioned between brine (10 mL) and AcOEt (10 mL) and the aqueous layer was extracted with AcOEt (10 mL×2). The combined extracts were dried over anhydrous $Na_2SO_4$, filtered, and concentrated. The residue was purified on a direct phase silica gel column (20/80 AcOEt/DCM) to give intermediate (3c) as a yellow oil (0.79 g, yield 90%).

d) Preparation of

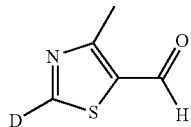

intermediate (3d)

Aqueous 5.0M HCl (0.19 mL, 0.96 mmol, 2.5 eq) was added to a solution of intermediate (3c) (0.07 g, 0.38 mmol, 1.0 eq) in THF (1 mL) was added. The resulting mixture was stirred at room temperature for 1.5 h. The mixture was partitioned between brine (10 mL) and AcOEt (10 mL) and the aqueous layer was extracted with AcOEt (10 mL×2). The combined organic extracts were washed with saturated sodium bicarbonate (20 mL), dried over anhydrous $Na_2SO_4$, filtered, and concentrated to give intermediate (3d) as yellow solid (0.37 g, 74.7%).

Example A.4

Preparation of

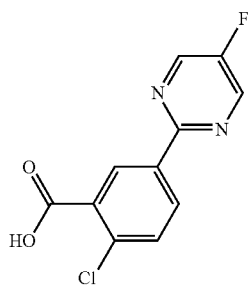

intermediate (4)

In a microwave vial (20 mL volume), 3-carboxy-4-chlorophenylboronic acid (0.210 g, 1 mmol, 1.0 eq), 2-chloro-5-fluoro-1,3-pyrimidine (0.175 g, 1.25 mmol, 1.25 eq), tetrakis(triphenylphosphine)palladium(0) (0.023 g, 0.02 mmol, 0.02 eq) and cesium carbonate (0.5 g, 1.5 mmol, 1.5 eq) were suspended in a degassed 5/1 DMF/$H_2O$ solution (2.5 mL). The vial was sealed, flushed with nitrogen and mechanically stirred for 5 min. The mixture was then heated for 4 h at at 80° C. in a microwave reactor. The resulting yellow suspension, was evaporated in vacuo, water (20 mL) was added, followed by 1/1 DCM/AcOEt (20 mL) and 37% HCl (10 mL). The resulting solution was poured in a separating funnel and extracted twice with 1/1 DCM/EtOAc. The combined organic extracts were dried over anhydrous Na$_2$SO$_4$, filtered and evaporated giving intermediate (4) as white powder (0.214 g, yield 85%).

Using a similar procedure intermediate (5) was prepared starting from 3-carboxy-4-methoxyphenylboronic acid (0.248 g, yield 99%), and intermediate (6) was prepared starting from 3-carboxy-4-fluorophenylboronic acid (0.235 g, yield 99%).

Using a similar procedure but replacing 2-chloro-5-fluoro-1,3-pyrimidine with 2-chloropyrazine, intermediate (7) was prepared starting from 3-carboxy-4-chlorophenylboronic acid (0.1 g, yield 85%)

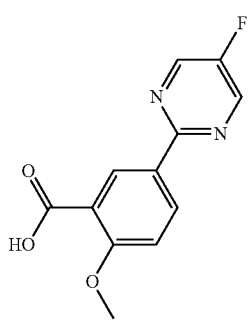
(Intm. (5))

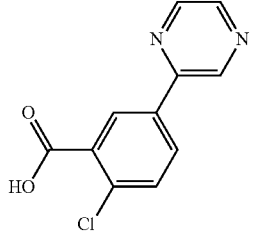
(Intm. (6))

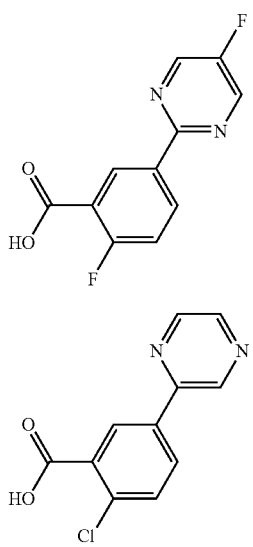
(Intm. (7))

Example A.5

Preparation of

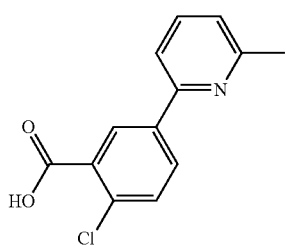
intermediate (8)

In a microwave vial (20 mL volume), 3-carboxy-4-chlorophenylboronic acid (0.218 g, 0.92 mmol, 2.0 eq), 2-chloro-6-methylpyridine (0.05 mL, 0.46 mmol, 1 eq), palladiumacetate (0.017 g, 0.08 mmol, 0.17 eq), Xphos (0.09 g, 0.157 mmol, 0.34 eq) and sodium carbonate (0.147 g, 3 mmol, 3 eq) were suspended in degassed 10/1 dioxane/H$_2$O solution (2.5 mL). The vial was sealed, flushed with nitrogen and mechanically stirred for 5 min. The mixture was then heated for 2 h at at 80° C. in a microwave reactor. The resulting black suspension, was evaporated in vacuo, water (20 mL) was added, followed by 1/1 DCM/AcOEt (20 mL) and 37% HCl (10 mL). The resulting solution was poured in a separating funnel and the acqueous layer separated and evaporated. The resulting white powder was treated with MeOH (3 mL), filtered and finally evaporated, affording intermediate (8) as white powder (0.11 g, yield 95%).

Example A.6

Preparation of

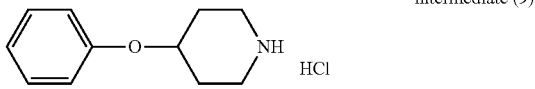
intermediate (9)

Triphenylphosphine (1.69 g, 6.46 mmol, 1.3 eq) was added to a mixture of 4-hydroxy-N-Boc-piperidine (1.00 g, 4.97 mmol, 1 eq) and phenol (0.51g, 5.47mmol, 1.1 eq) in dry THF (8.5 mL), DIAD (1.27 mL, 6.46 mmol, 1.3 eq) was then added slowly in 10 minutes. The mixture was stirred at room temperature overnight, then the solvent was evaporated and the residue was purified by flash chromatography over silica gel (eluent petroleum ether/EtOAc 95/5 to 90/10). 4-phenoxy-N-boc-piperidine was obtained as a pale pink oil (0.72 g, 2.61mmol, yield 52%).

4-Phenoxy-N-boc-piperidine (0.72 g, 2.61 mmol, 1 eq) was dissolved in a 4M solution of HCl in dioxane (5 mL) and the solution was stirred at room temperature for 2 hours. The solution was evaporated and the residue was dried under hight vacuum. The residue was then triturated with MeCN (5 mL), filtered and washed with MeCN (1-2 mL) giving intermediate (9) as a white solid (0.45 g, 2.09 mmol, yield 81%).

Example A.7

Preparation of intermediate (10)

4-hydroxy-N-Boc-piperidine (1.18 g, 4.97 mmol, 1 eq) was dissolved in dry THF (10 mL) and the solution was cooled to 0°, then NaH (0.248 g, 60% dispersion in mineral oil, 5.96 mmol, 1.2 eq) was added portionwise. The suspension was vigorously stirred at room temperature for 30 min. Then, benzyl bromide (1.1 g, 6.46 mmol, 1.3 eq) was added dropwise and the mixture was heated to reflux. After 1 hour NaH (0.103 g, 60% dispersion in mineral oil, 2.48 mmol, 0.5 eq) and benzyl bromide (0.423 g, 2.48 mmol, 0.5 eq) were sequentially added, and the mixture was stirred at room temperature for 1 hour. An additional portion of NaH (0.207 g, 60% dispersion in mineral oil, 5 mmol, 1 eq) was further added, and the reaction mixture was refluxed for 1 hour and stirred overnight at room temperature. The reaction mixture was poured into aq. saturated NH₄Cl (50 mL) and extracted with EtOAc (30 mL×3). The combined organic extracts were dried over anh. Na₂SO₄, filtered, and the solvent was removed in vacuo. The residue was purified by flash chromatography over silica gel (eluent 90/10 petroleum ether/ AcOEt), giving pure 4-benzyloxy-N-boc-piperidine (1.4 g, 4.83 mmol, yield 97%) as a colourless oil. 4-benzyloxy-N-boc-piperidine (1.4 g, 4.83 mmol, 1 eq) was dissolved in dioxane (10 mL). A 4M HCl solution in dioxane (5 mL) was added dropwise and the reaction mixture was stirred at room temperature for 5 hours. Then a 4M HCl solution in dioxane (3 mL) was added and the reaction mixture was stirred further at room temperature overnight. Finally, the solvent was removed in vacuo, giving pure intermediate (10) as an off-white solid (1 g, 4.38 mmol, yield 99%).

Example A.8

Preparation of

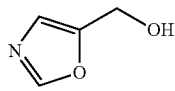

intermediate (11)

Ethyl oxazole-5-carboxylate (1 g, 7.09 mmol, 1 eq) was dissolved in EtOH (14 mL) and the mixture was cooled to 0° C. Sodium borohydride (0.54 g, 14.17 mmol, 2 eq) was added portionwise while stirring, and then the mixture was allowed to warm to r.t. After overnight stirring at r.t. the conversion was complete by TLC (95/5 DCM/MeOH). The mixture was cooled to 0° C. and 2N HCl was added dropwise till gas evolution ceased (pH 5-6). The obtained suspension was concentrated at reduced pressure, and the residue was purified by flash chromatography (SiO₂) using as eluent a mixture DCM/MeOH=95/5. The pure intermediate (11) were obtained as colourless oil (0.49 g, yield 70%).

Example A.9

Preparation of

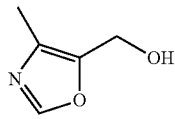

intermediate (12)

The suitable ethyl oxazole-5-carboxylate derivative (1.1 g, 7.09 mmol, 1 eq) was dissolved in EtOH (14 mL) and the mixture was cooled to 0° C. NaBH₄ (14.17 mmol, 2 eq) was added portionwise while stirring, and then the mixture was allowed to warm to r.t. After 2 hrs at reflux, the conversion was complete by TLC (95/5 DCM/MeOH). The mixture was cooled to 0° C. and 2N HCl was added dropwise till gas evolution ceased (pH 5-6). The obtained suspension was concentrated at reduced pressure, and the residue was purified by flash chromatography (SiO₂) using as eluent a mixture DCM/MeOH=95/5. The pure intermediate (12) was obtained as colourless oil (0.46 g, yield 58%).

Example A.10

Preparation of

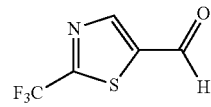

Intermediate (13)

Ethyl 2-(trifluoromethyl)thiazole-5-carboxylate (0.50 g, 2.22 mmol, 1 eq) was dissolved in dry DCM (11 mL) under argon atmosphere and cooled to −70° C. Then 1M DIBAL in DCM (2.5 mL, 2.49 mmol, 1.12 eq) was added dropwise over 10 minutes and the mixture stirred at the same temperature for 1.5 h. The reaction mixture was brought to 0° C., water (0.10 mL), 15% NaOH (0.10 mL) and a second portion of water (0.25 mL) were sequentially added and the mixture stirred until complete precipitation of the aluminium salt (5 minutes). The mixture was dried over anhydrous Na₂SO₄ and filtered. After solvent evaporation, the crude was purified by flash chromatography on direct phase (30/70 DCM/petroleum ether→100% DCM), giving pure intermediate (13) as a yellow oil (0.3 g, yield 75%).

Example A.11

Preparation of

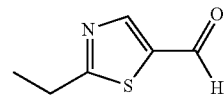

Intermediate (14)

2-Bromomalonaldehyde (0.71 g, 4,70 mmol, 1 eq) and propanethioamide (0.42 g, 4.71 mmol, 1 eq) were suspended in DCM (10 mL) and cooled to 0° C.; then DIPEA (0.82 mL, 4.71 mmol, 1 eq) was added in two portions. The resulting brown solution was left under stirring at room temperature for 2 days. Solvent was removed by evaporation, the brown residue was dissolved in Et₂O (20 mL), washed twice with NaHCO₃ sat. solution (20 mL) and brine (20 mL), dried over anh. Na₂SO₄, filtered, and finally evaporated. The crude was purified by flash chromatography on direct phase (20/80 EtOAc/petroleum ether), giving pure intermediate (14) as a brown oil (0.13 g, yield 20%).

Example A.12 a) Preparation of

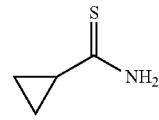

Intermediate (15a)

Cyclopropanecarboxamide (0.5 g, 5.87 mmol, 1 eq), sodium carbonate (0.62 g, 5.87 mmol, 1 eq) and Lawesson's reagent (2.37 g, 5.87 mmol, 1 eq) in THF (25 mL) were refluxed for 2.5 h. Solvent was removed in vacuo and the crude was partitioned between water (20mL) and diethyl ether (20 mL). The organic layer was dried over anh. Na$_2$SO$_4$, filtered and finally evaporated, giving intermediate (15a) as a white solid (0.44 g, yield 74%).

b) Preparation of

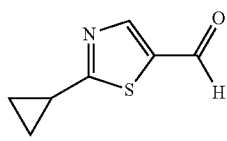

Intermediate (15b)

2-Bromomalonaldehyde (0.66 g, 4,35 mmol, 1 eq) dissolved in dry THF (2 mL) was added to a solution of intermediate 15a (0.44 g, 4.35 mmol, 1 eq) in dry DCM (10 mL). The mixture was cooled to −15° C.; then DIPEA (0.76 mL, 4.35 mmol, 1 eq) was added portionwise. The resulting yellow solution was left under stirring at room temperature for 4 days. Solvent was removed by evaporation, the brown residue was dissolved in Et$_2$O (20 mL), washed twice with NaHCO$_3$ sat. solution (20 mL) and brine (20 mL), dried over anh. Na$_2$SO$_4$, filtered, and finally evaporated. The crude was purified by flash chromatography on direct phase (10/90 EtOAc/petroleum ether), giving pure intermediate (15b) as a brown oil (0.25 g, yield 38%).

Example A.13 c) Preparation of

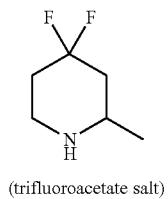

Intermediate (16)

(trifluoroacetate salt)

A solution of 1-boc-2-methylpiperidin-4-one (0.55 g, 2.6 mmol, 1 eq) in dry DCM (7.5 mL) was cooled at 0° C. and DAST (0.68 mL, 5.2 mmol, 2 eq) was added dropwise. The reaction was stirred overnight at 10° C., then diluted with DCM (10 mL), washed with NaHCO$_3$ sat. solution (10 mL), 5% citric acid solution in water (10 mL) and finally with brine (10 mL). The organic layer was dried over anh. Na$_2$SO$_4$, filtered and evaporated. The residue was purified by flash chromatography on silica gel (eluent 10/90 EtOAc/petroleum ether) affording 0.53 g of pure 1-N-boc-4,4-difluoromethylpiperidine as white solid.

TFA (2 mL, 26 mmol, 10 eq) was added under stirring to a solution of 1-N-boc-4,4-difluoromethylpiperidine (0.53 g, 2.25 mmol) in DCM (8 mL), cooled with an ice bath. The reaction mixture was allowed to warm at room temperature and stirred for additional 30 minutes. Solvent was removed at reduced pressure, affording 0.73 g (70% yield over two steps) of intermediate 16 as a TFA salt.

Example A.14 a) Preparation of

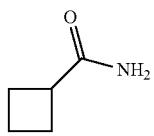

Intermediate (17a)

A solution of ciclobutanecarboxylic acid 1.91 mL, 16.6 mmol, 1 eq) in dry THF was treated with thionyl chloride (4 mL, 50 mmol, 3 eq) and refluxed for 2 h. The reaction mixture was cooled to room temperature, diluted with DCM (5 mL) and evaporated at reduced pressure. The residue was dissolved in acetonitrile (31 mL), added dropwise to a stirred solution of ammonium hydroxide (59 mL) at 0° C. and stirred at this temperature for 1 h. Then, the reaction mixture was poured into a separating funnel and extracted with EtOAc (15 mL×2). The combined organic extracts were washed with 0.1M HCl acq. solution (20 mL), water (20 mL) and brine (20 mL), dried over anh. Na$_2$SO$_4$, filtered and finally evaporated, yielding intermediate 17a (0.31 g, yield 16%) as a white solid.

b) Preparation of

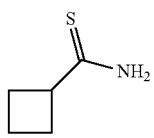

Intermediate (17b)

Intermediate 17a (0.31 g, 3.17 mmol, 1 eq), sodium carbonate (0.34 g, 3.17 mmol, 1 eq) and Lawesson's reagent (1.38 g, 3.17 mmol, 1 eq) in THF (16 mL) was refluxed for 3 h. Solvent was removed in vacuo and the crude was partitioned between water (20 mL) and diethyl ether (20 mL). The organic layer was dried over anh. Na$_2$SO$_4$, filtered and finally evaporated, giving intermediate (17b) as a yellow liquid (0.36 g, yield 99%).

c) Preparation of

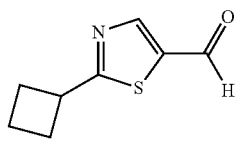

Intermediate (17c)

2-Bromomalonaldehyde (0.51 g, 3.15 mmol, 1 eq) dissolved in dry THF (5 mL) was added to a solution of intermediate 19 (0.36 g, 3.15 mmol, 1 eq) in dry DCM (8 mL). The mixture was cooled to −15° C., then DIPEA (0.55 mL, 3.15 mmol, 1 eq) was added portionwise under Ar atmosphere. The resulting brown solution was left under stirring at room temperature for 2 days. Solvent was removed by evaporation, the brown residue was dissolved in Et$_2$O (20 mL), washed twice with NaHCO$_3$ sat. solution (20 mL) and brine (20 mL), dried over anh. Na$_2$SO$_4$, filtered, and finally evaporated. The crude was purified by flash

Example A.15 a) Preparation of

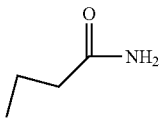

Intermediate (18a)

28% ammonium hydroxide solution in water (31 mL) was added to a stirred solution of butyryl chloride (0.97 mL, 9.3 mmol, 1 eq) in acetonitrile (15.5 mL) at 0° C. After 15 min, the reaction mixture was poured into a separating funnel and extracted with EtOAc (30 mL×3). The combined organic extract were washed with 0.1 M HCl acq. solution (20 mL), water (20 mL) and brine (20 mL), dried over anh. Na$_2$SO$_4$, filtered and finally evaporated, giving intermediate 18a (0.32 g, yield 40%) as a white solid.

b) Preparation of

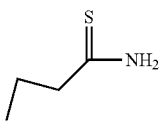

Intermediate (18b)

Intermediate 18a (1.24 g, 14 mmol, 1 eq), sodium carbonate (1.48 g, 14 mmol, 1 eq) and Lawesson's reagent (5.66 g, 14 mmol, 1 eq) in THF (17 mL) were refluxed for 3 h. Solvent was removed in vacuo and the crude was partitioned between water (20 mL) and diethyl ether (20 mL). The organic layer was dried over anh. Na$_2$SO$_4$, filtered and finally evaporated, giving intermediate 18b as a yellow liquid (1.23 g, yield 89%).

c) Preparation of

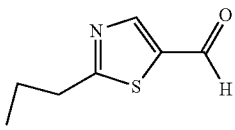

Intermediate (18c)

2-Bromomalonaldehyde (1.88 g, 12 mmol, 1 eq) dissolved in dry THF (15 mL) was added to a solution of intermediate 18b (1.23 g, 12 mmol, 1 eq) in dry DCM (30 mL). The mixture was cooled to −15° C.; then DIPEA (2.16 mL, 12 mmol, 1 eq) was added portionwise under Ar atmosphere. The resulting brown solution was left under stirring at room temperature for 3 days. Solvent was removed by evaporation, the brown residue was dissolved in Et$_2$O (20 mL), washed twice with NaHCO$_3$ sat. solution (20 mL) and brine (20 mL), dried over anh. Na$_2$SO$_4$, filtered, and finally evaporated. The crude was purified by flash chromatography on direct phase (20/80 EtOAc/petroleum ether), giving pure intermediate 18c as a yellow liquid (0.46 g, yield 25%).

Example A.16 a) Preparation of

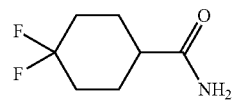

Intermediate (19a)

4,4-difluorocyclopropanecarboxylic acid (1 g, 6.09 mmol, 1 eq) was dissolved in dry THF (37 mL), cooled to −70° C. and treated with 4-methylmorpholine (0.67 mL, 6.09 mmol, 1 eq) under Ar atmosphere. Then butylchloroformate (0.79 mL, 6.09 mmol, 1 eq) was added dropwise at −70° C. After 15 min, 28% ammonium hydroxide solution in water (7.4 mL) was added and the reaction mixture heated to room temperature. Solvent was removed under reduced pressure, the residue dissolved in EtOAc, washed with water (20 mL), dried over anh. Na$_2$SO$_4$, filtered and finally evaporated, giving intermediate 19a (0.86 g, yield 86%) as a white solid.

b) Preparation of

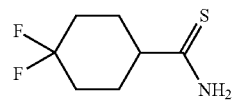

Intermediate (19b)

Intermediate 19a (0.86 g, 5.29 mmol, 1 eq), sodium carbonate (0.56 g, 5.29 mmol, 1 eq) and Lawesson's reagent (2.14 g, 5.29 mmol, 1 eq) in THF (26 mL) were refluxed for 3 h. Solvent was removed in vacuo and the crude was partitioned between water (20 mL) and diethyl ether (20 mL). The organic layer was dried over anh. Na$_2$SO$_4$, filtered and finally evaporated, giving intermediate 19b as an off-white solid (1.09 g, yield 99%).

c) Preparation of

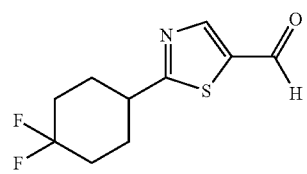

Intermediate (19c)

2-Bromomalonaldehyde (0.97 g, 6.11 mmol, 1 eq) dissolved in dry THF (10 mL) was added to a solution of intermediate 19b (1.09 g, 6.11 mmol, 1 eq) in dry DCM (15 mL). The mixture was cooled to −15° C., then DIPEA (1.06 mL, 6.11 mmol, 1 eq) was added portionwise under Ar atmosphere. The resulting brown solution was left under stirring at room temperature for 1 days. Solvent was removed by evaporation, the brown residue was dissolved in Et$_2$O (20 mL), washed twice with NaHCO$_3$ sat. solution (20 mL) and brine (20 mL), dried over anh. Na$_2$SO$_4$, filtered, and finally evaporated. The crude was purified by flash chromatography on direct phase (30/70 EtOAc/petroleum ether), giving pure intermediate 19c as a colorless liquid (0.34 g, yield 24%).

--- chromatography on direct phase (20/80 EtOAc/petroleum ether), giving pure intermediate (17c as a yellow liquid (0.13 g, yield 26%).

Example A.17 a) Preparation of

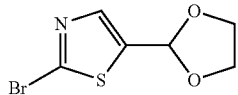
Intermediate (20a)

A mixture of 2-bromo-5-formyl-1,3-thiazole (0.384 g, 2 mmol, 1 eq), p-toluensulfonic acid (0.031 g, 0.16 mmol, 0.08 eq) and ethylenglycol (0.334 mL, 6 mmol, 3 eq) in dry toluene (12 mL) was refluxed using a Dean-Stark apparatus for 3 h. Then the solvent was removed and the residue purified by flash chromatography over silica gel (100% Petroleum ether→20/80 EtOAc/Petroleum ether), yielding intermediate 20a (0.33 g, yield 70%) as a colourless oil.

b) Preparation of

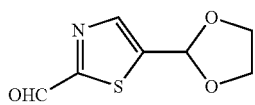
Intermediate (20b)

Intermediate 20a (0.33 g, 1.4 mmol, 1 eq) was dissolved in dry THF (2mL) and cooled to −70° C. Then a 1.6M n-BuLi solution in hexane (0.96 mL, 1.54 mmol, 1.1 eq) was added dropwise under Ar atmosphere. After 50 minutes, DMF (0.08 mL, 3 mmol, 1.6 eq) was added dropwise at −70° C. and the reaction stirred at this temperature for 50 min. Then NH$_4$Cl (aq. saturated solution, 10 mL) was added and the reaction warmed to room temperature. The reaction mixture was then extracted with DCM (20 mL×2). The combined organic extracts were dried over anh. Na$_2$SO$_4$, filtered and evaporated yielding intermediate 20b (0.225 g, yield 87%) as anorange oil.

c) Preparation of

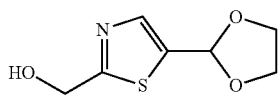
Intermediate (20c)

Sodium borohydride (0.046 g, 1.215 mmol, 1 eq) was added portionwise to a stirred solution of intermediate 20b (0.225 g, 1.25 mmol, 1 eq) in methanol (2 mL), at 0° C. and under nitrogen atmosphere. The reaction was stirred for 30 min at 0° C., then the solvent was evaporated at reduced pressure. The residue was partitioned between 2/1 EtOAc/DCM (10 mL) and water (10 mL), the organic layer dried over anh. Na$_2$SO$_4$, filtered and evaporated, yielding intermediate 20c (0.19 g, yield 84%) as an orange oil.

c) Preparation of

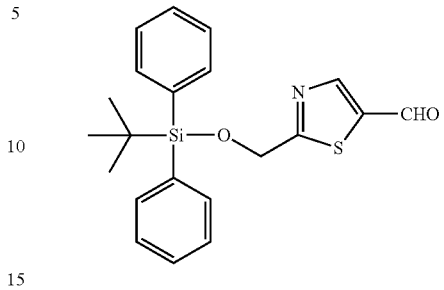
Intermediate (20d)

tert-butyldiphenylsilylchloride (0.30 g, 1.01 mmol, 1.1 eq) was added at 0° C. under nitrogen atmosphere to a magnetically stirred solution of intermediate 20c (0.19 g, 1 mmol, 1 eq) and imidazole (0.072 g, 1.05 mmol, 1.05 eq) in dry DCM (1.5 mL). After 2 h the reaction was warmed to room temperature and poured into NaHCO$_3$ sat. solution (5 mL). The organic layer was dried over anh. Na$_2$SO$_4$, filtered and evaporated. The residue (0.47 g) was dissolved in THF (10 mL) and treated with 5N HCl (3 mL) at room temperature. After 2 h, the reaction mixture was basified with NaHCO$_3$ sat. solution (3 mL) and extracted with DCM (10 mL×2). The combined organic extracts were dried over anh. Na$_2$SO$_4$, filtered and evaporated, yielding intermediate 20d (0.194 g, yield 51%) as a colourless oil.

Example A.18 a) Preparation of

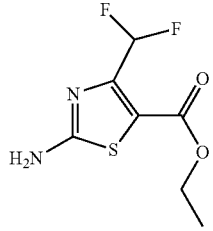
Intermediate (21a)

Sulfuryl chloride (1.23 mL, 15.2 mmol, 1.01 eq) was added dropwise at 0° C. to ethyl 4,4-difluoroacetoacetate (2.5 g, 15.0 mmol, 1 eq) under nitrogen atmosphere, and stirred overnight at room temperature. The reaction was diluted with EtOAc (20 mL) and poured into an ice/water mixture (20 mL). The organic layer was dried over anh. Na$_2$SO$_4$, filtered and evaporated giving 3.2 g of crude in 2-chloro-4,4-difluoroacetoacetate as a yellow oil. The crude was dissolved in ethanol (10 mL), treated with thiourea (3.2 g, 30 mmol, 2 eq) and heated in a microwave reactor for 1 h at 101° C. Then, the solvent was removed in vacuo and the residue partitioned in sat. NaHCO$_3$ (10 mL) and EtOAc (10 mL). The organic layer was washed with brine (20 mL), dried over anh. Na$_2$SO$_4$, filtered and evaporated. The crude was treated with diethyl ether, filtered and dried in vacuo, giving 1.37 g (yield 41%) of intermediate 21a as a yellow solid.

b) Preparation of

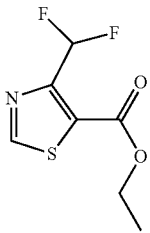

Intermediate (21b)

Intermediate 21a (1.37 g, 6.16 mmol, 1 eq) was dissolved in dioxane (35 mL), isoamylnitrite (2.24 mL, 16.64 mmol, 2.7 eq) was added and the reaction mixture was heated for 1 hour at 80° C. Solvent was removed by evaporation under reduced pressure, and the residue was purified by flash chromatography over silica gel (EtOAc/petroleum ether 10/90) yielding intermediate 21b (1.02 g, yield 80%) as a yellow solid.

c) Preparation of

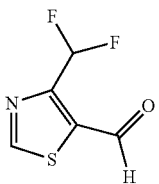

Intermediate (21c)

Intermediate 21b (0.758 g, 3.66 mmol, 1 eq) was dissolved in dry DCM (18.5 mL) under argon atmosphere and cooled to −75° C. 1M diisobutyl aluminium hydride in DCM (4.1 mL, 4.1 mmol, 1.12 eq) was added dropwise and the reaction mixture was stirred at −70° C. After 1.5 h, 1M diisobutyl aluminium hydride in DCM (2.5 mL, 2.5 mmol, 0.68 eq) was added dropwise and the reaction mixture was stirred additionally for 1 h at −70°. The reaction was warmed to 0° C. and treated with water (0.264 mL), 15% NaOH (0.264 mL) and water (0.66 mL) in this order. It was then stirred for 5 minutes at 0° C., then for 30 minutes at room temperature. Water (0.24 mL) followed by 15% NaOH (0.130 mL) were sequentially added, and the reaction was stirred at room temperature until a precipitate was formed. The mixture was filtered and then the solvent was concentrated. The residue was purified by flash chromatography over silica gel (DCM/petroleum ether 80/20→100% DCM) yielding a yellow oil (0.34 mg, yield 40%) containing intermediate 21c (purity ≈70%), that was used as such.

Example A.19

General Procedure for Thiazole Intermediates
Step a) Preparation of α-Aminonitriles
Method a1)

An aldehyde (2.21 mmol, 1 eq) was dissolved in glacial AcOH (6.8 mL). AcONa (3.315 mmol, 1.5 eq) and an amine (2.652 mmol, 1.2 eq) were sequentially added stirring at room temperature under $N_2$. The yellow solution was stirred for 1 hr and then was cooled to 0° C. TMSCN (4.42 mmol, 2 eq) was added dropwise and the mixture was allowed to warm to room temperature. In the following hours, if necessary, 1 equivalent of TMSCN (1.1 mmol×2) was added in two portions. When the conversion was complete by UPLC-MS, water (5 mL) was added and the solution was evaporated. A saturated solution of $NaHCO_3$ (20 mL) was added to the residue and the mixture was extracted with DCM (15 mL×3). The combined organic phases were dried (anh. $Na_2SO_4$) and evaporated. The crude was purified by flash chromatography ($SiO_2$) with petroleum ether/AcOEt giving the pure α-aminonitrile (65% average yield).

Using Method a1, A0013_15_01 (yield 59%), A0013_24_01 (yield 60%), A0011_48_01 (yield 71%) were prepared starting from 2-thiazolecarboxaldehyde and 1,2,3,4-tetrahydroisoquinoline, 4,4-difluoropiperidine hydrochloride and morpholine respectively; intermediates A0013_23_01 (yield 60%), A0015_24_01 (yield 61%) were prepared starting from 4-thiazol-carbaldehyde and 4,4-difluoropiperidine, homomorpholine hydrochloride respectively; intermediates A0015_04_01 (yield 65%), A0013_41_01 (yield 83%), A0013_41_02 (yield 50%), A0013_83_01 (yield 64%), A0015_85_01 (yield 79%), A0016_13_01 (yield 74.5%), were prepared starting from 5-thiazol-carbaldehyde and morpholine, 4,4-difluoropiperidine hydrochloride, 1,2,3,4-tetrahydroisoquinoline, intermediate (10), intermediate (9) and piperidine respectively; intermediates A0015_48_01 (yield 50%), A0015_47_01 (yield 85%), A0015_4601 (yield 22%), A0018_42_01 (yield 83%), A0018_41_01 (yield 90%), A0017_69_01 (yield 72%) and A0017_70_01 (yield 81%) were prepared starting from thiazol-4-methyl-5-yl carbaldehyde and 1,2,3,4-tetrahydroisoquinoline, 4,4-difluoropiperidine hydrochloride, morpholine, intermediate (10), intermediate (9), 3,3-difluoropiperidine hydrochloride and 3,3-difluoroazetidine hydrochloride respectively; intermediate A0012_57_01 (yield 79%), A0012_58_01 (yield 69%) and A0018_14_01 (yield 73%) were prepared starting from intermediate (1) and 4,4-difluoropiperidine hydrochloride, 1,2,3,4-tetrahydroisoquinoline and intermediate (10); intermediate A0018_57_01 was prepared starting from intermediate (2b) and 4,4-difluoropiperidine hydrochloride; intermediate A0018_72_01 was obtained starting from intermediate (3d) and 4,4-difluoropiperidine hydrochloride; intermediate A0018_91_01 (yield 71%) was obtained starting from intermediate (13) and 4,4-difluoropiperidine hydrochloride; intermediate A0020_17_01 (yield 84%) was obtained starting from intermediate (14) and 4,4-difluoropiperidine hydrochloride; intermediate A0020_25_01 (yield 67%) was obtained starting from intermediate (15b) and 4,4-difluoropiperidine hydrochloride; intermediate A0020_10_02 (yield 45%) was obtained starting from intermediate (1) and homomorpholine hyrdochloride; intermediate A0021_05_01 (yield 81%) was obtained starting from 4-methyl-5-thiazolecarboxaldehyde and 2-[2-(trifluoromethyl)phenyl]morpholine; intermediate A0021_06_02 (yield 87%) was obtained starting from 4-methyl-5-thiazolecarboxaldehyde and 2-(2,4-difluorophenyl) morpholine; intermediate A0021_06_04 (yield 95%) was obtained starting from 4-methyl-5-thiazolecarboxaldehyde and 2-(1-methyl-1H-pyrazol-4-yl)morpholine; intermediate A0021_06_03 (yield 77%) was prepared staring from methyl-5-thiazolecarboxaldehyde and 5-oxa-8-azaspiro[3.5]nonane; intermediate A0020_33_01 (yield 61%) was prepared starting from methyl-5-thiazolecarboxaldehyde and intermediate 16; intermediate A0016_39_01 (yield 72%) was prepared starting from intermediate 17c and 4,4-difluoropiperidine hydrochloride; intermediate A0016_40_01 (yield 64%) was prepared starting from intermediate 18c and 4,4-difluoropiperidine hydrochloride; intermediate A0017_98_01 (yield 19%) was obtained starting from intermediate 1 and intermediate 16; A0016_46_01

(yield 51%) was obtained starting from intermediate 19c and morpholine; A0016_45_01 (yield 45%) was obtained starting from intermediate 19c and 4,4-difluoropiperidine hydrochloride; intermediate A0020_60_01 (yield 42%) was prepared starting from intermediate 20d and 4,4-difluoropiperidine hydrochloride; A0018_98_01 (yield 39%) was obtained starting from intermediate 21c and 4,4-difluoropiperidine hydrochloride; A0016_55_05 (yield 67%) was obtained starting from 2-tert-butyl-1,3-thiazole-5-carbaldehyde and 4,4-difluoropiperidine hydrochloride; A0021_41_01(yield 79%) was obtained starting from 4-cyclopropyl-1,3-thiazole-5-carbaldehyde and 4,4-difluoropiperidine hydrochloride. A0016_96_01 (yield 58%) was prepared starting from intermediate 21c and morpholine.

A0013_15_01

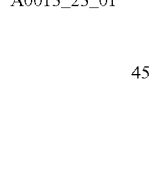

A0013_24_01

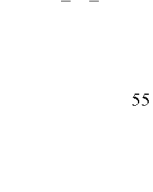

A0011_48_01

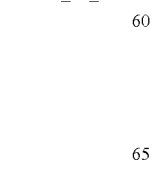

A0013_23_01

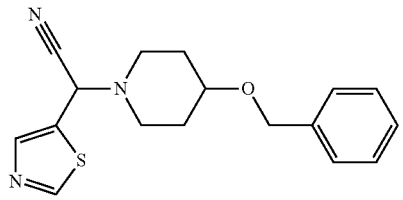

A0015_24_01

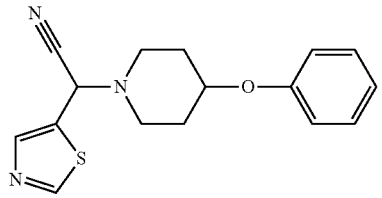

A0015_04_01

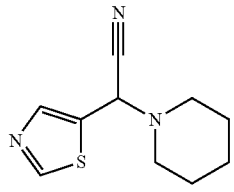

A0013_41_01

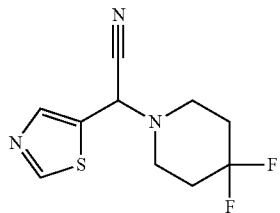

A0013_41_02

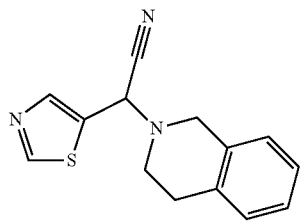

A0013_83_01

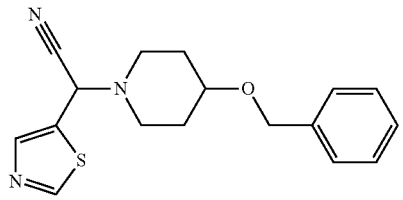

A0015_85_01

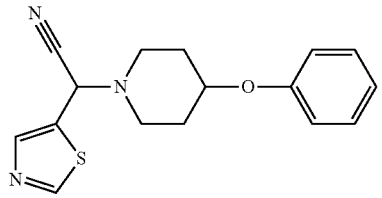

A0016_13_01

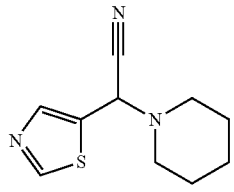

A0015_48_01

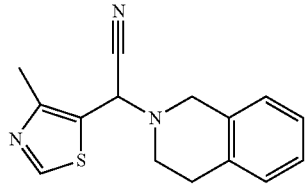

A0015_47_01

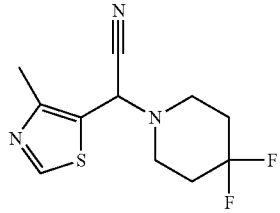

-continued
A0015_46_01
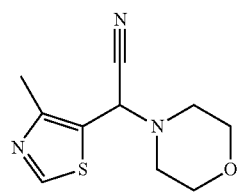
A0018_42_01
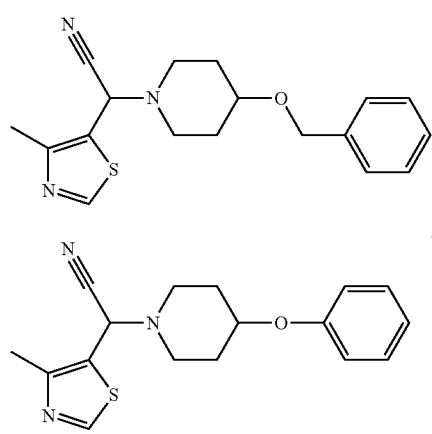
A0018_41_01
A0017_69_01
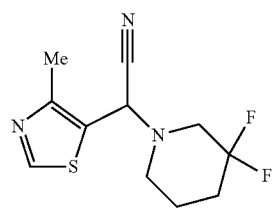
A0017_70_01
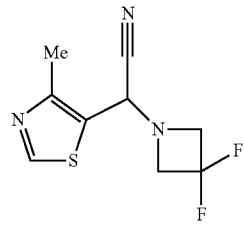
A0012_57_01
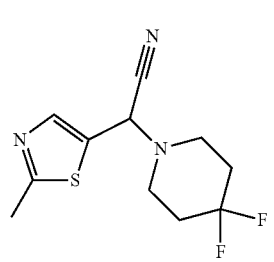
A0012_58_01
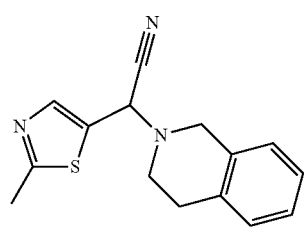
-continued
A0018_14_01
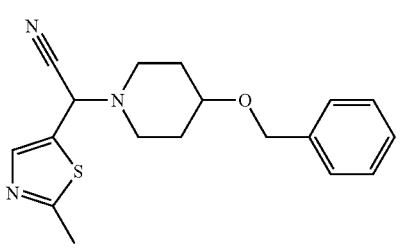
A0018_57_01
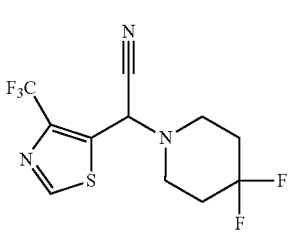
A0018_72_01
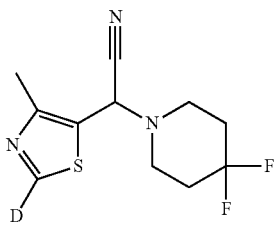
A0018_91_01
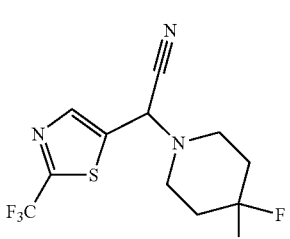
A0020_17_01
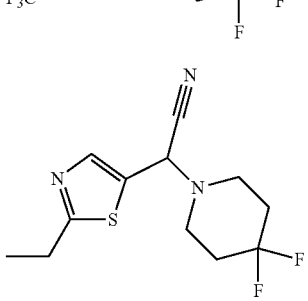
A0020_25_01
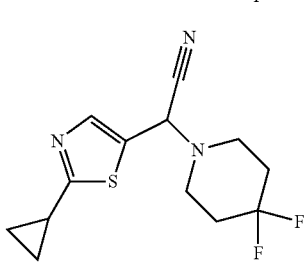
A0020_10_01
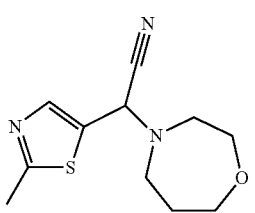

A0021_05_01
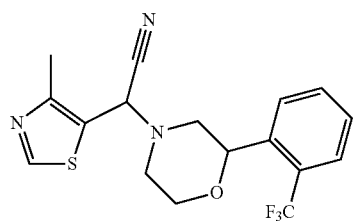
A0021_06_02
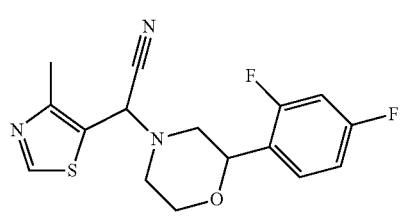
A0021_06_04
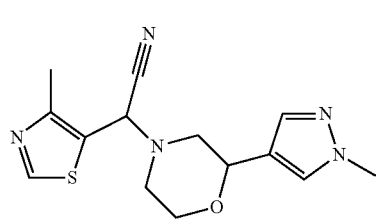
A0021_06_03
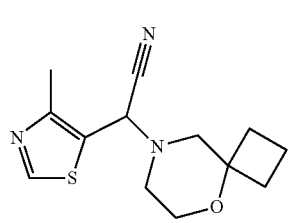
A0016_39_01
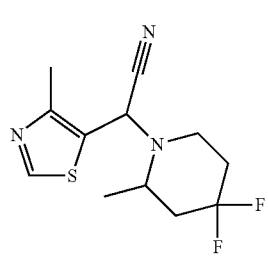
A0016_40_01
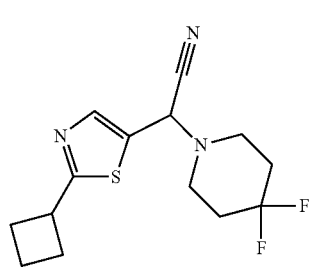
A0017_98_01
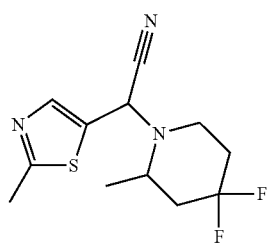
A0016_46_01
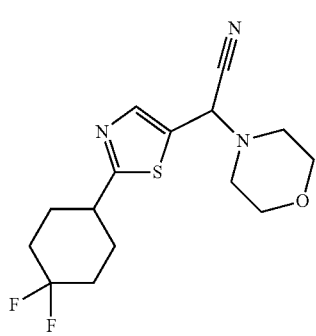
A0016_45_01
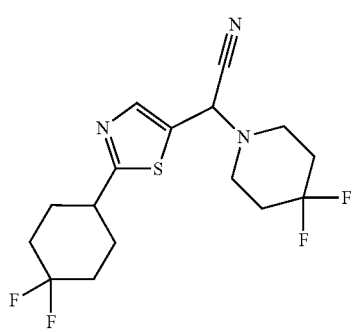
A0020_60_01
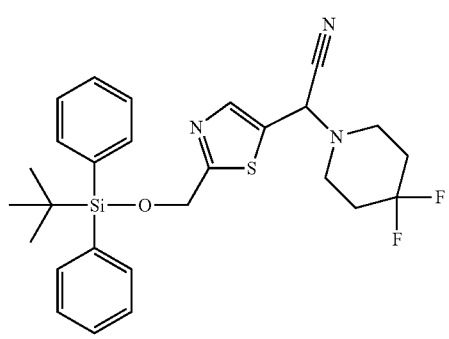
A0018_98_01
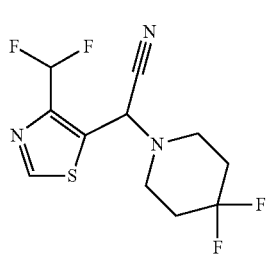

-continued

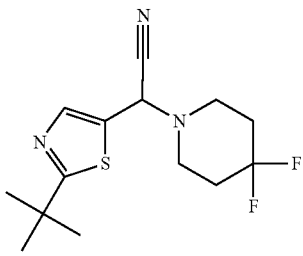
A0016_55_05

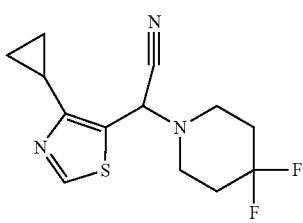
A0021_41_01

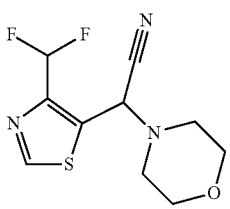
A0016_96_01

Method a2)

An aldehyde (1.33 mmol, 1 eq) was dissolved in dry MeCN (3 mL) and glacial AcOH (≈10 drops) was added at room temperature under nitrogen atmosphere. After 10 minutes, an amine (1.33 mmol, 1 eq) was added dropwise, and the resulting orange solution was stirred at room temperature for 30 minutes. The mixture was then cooled to 0° C. with an ice bath and TMSCN (2 mmol, 1.5 eq) was added dropwise. Stirring was continued at room temperature until complete conversion of the aldehyde (typically ≈1.5 h). The reaction was quenched with a $NaHCO_3$ sat. aqueous solution, and the solvent was removed in vacuo. The resulting aqueous mixture was extracted with DCM (20 mL×3) and the combined organic phases were dried over anh. $Na_2SO_4$, filtered and evaporated. Finally, the residue was purified by flash chromatography over silica gel (eluent 50/50 petroleum ether/EtOAc), giving the pure α-aminonitriles.

Using Method a2, intermediate A0015_02_01 (yield 67%), was prepared starting from 4-thiazol-carbaldehyde and morpholine. Similarly, A0015_01_01 (yield 53%) was prepared starting from 4-thiazole-carbaldehyde and 1,2,3,4-tetrahydroisoquinoline.

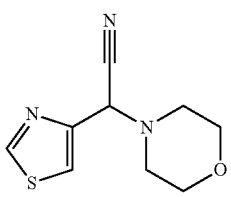
A0015_02_01

-continued

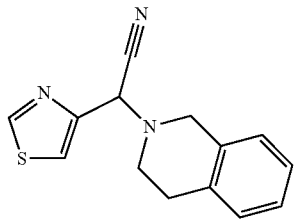
A0015_01_01

Step b) Preparation of Diamines
Method b1)

An α-aminonitrile (0.478 mmol, 1 eq) was dissolved in 3M $NH_3$ in MeOH (16 mL, 100 eq) and the solution was hydrogenated in an H-Cube™ continuous flow apparatus with a Ni-Raney cartridge (55 mm long CatCart), using a 0.7 mL/min flow. The hydrogen pressure was variable between 30 to 60 bar and the temperature from 30° C. to 40° C., depending on the substrate. After an appropriate reaction time (generally 2 h), the solution was evaporated giving the primary amine that was used as such in the next step, without any purification (65% average yield).

Using Method b1, intermediate A0013_31_01 (yield 91%) were prepared starting from A0015_02_01; intermediate A0015_11_01 (yield 34%) was prepared starting from A0015_01_01; intermediate A0015_25_01 (yield 27%) was prepared starting from A0015_24_01; intermediate A0013_30_01 (yield 64%) was prepared starting from A0013_23_01; intermediate A0013_33_01 (yield55%) was prepared starting from A0013_41_02; intermediate A0013_40_01 (yield 41%) was prepared starting from A0015_04_01; intermediate A0013_54_03 (yield 65%) was prepared starting from A0013_41_01; intermediate A0017_01_01 (yield 45%) was prepared starting from A0013_83_01; intermediate A0016_09_01 (yield 39%) was prepared starting from A0015_85_01; intermediate A0016_17_01 (yield 9%) was prepared starting from A0016_13_01; intermediate A0015_52_01 (yield 50%) was prepared starting from A0015_48_01; intermediate A0015_56_01 (yield 76%) was prepared starting from A0015_47_01; intermediate A0015_54_01 (yield 75%) was prepared starting from A0015_46_01; intermediate A0017_59_01 (yield 84%) was prepared starting from A0018_42_01; intermediate A0017_58_01 (yield 76%) was prepared starting from A0018_41_01; intermediate A0017_73_01 (yield 88%) was prepared starting from A0017_69_01; intermediate A0017_72_01 (yield 86%) was prepared starting from A0017_70_01; intermediate A0018_58_01 (yield 81%) was prepared starting from A0018_57_01; intermediate A0018_75_01 (Yield 77%) was prepared starting from A0018_72_1; intermediate A0021_07_01 (yield 91%) was prepared starting from A0021_05_01; intermediate A0021_07_02 (yield 74%) was prepared starting from A0021_06_02; intermediate A0021_07_04 (yield 52%) was prepared starting from A0021_06_04; intermediate A0021_07_03 (yield 33%) was prepared staring from A0021_06_03; A0020_66_01 (yield 81%) was prepared starting from A0016_39_01; A0020_69_01 (yield 70%) was prepared starting from A0016_40_01; A0016_48_01 (yield: 81%) was prepared starting from A0016_46_01; A0016_47_01 (yield 66%) was prepared starting from A0016_45_01; A0020_63_01 (yield 86%) was prepared starting from A0020_60_01; A0016_59_01 (yield 88%) was prepared starting from A0016_55_05.

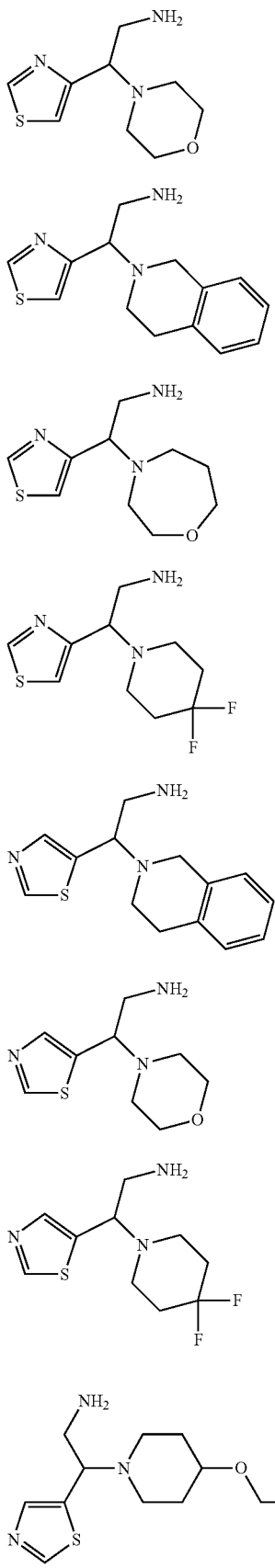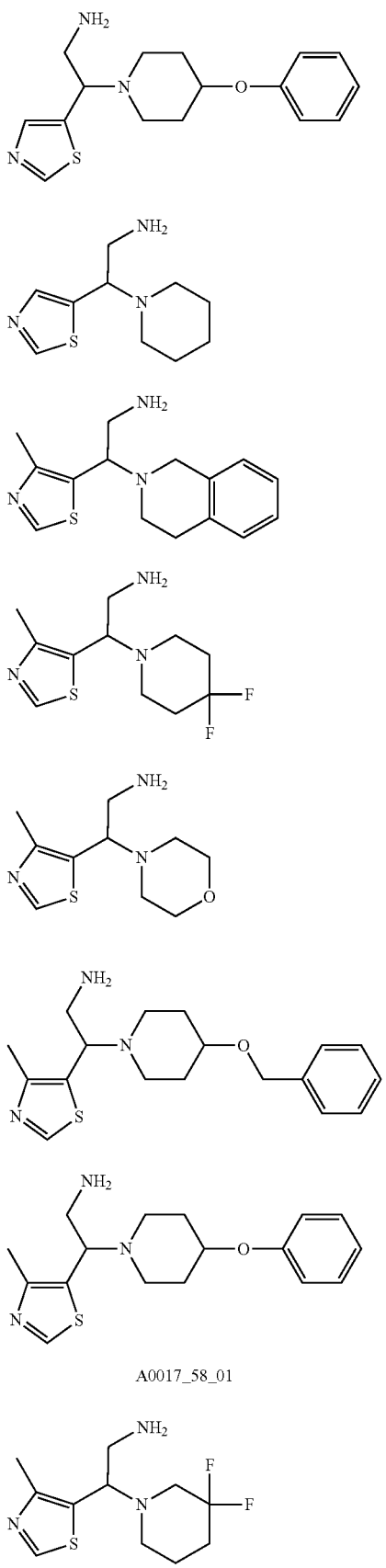

-continued
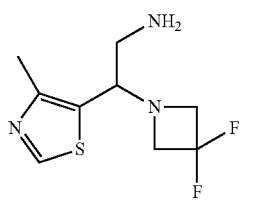
A0017_72_01
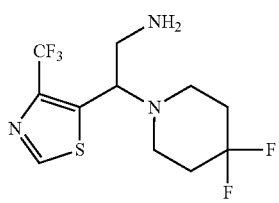
A0018_58_01
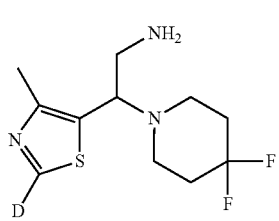
A0018_75_01
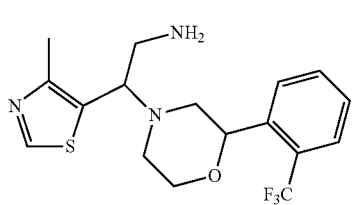
A0021_07_01
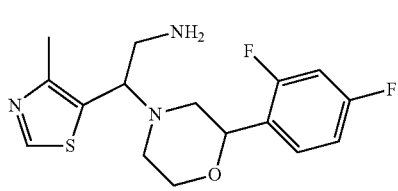
A0021_07_02
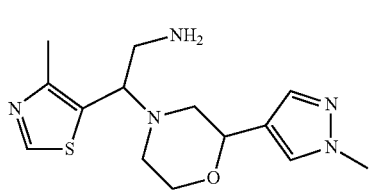
A0021_07_04
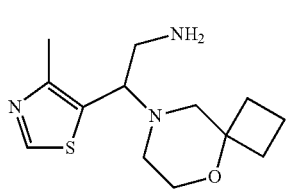
A0021_07_03
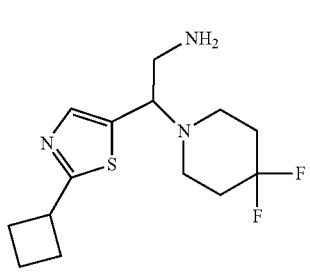
A0020_66_01
-continued
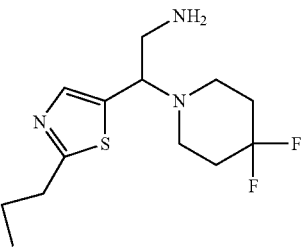
A0020_69_01
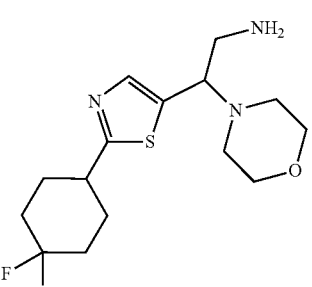
A0016_48_01
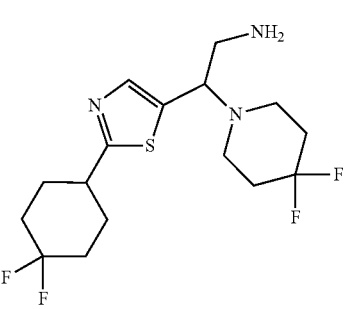
A0016_47_01
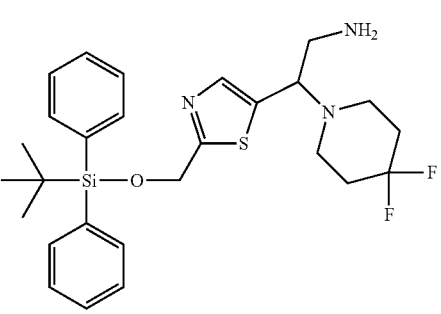
A0020_63_01
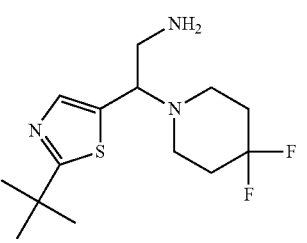
A0016_59_01
Method b2)
Method b2 Consists of a Two-Step Procedure:
Step b2-1
An α-aminonitrile (1 eq), Boc$_2$O (2 eq) and nickel(II) chloride hexahydrate (0.05 eq) were taken up in dry methanol (0.75 mL) and cooled to 0° C. Sodium borohydride (7 eq) was then added portion-wise over 45 minutes while stirring. The reaction mixture was stirred 3 h before ethylenediamine (3 eq) was added and the reaction mixture was allowed to return to room temp. After an additional 0.5 h of stirring, the solvent was removed in vacuo and the resulting solid was taken up with saturated aqueous sodium bicarbonate (10 mL) and EtOAc (10 mL). The organic layer was washed with brine and dried (Na$_2$SO$_4$). The resulting N-Boc-α-aminonitrile was purified by flash chromatography on silica gel.

Using the procedure described in Step b2-1, intermediate A0013_16_01 (yield 35%) was prepared starting from A0013_15_01; intermediate A0013_26_01 (yield 28%) was prepared strarting from A0013_24_01; intermediate A0011_52_01 (yield 51%) was prepared starting from A0011_48_01.

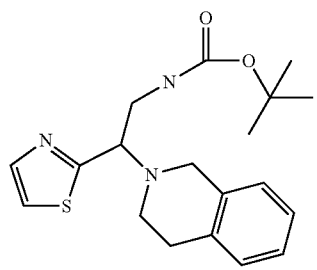

A0013_16_01

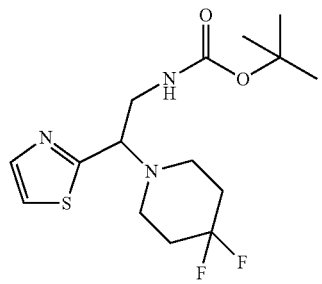

A0013_26_01

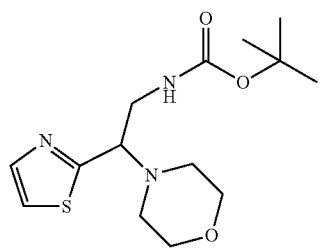

A0011_52_01

Step b2

An N-Boc-α-aminonitrile was dissolved in 1/1 DCM/TFA (1-2 mL) and stirred at room temperature until reaction completion. Then the solvent was removed in vacuo to afford the pure α-aminonitrile as its TFA salt that was used in the next synthetic steps without any purification.

Using the procedure described in Step b2-2, intermediate A0013_28_01 was prepared starting from A0013_16_01; intermediate A0013_28_03 was prepared starting from A0013_26_01; intermediate A0011_54_01 was prepared starting from A0011_52_01.

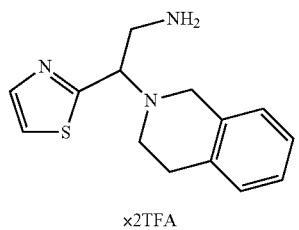

A0013_28_01 x2TFA

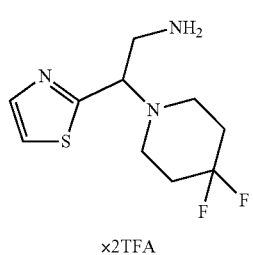

A0013_28_03 x2TFA

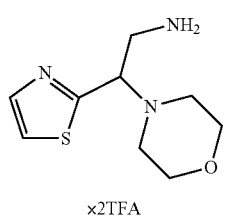

A0011_54_01 x2TFA

Method b3)

An α-aminonitrile (1 eq), was dissolved in dry THF, under nitrogen atmosphere and the solution was cooled to 0° C. with an ice bath. A 1M LiAlH$_4$ suspension in dry THF (1 eq) was dropwise added and the reaction mixture stirred for 30 min at 0° C. This procedure was repeated (typically 3 times) until complete nitrile comsumption, observed by TLC. The reaction was quenched by slow addiction of MeOH at 0° C., until complete gas evolution. The mixture was evaporated and the crude was purified by flash chromatography on silica gel (eluent DCM/MeOH/NH$_4$OH) giving the pure α-aminonitrile as an oil.

Using Method b3, intermediate A0012_61_02 (yield 45%) was prepared starting from A0012_57_01; intermediate A0012_63_01 (yield 45%) was prepared starting from A0012_58_01; intermediate A0018_16_01 (yield 42%) was prepared starting from A0018_14_01; intermediate A0018_93_01 (yield 14%) was prepared starting from A0018_91_01; intermediate A0020_19_01 (yield 41%) was prepared starting from A0020_17_01; intermediate A0020_26_01 (yield 42%) was prepared staring from A0020_25_01; intermediate A0020_37_01 (yield 49%) was prepared starting from A0020_10_02; A0020_38_01 (yield 38%) was obtained starting from A0020_33_01; A0020_31_01 (yield 50%) was obtained starting from A0017_98_01; A0016_57_01 (yield 40%) was obtained starting from A0021_41_01.

A0012_61_02

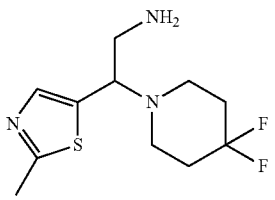

A0012_63_01

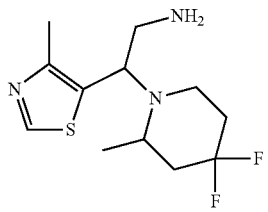
A0020_38_01

A0018_16_01

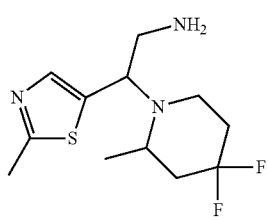
A0020_31_01

A0018_93_01

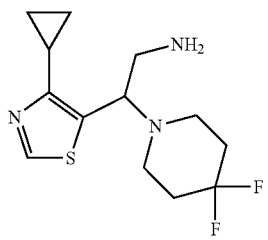
A0016_57_01

A0020_19_01

Method b4)
Preparation of

A0020_26_01

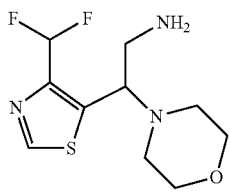
intermediate A0022_01_01

A0020_37_01

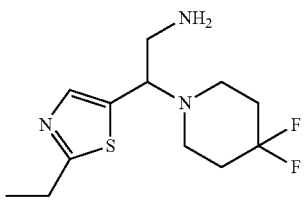

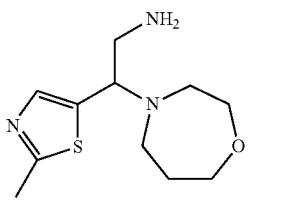

A0016_96_01 (0.10 g, 0.405 mmol) was dissolved in dry DCM (4 mL) under nitrogen atmosphere and the solution was cooled to 0° C. (1M) DIBAL-H in DCM (1.6 mL, 1.62 mmol, 4 eq) was dropwise added at the same temperature and the reaction was stirred for 30min. The reaction was stopped by addiction of (1M) HCl in MeOH (3 mL), filtered and solvents were removed in vacuo. The residue was dissolved in NaHCO$_3$ satured solution (10 mL) and extracted with DCM (10 mL×3) and EtOac (10 mL×3). The combined organic extracts were dried over anh. Na$_2$SO$_4$, filtered and evaporated yielding A0022_01_01 (0.069 g, yield 65%) as brown solid.

Example A.20

Preparation of intermediate A0016_17_01

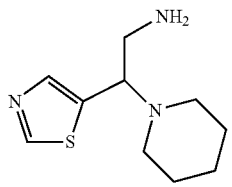

Intermediate A0016_13_01 (0.235 g, 1.134 mmol, 1 eq) was dissolved in MeOH (11 mL) and the colourless solution was cooled to 0° C. with an ice bath. $CoCl_2.6H_2O$ (405 mg, 1.7 mmol, 1.5 eq) was added and a violet solution was obtained. Then $NaBH_4$ (0.214 g, 5.67 mmol, 5 eq) was added portionwise (CAUTION: vigorous bubbling!). A dark mixture was obtained at once. After 1 h at the same temperature, almost complete conversion of the starting material was observed by TLC (95/5/0.5 DCM/MeOH/$NH_4OH$). $NaBH_4$ (0.107 g, 2.5 mmol, 2.2 eq) was added and after 1 h the reaction was quenched by addiction of $NH_4OH$.

The mixture was filtered on a celite pad washing with MeOH. The solution was evaporated and the residue was suspended in DCM (15 mL). The mixture was filtered on a celite pad washing with DCM. The solution was evaporated and the crude (dark oil, complex mixture by TLC) was purified by flash chromatography (SNAP®, 10 g, $SiO_2$, Biotage) with 95/5/0.5 DCM/MeOH/$NH_4OH$ giving A0016_17_01 (0.022 g, yield 9%) as a dark oil.

Example A.21

General Procedure for 5-Oxazolyl Derivatives
Step a) Preparation of α-Aminonitriles
Method a1)

The appropriate oxazole alcohol intermediate (11) or intermediate (12) (0.858 mmol, 1 eq) was dissolved in DCM (1.5 mL) and the solution was cooled to 0° C. Dess-Martin periodinane (0.943 mmol, 1.1 eq) was added and the mixture was left stirring at the same temperature. After a few minutes a white suspension formed and after 30 min. the conversion was complete by TLC (95/5 DCM/MeOH). The aldehyde intermediate was not isolated. Glacial AcOH (5 mL), AcONa (1.93 mmol, 2.25 eq) and the appropriate amine (1.54 mmol, 1.8 eq) were sequentially added to the suspension and the mixture was allowed to warm to rt. After 1.5 hrs TMSCN (2.57 mmol, 3eq) was added and the mixture was left under stirring at the same temperature overnight. The volatiles were then evaporated and a saturated solution of $NaHCO_3$ (40 mL) was added to the residue. The mixture was extracted with EtOAc (20 mL×3) and the combined organic phases were dried (anh. $Na_2SO_4$) and concentrated under reduced pressure. The crude was purified by flash chromatography ($SiO_2$) using a mixture of petroleum ether and AcOEt varying between 9/1 and 4/6. The pure α-aminonitrile was obtained as a colourless oil (average yield 53%).

Using an analogous procedure intermediates A0015_60_01 (yield 45%), A0015_64_01 (yield 51%), A0015_65_01 (yield 40%) and A0017_43_01 (yield 37%) were prepared starting from intermediate (11); using morpholine, 4,4-difluoropiperidine hydrochloride, 1,2,3,4-tetrahydroisoquinoline or intermediate (10) respectively; intermediate A0016_31_01 (yield 45%), A0016_29_01, (yield 67%) and A0016_30_01 (yield 71%) were prepared starting from intermediate (12) using morpholine, 4,4-difluoropiperidine hydrochloride or 1,2,3,4-tetrahydroisoquinoline respectively.

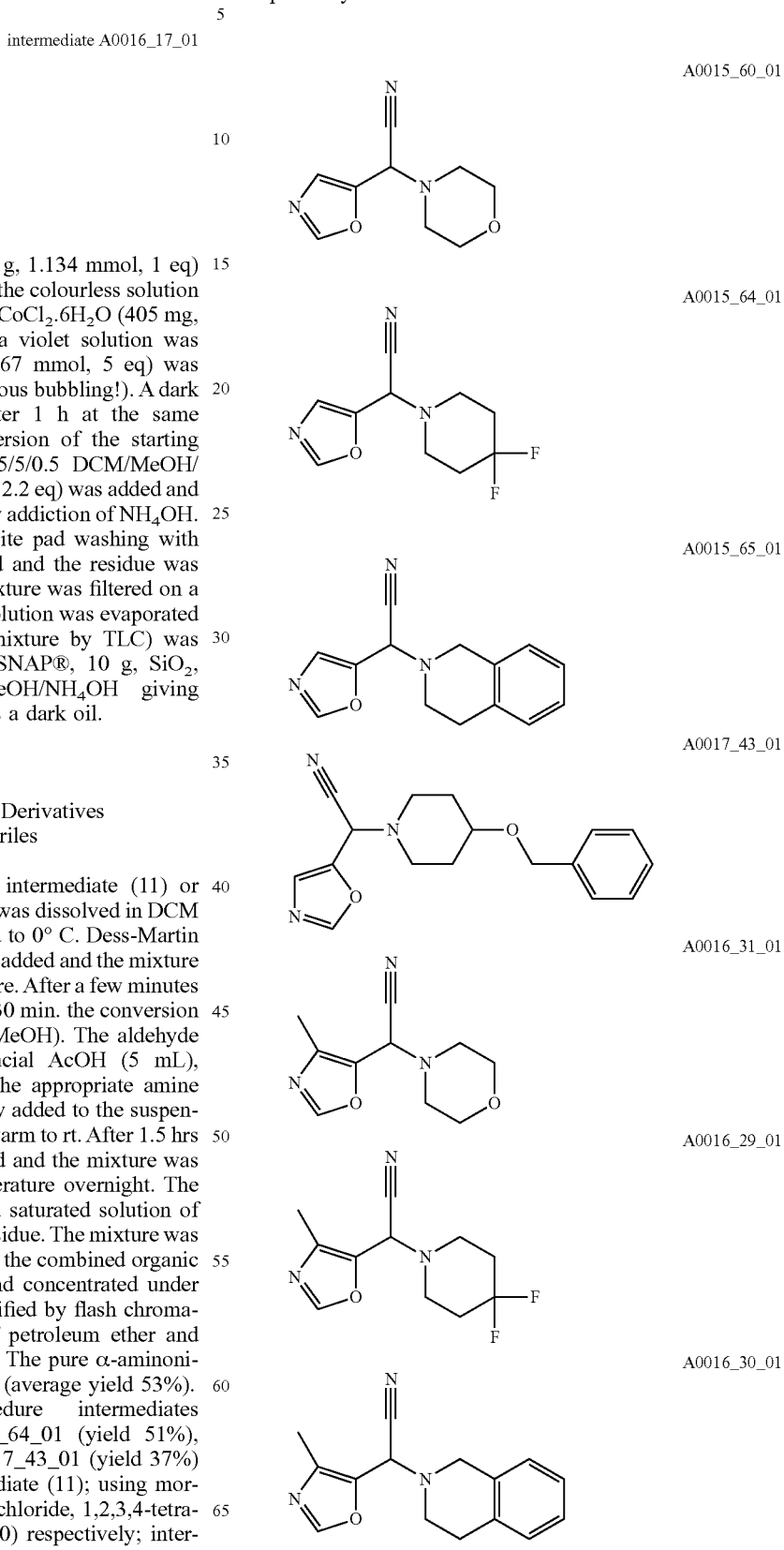

Method a2)
Preparation of

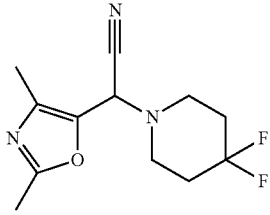
intermediate A0017_46_05

2,4-Dimethyloxazole-5-carbaldehyde (0.1 g, 0.8 mmol, 1 eq) was dissolved in glacial AcOH (2 mL). AcONa (1.91 mmol, 2.4 eq) and 4,4-difluoropiperidine hydrochloride (0.151 g, 0.96 mmol, 1.2 eq) were sequentially added stirring at room temperature under $N_2$. The yellow solution was stirred for 2 h and then was cooled to 0° C. TMSCN (0.3 mL, 2.4 mmol, 3 eq) was added dropwise and the mixture was allowed to warm to room temperature and stirred overnight. Then the reaction was stopped by addition of MeOH, and solvent was removed by evaporation.

The crude was dissolved in DCM, saturated solution of $NaHCO_3$ (20 mL) was added and the mixture was extracted with DCM (15 mL×3). The combined organic phases were dried (anh. $Na_2SO_4$) and evaporated. The crude was purified by flash chromatography ($SiO_2$) with 100% petroleum ether → 1/1 petroleum ether/ethyl acetate giving the pure title α-aminonitrile A0017_46_05 (0.237 g, yield 79%).

Step b) Preparation of Diamines

Method b1)

An α-aminonitrile (1 eq) was dissolved in 3M $NH_3$ in MeOH (100 eq) and the solution was hydrogenated in an H-Cube™ continuous flow apparatus with a Ni-Raney cartridge (30 mm CatCart®, ThalesNano), using a 1 mL/min flow. The hydrogen pressure was variable between 30 to 60 bar and the temperature between 30° C. to 40° C., depending on the substrate. After an appropiate time (generally 2 h), the solution was evaporated giving the pure primary amine that was used in the next step, without any purification (average yield 75%).

Using an analogous procedure intermediates A0015_61_01 (yield 83%), A0015_66_01 (yield 83%), A0015_67_02 (yield 79%) and A0017_67_01 (yield 80%) were prepared starting from A0015_60_01, A0015_64_01, A0015_65_01 and A0017_43_01 respectively. Intermediates A0017_27_01 (yield 65%), A0017_28_01 (yield 77%) and A0017_34_01 (yield 73%) were prepared starting from A0016_31_01, A0016_29_01 and A0016_30_01 respectively.

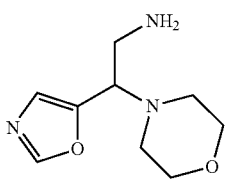
A0015_61_01

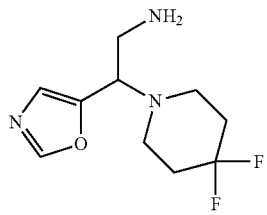
A0015_66_01

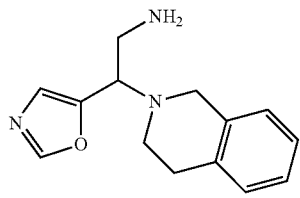
A0015_67_02

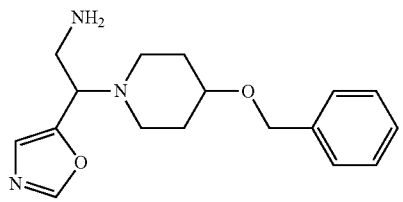
A0017_67_01

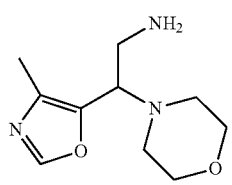
A0017_27_01

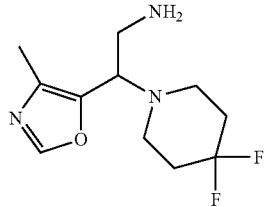
A0017_28_01

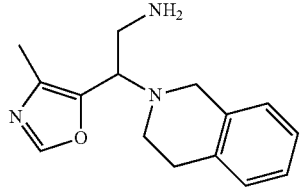
A0017_34_01

Method b2)
Preparation of

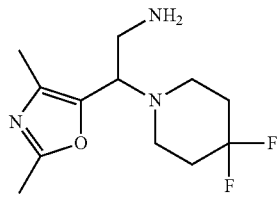
intermediate A0017_53_01

The α-aminonitrile A0017_46_05 (0.22 g, 0.86 mmol, 1 eq) was dissolved in 3M $NH_3$ in MeOH (100 eq) and the solution was hydrogenated in an H-Cube™ continuous flow apparatus with a Ni-Raney cartridge (30 mm CatCart®, ThalesNano), using a 1 mL/min flow. The hydrogen pressure was 50 bar and the temperature between 30° C. to 40° C. After 3 hrs, the hydrogenation was stopped and the solution was evaporated giving a crude containing the primary amine A0017_53_01 that was used in the next step, without any purification (0.175 g, yield 78%).

B Preparation of the Final Compounds

Example B.1

Method a)

Preparation of Final Products A0015_08_01, A0015_10_02 and A0015_12_01

A mixture of 2-chloro-6-fluorobenzoic acid (0.281 mmol, 1 eq) and HBTU (0.281 mmol, 1 eq) was dissolved in dry DMF (1.4 ml). The pale yellow solution was cooled to 0° C. under $N_2$ in a sealed tube and DIPEA (1.125 mmol, 4 eq) was added dropwise. After 16 hrs at the same temperature, a solution of a primary amine (A0013_40_01 or A0013_54_03 or A0013_33_01, 0.281 mmol, 1 eq) in dry DMF (1.4 mL) was added dropwise. The mixture was then allowed to warm to room temperature and after an appropriate time (30 min-1 h) the reaction was complete. The solvent was evaporated and the residue was partioned between a saturated solution of $NaHCO_3$ (20 mL) and DCM (15 mL). The aqueous phase was further extracted with DCM (15 ml×2) and the combined organic phases were dried ($Na_2SO_4$) and evaporated. The crude was purified by flash chromatography ($SiO_2$) with 85/15 DCM/EtOAc or 50/50 petroleum ether/ethyl acetate. The residue was purified by preparative LC-MS (see Analitical Part). The combined collected fractions were evaporated to a small volume (1-2 mL). Removal of the TFA counterion was performed by using a PL-$HCO_3$ MP SPE cartridge (Agilent Technologies, 0.1 g, 6 mL volume). Finally, freeze-drying was carried out by a Martin Christ system, giving the title compounds A0015_08_01, A0015_10_02 or A0015_12_01 (60% average yield for the coupling step).

Using an analogous procedure compound:
A0013_29_01 was prepared starting from A0013_28_01;
A0013_29_03 was prepared starting from A0013_28_03;
A0015_09_02 was prepared starting from A0011_54_01;
A0013_29_02 was prepared starting from A0013_30_01;
A0013_32_01 was prepared starting from A0013_31_01;
A0015_13_01 was prepared starting from A0015_11_01
A0015_28_03 was prepared starting from A0015_25_01 and oxalic acid;
A0017_05_01 was prepared starting from A0017_01_01;
A0016_10_01 was prepared starting from A0016_09_01;
A0016_20_03 was prepared starting from A0016_17_01;
A0015_55_01 was prepared starting from A0015_52_01;
A0015_58_02 was prepared starting from A0015_56_01;
A0015_57_02 was prepared starting from A0015_54_01;
A0012_60_01 was prepared starting from A0012_61_02;
A0012_64_01 was prepared starting from A0012_63_01;
A0015_62_03 was prepared starting from A0015_61_01;
A0015_68_02 was prepared starting from A0015_66_01;
A0015_69_02 was prepared starting from A0015_67_02;

Using an analogous procedure but replacing 2-chloro-6-fluorobenzoic acid with 2,6-dimethylbenzoic acid compounds
A0013_42_05 was prepared starting from A0013_40_01;
A0013_55_05 was prepared starting from A0013_54_03;
A0013_58_03 was prepared starting from A0013_33_01;
A0017_05_03 was prepared starting from A0017_01_01;
A0016_11_02 was prepared starting from A0016_09_01;
A0015_73_01 was prepared starting from A0015_52_01;
A0015_72_01 was prepared starting from A0015_56_01;
A0015_71_02 was prepared starting from A0015_54_01;
A0012_62_02 was prepared starting from A0012_61_02;
A0012_65_01 was prepared starting from A0012_63_01;
A0016_24_02 was prepared starting from A0015_66_01;
A0016_25_02 was prepared starting from A0015_67_02;

Using an analogous procedure but replacing 2-chloro-6-fluorobenzoic acid with 5-amino-2-chlorobenzoic acid compounds
A0013_42_04 was prepared staring from A0013_40_01;
A0013_55_04 was prepared starting from A0013_54_03;
A0013_58_02 was prepared starting from A0013_33_01.

Using an analogous procedure but replacing 2-chloro-6-fluorobenzoic acid with 2-chloro-6-methylbenzoic acid compounds
A0013_42_02 was prepared starting from A0013_40_01;
A0013_55_02 was prepared starting from A0013_54_03;
A0013_58_01 was prepared starting from A0013_33_01;
A0017_05_02 was prepared starting from A0017_01_01;
A0012_62_01 was prepared starting from A0012_61_02;
A0012_66_01 was prepared starting from A0012_63_01;
A0021_26_04 was prepared as mixture of two diastereoisomers starting from A0021_07_02.

A0021_26_03 was prepared as single diastereoisomer starting from A0021_26 04 by preparative LC-MS (see Analytical part)

Using an analogous procedure but replacing 2-chloro-6-fluorobenzoic acid with intermediate (4) compound
A0013_82_01 was prepared starting from A0013_54_03;
A0016_23_02 was prepared starting from A0015_56_01;
A0017_13_01 was prepared starting from A0015_54_01;
A0016_26_02 was prepared starting from A0015_66_01;
A0017_37_04 was prepared starting from A0017_28_01;
A0017_37_05 was prepared starting from A0017_27_01;
A0017_37_06 was prepared starting from A0017_34_01;
A0017_50_01 was prepared starting from A0012_61_02;
A0017_55_01 was prepared starting from A0017_53_01;
A0017_75_02 was prepared starting from A0017_73_01;
A0017_75_01 was prepared starting from A0017_72_01;
A0018_60_01 was prepared starting from A0018_58_01;
A0018_76_01 was prepared starting from A0018_75_01;
A0017_83_01 was prepared starting from A0017_58_01;
A0018_94_01 was prepared starting from A0018_93_01;
A0020_21_01 was prepared starting from A0020_19_01;
A0021_17_01 was prepared starting from A0020_26_01;
A0021_24_01 was prepared starting from A0020_37_01;
A0021_09_01 was prepared starting from A0021_07_03;
A0021_10_01 was prepared starting from A0021_07_04;
A0021_24_02 was prepared starting from A0020_38_01, without removal of the TFA counterion;
A0021_39_01 was prepared starting from A0020_69_01;
A0020_67_01 was prepared starting from A0020_66_01;
A0020_32_01 was prepared starting from A0020_31_01;
A0016_67_01 was prepared starting from A0016_57_01;
A0016_64_01 was prepared starting from A0016_59_01;
A0016_53_01 was prepared starting from A0016_48_01;
A0016_50_01 was prepared starting from A0016_47_01.

Using an analogous procedure but replacing 2-chloro-6-fluorobenzoic acid with intermediate (5), compound A0017_81_03 was obtained starting from A0015_56_01.

Using an analogous procedure but replacing 2-chloro-6-fluorobenzoic acid with intermediate (6), compound A0017_81_02 was obtained starting from A0015_56_01; compound A0018_88_01 was obtained starting from A0012_61_02; compound A0020_21_02 was obtained starting from A0020_1901; compound A0020_28_01 was obtained starting from A0020_26_01; compound A0021_0902 was obtained starting from A0021_0703; compound A0021_1002 was obtained starting from A0021_07_04; compound A0021_3802 was obtained starting from A0020_66_01

Using an analogous procedure but replacing 2-chloro-6-fluorobenzoic acid with intermediate (7), compound A0017_85_01 was obtained starting from A0015_56_01; compound A0018_89_01 was obtained starting from A0012_61_02.

Using an analogous procedure but replacing 2-chloro-6-fluorobenzoic acid with intermediate (8) compound A0018_69_01 was obtained starting from A0015_56_01; compound A0018_89_02 was obtained starting from A0012_61_02.

Using an analogous procedure but replacing 2-chloro-6-fluorobenzoic acid with 5-quinolinecarboxylic acid, compound A0016_21_02 was prepared starting from A0015_56_01; compound A0021_2602 was obtained starting from A0021_07_02; A0021_38_01 was obtained starting from A0020_66_01; A0021_39_02 was obtained starting from A0020_69_01; compound A0016_54_01 was obtained starting from A0016_48_01; A0016_68_01 was obtained starting from A0016_57_01; A0016_65_01 was obtained starting from A0016_59_01.

Using an analogous procedure but replacing 2-chloro-6-fluorobenzoic acid with 2,3-dimethoxybenzoic acid compound
  A0017_09_03 was prepared starting from A0013_54_03;
  A0017_37_01 was prepared starting from A0017_28_01;
  A0017_37_02 was prepared starting from A0017_27_01;
  A0017_37_03 was prepared starting from A0017_34_01.

Using an analogous procedure but replacing 2-chloro-6-fluorobenzoic acid with 2-chloro-4-(1,1-dioxido-2-isothiazolidinyl)-benzoic acid compound A0016_60_01 was prepared starting from A0015_56_01.

Using an analogous procedure but replacing 2-chloro-6-fluorobenzoic acid with 7-fluoro-2-oxo-1,2,3,4-tetrahydroquinoline-6-carboxylic acid compound A0016_61_01 was prepared staring from A0015_56_01.

Method b)

2-chloro-6-fluorobenzoyl chloride (0.013 mL, 0.09 mmol, 1.05 eq) was added to a stirred solution of the primary amine (0.08 mmol) in dry DCM (1 mL) and TEA (0.063 mL, 0.45 mmol, 5 eq). The reaction mixture was stirred overnight at room temperature then portitioned between 2% KOH and DCM. The organic layers were dried over $Na_2SO_4$ (dry), filtered and finally evaporated to afford crude final product, that was purified by preparative LC-MS (see Analitical Part). The combined collected fractions were evaporated to a small volume (1-2 mL). Removal of the TFA counterion was performed by using a PL-HCO_3 MP SPE cartridge (Agilent Technologies, 0.1 g, 6 mL volume). Finally, freeze-drying was carried out by a Martin Christ system, affording the free base final product.
  A0017_33_01 was prepared starting from A0017_28_01;
  A0017_33_02 was prepared starting from A0017_27_01;
  A0017_60_02 was prepared starting from A0017_59_01;
  A0017_60_01 was prepared starting from A0017_58_01;
  A0018_17_01 was prepared staring from A0018_16_01;
  A0017_68_01 was prepared staring from A0017_67_01;
  A0017_74_02 was prepared starting from A0017_73_01;
  A0018_59_01 was prepared starting from A0018_58_01;
  A0018_95_01 was prepared starting from A0018_93_01;
  A0020_20_01 was prepared starting from A0020_19_01;
  A0020_27_01 was prepared starting from A0020_26_01;
  A0021_07_11 was prepared starting from A0021_07_01;
  A0021_07_22 was prepared starting from A0021_07_02;
  A0021_07_44 was prepared starting from A0021_07_04;
  A0021_07_33 was prepared starting from A0021_07_03;
  A0021_25_02 was prepared starting from A0020_38_01, without removal of the TFA counterion;
  A0021_40_01 was prepared starting from A0020_69_01;
  A0020_68_01 was prepared starting from A0020_66_01;
  A0016_52_01 was prepared starting from A0016_48_01;
  A0016_49_01 was prepared starting from A0016_47_01;
  A0016_63_01 was prepared starting from A0016_59_01;
  A0016_66_01 was prepared starting from A0016_57_01
  A0022_02_01 was prepared starting from A0022_01_01

Using an analogous procedure but replacing 2-chloro-6-fluorobenzoyl chloride with 2,6-difluorobenzoyl chloride A0017_09_02 was prepared starting from A0013_54_03.

Example B.2

Preparation of

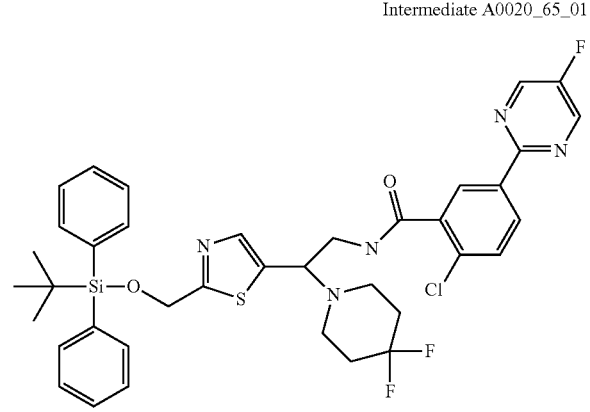 [SMILES: CC(C)(C)[Si](OCc1ncc(C(CNC(=O)c2cc(-c3ncc(F)cn3)ccc2Cl)N2CCC(F)(F)CC2)s1)(c1ccccc1)c1ccccc1]

Intermediate A0020_65_01

A mixture of intermediate 4 (0.056 g, 0.22 mmol, 1.2 eq) and HBTU (0.08 g, 0.28 mmol, 1.15 eq) was dissolved in dry DMF (3 ml). The pale yellow solution was cooled to 0° C. under $N_2$ in a sealed tube and DIPEA (0.093 mL, 0.55 mmol, 3 eq) was added dropwise. After 1 h at the same temperature, a solution of A0020_63_01 (0.095 g, 0.18 mmol, 1 eq) in dry DMF (1 mL) was added dropwise. The mixture was then allowed to warm to room temperature and stirred overnight. The solvent was evaporated and the residue was partioned between a saturated solution of $NaHCO_3$ (20 mL) and DCM (15 mL). The aqueous phase was further extracted with DCM (15 mL×2) and the combined organic phases were dried ($Na_2SO_4$) and evaporated. The crude (0.17 g) was purified by flash chromatography ($SiO_2$) with 50/50 petroleum ether/ethyl acetate, giving intermediate A0020_65_01 (0.09 g, yield 66%).

Preparation of

Compound A0020_71_01

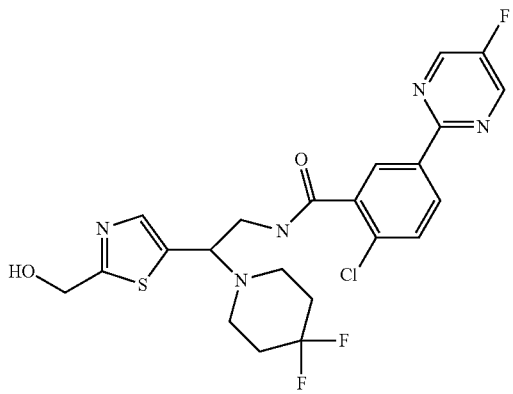

A0020_65_01 (0.09 g, 0.120 mmol, 1 eq) was dissolved in dry THF (2 mL) and treated with 1M tetrabutylammonium fluoride in THF (1.32 mL, 1.32 mmol, 1.2 eq) at room temperature. After 1 h, NH$_4$Cl sat. solution (1 mL) was added, solvent was removed under reduced pressure and the residue partitioned between NaHCO$_3$ sat. solution (4 mL) and DCM (4 mL). The combined organic extract were dried over anh. Na$_2$SO$_4$, filtered and evaporated, yielding a crude (0.08 g) which was purified by preparative LC-MS (see analytical part), yielding A0020_71_01 (0.01 g, yield 16%) as white solid.

Example B.3

Preparation of

Compound A0018_81_01

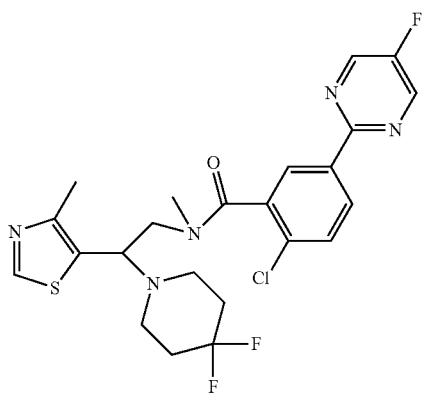

A0016_23_02 (0.33 g, 0.067 mmol, 1 eq) was dissolved in dry DMF (0.7 mL) and cooled to 0-5° C. under argon atmosphere. NaH (60% suspension in mineral oil, 0.003 g, 0.074 mmol, 1.1 eq) was added in one portion and the resulting yellow solution was stirred at 0° C. for 30 min. Then, a solution of methyl iodide (0.0086 g, 0.061 mmol, 0.9 eq) in dry DMF (0.1 mL) was added, and the reaction mixture was stirred at 0° C. for 2 minutes, then at room temperature for 30 min. The reaction was stopped by adding water (0.1 mL) and MeOH (0.1 mL). The solvent was removed by evaporation under reduced pressure. The residue was dissolved in DCM (3 mL) and washed with 5% citric acid solution in water (3 mL), sat. sodium bicarbonate solution (3 mL) and brine (3 mL). The organic layer was dried over anh. Na$_2$SO$_4$, filtered and evaporated giving 0.043 g of crude which was purified by preparative LC-MS (see analytical part), giving A0018_81_01 (19 mg, yield 28%) as white solid.

Example B.4

Preparation of

Compound A0021_11_01

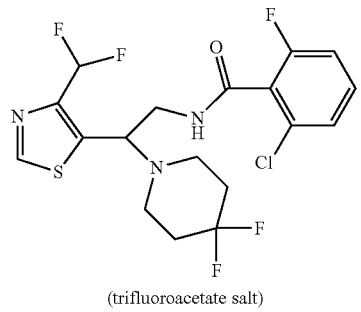

(trifluoroacetate salt)

A0018_98_01 (0.040 g, 0.136 mmol, 1 eq) was dissolved in MeOH (4.5 mL) and the solution was hydrogenated in an H-Cube™ continuous flow apparatus with a Ni-Raney cartridge (55 mm long CatCart), using a 0.7 mL/min flow. The hydrogen pressure was 50 bar and the temperature 35° C. After 1 h, the solution was treated with oxalic acid (0.037 g, 0.408 mmol, 3 eq) and stirred for 30 min at room temperature. Solvent was removed under reduced pressure and the crude crystallized by adding diethyl ether (1 mL). The resulting solid was washed 3 times with diethyl ether, affording a light yellow powder that was used as such.

The crude yellow oxalate salt, was suspended in THF (2 mL), and 2-chloro-5-fluoro-benzoylchloride (0.077 g, 0.4 mmol, 2.94 eq) was added, followed by an aq. saturated solution of NaHCO$_3$ (1 mL). The resulting mixture was stirred for 1 h at room temperature. Solvents were removed at reduced pressure and the water layer was extracted by DCM (10 mL×2). The combined organic extracts were dried over anh. Na$_2$SO$_4$, filtered and evaporated. The crude was purified by flash chromatography on silica gel (EtOAc/petroleum ether 50/50), yielding a crude oil (30 mg) which was purified by preparative LC-MS (see analytical part). The collected fractions were evaporated to a small volume (1-2 mL). Removal of the TFA counterion was performed by using a PL-HCO$_3$ MP SPE cartridge (Agilent Technologies, 0.1 g, 6 mL volume). Freeze-drying was carried out by a Martin Christ system, giving white solid, which was dissolved in diethyl ether (1 mL), treated with oxalic acid (1.5 eq) and the resulting solid filtered and washed with diethyl ether (5 mL×3), giving A0021_11_01 (0.019 g, yield 23%) as trifluoroacetate salt.

Example B.5

Preparation of

Compound A0021_24_04

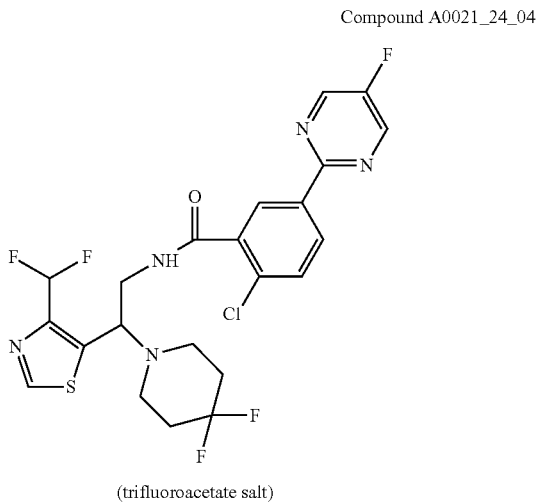 [SMILES: O=C(NCC(c1scnc1C(F)F)N1CCC(F)(F)CC1)c1cc(-c2ncc(F)cn2)ccc1Cl]

(trifluoroacetate salt)

A0018_98_01 (0.07 g, 0.238 mmol, 1 eq) was dissolved in MeOH (3mL) and the solution was hydrogenated in an H-Cube™ continuous flow apparatus with a Ni-Raney cartridge (55 mm long CatCart), using a 1 mL/min flow. The hydrogen pressure was 40 bar and the temperature 35° C. After 1.5 hours, the solution was treated with oxalic acid (0.15 g, 1.66 mmol, 6.9 eq), and the solvent was removed under reduced pressure affording a white powder that was used as such containing mainly a primary amine as oxalate salt.

A mixture of intermediate 4 (0.033 g, 0.13 mmol, 1.1 eq) and HBTU (0.049 g, 0.13 mmol, 1.1 eq) was dissolved in dry DMF (0.5 mL). The pale yellow solution was cooled to 0° C. under $N_2$ in a sealed tube and dry TEA (0.105 mL, 0.75 mmol, 3 eq) was added dropwise. After 2.5 hrs at the same temperature, a solution of the primary amine oxalate salt (0.033 g, 0.13 mmol, 1 eq) in dry DMF (1 mL) was added and the reaction stirred for 15 minutes at 0° C., then at room temperature overnight. The reaction was quenched by adding water (0.1 mL) and evaporated. The crude was dissolved in DCM (3 mL), washed with sodium carbonate aq. saturated solution (23 mL×2) and brine (20 mL). The organic layer was dried over $Na_2SO_4$, filtered and evaporated. The crude was purified by flash cromatography over silica gel (EtOAc/petroleum ether 50/50) affording 0.011 g of a solid containing A0021_24_04.

The procedure was repeated starting from A0018_98_01 (0.07 g, 0.238 mmol), giving 0.012 g of a solid containing A0021_24_04. The two batches containing A0021_24_04 were combined and purified by preparative LC-MS (see Analytical Part). The combined fractions were evaporated to a small volume (1-2 mL). Finally, freeze-drying was carried out by a Martin Christ system, giving A0021_24_04 (0.015 g, yield 10%) as trifluoroacetate salt.

Table F-1 lists final compounds that were prepared and tested according to the experimental procedure described as example B.1, B.2, B.3, B.4 and B.5

| Compound | Code | Structure |
|---|---|---|
| 1 | A0013_29_01 | 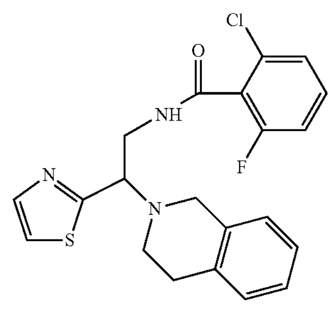 [SMILES: O=C(NCC(c1nccs1)N1CCc2ccccc2C1)c1c(F)cccc1Cl] |
| 2 | A0013_29_03 | 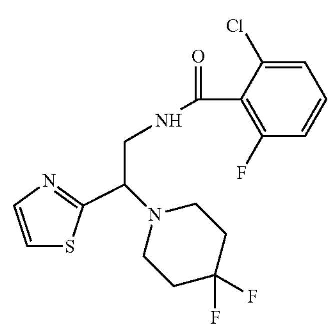 [SMILES: O=C(NCC(c1nccs1)N1CCC(F)(F)CC1)c1c(F)cccc1Cl] |

-continued

| Compound | Code | Structure |
|---|---|---|
| 3 | A0015_09_02 | 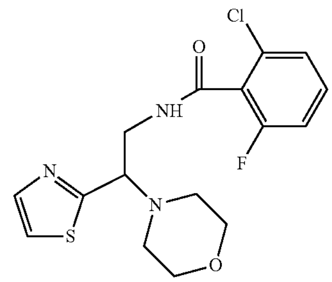 [SMILES: O=C(NCC(c1nccs1)N1CCOCC1)c1c(F)cccc1Cl] |
| 4 | A0013_29_02 | 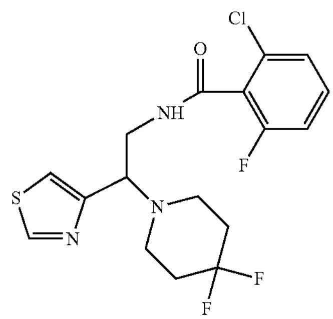 [SMILES: O=C(NCC(c1cscn1)N1CCC(F)(F)CC1)c1c(F)cccc1Cl] |
| 5 | A0013_32_01 | 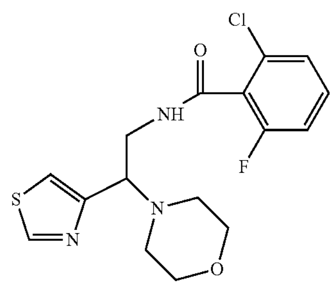 [SMILES: O=C(NCC(c1cscn1)N1CCOCC1)c1c(F)cccc1Cl] |
| 6 | A0015_13_01 | 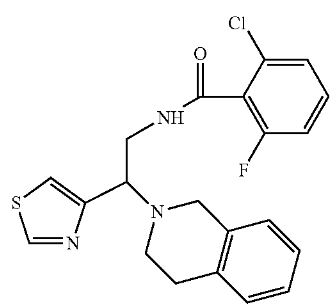 [SMILES: O=C(NCC(c1cscn1)N1CCc2ccccc2C1)c1c(F)cccc1Cl] |
| 7 | A0015_28_03 (oxalate salt) | 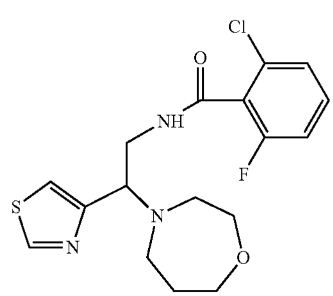 [SMILES: O=C(NCC(c1cscn1)N1CCCOCC1)c1c(F)cccc1Cl] |

-continued

| Compound | Code | Structure |
|---|---|---|
| 8 | A0015_10_02 | 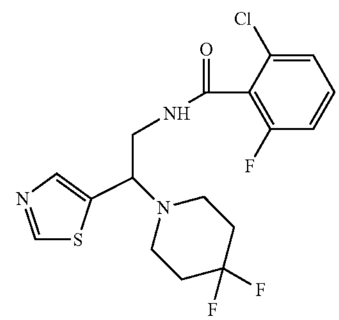 [SMILES: O=C(NCC(c1cncs1)N1CCC(F)(F)CC1)c1c(F)cccc1Cl] |
| 9 | A0015_12_01 | 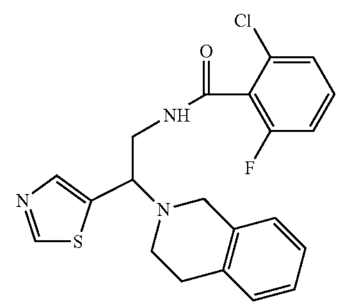 [SMILES: O=C(NCC(c1cncs1)N1CCc2ccccc2C1)c1c(F)cccc1Cl] |
| 10 | A0015_08_01 | 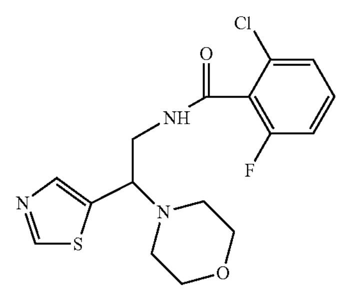 [SMILES: O=C(NCC(c1cncs1)N1CCOCC1)c1c(F)cccc1Cl] |
| 11 | A0013_42_05 | 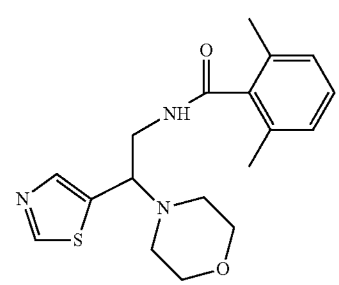 [SMILES: Cc1cccc(C)c1C(=O)NCC(c1cncs1)N1CCOCC1] |
| 12 | A0013_42_04 | 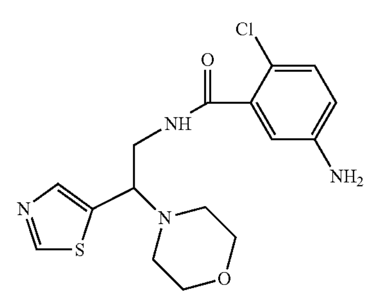 [SMILES: Nc1ccc(Cl)c(C(=O)NCC(c2cncs2)N2CCOCC2)c1] |

-continued
| Compound | Code | Structure |
|---|---|---|
| 13 | A0013_42_02 | 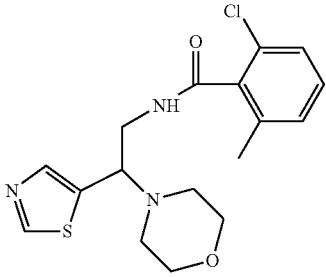 [SMILES: Cc1cccc(Cl)c1C(=O)NCC(c1cncs1)N1CCOCC1] |
| 14 | A0013_55_05 | 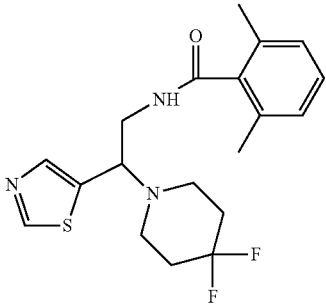 |
| 15 | A0013_55_02 | 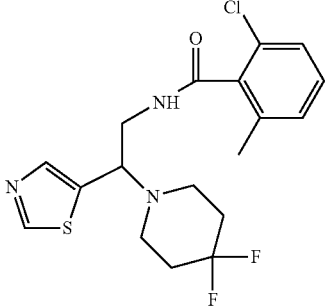 [SMILES: Cc1cccc(Cl)c1C(=O)NCC(c1cncs1)N1CCC(F)(F)CC1] |
| 16 | A0013_55_04 | 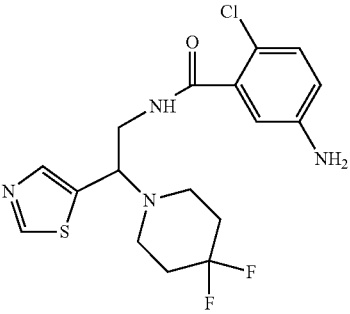 [SMILES: Nc1ccc(Cl)c(C(=O)NCC(c2cncs2)N2CCC(F)(F)CC2)c1] |
| 17 | A0013_58_02 | 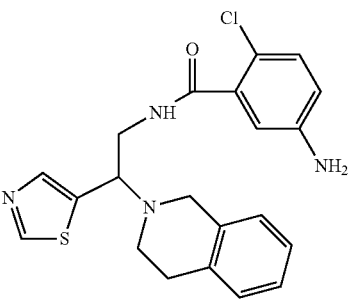 [SMILES: Nc1ccc(Cl)c(C(=O)NCC(c2cncs2)N2CCc3ccccc3C2)c1] |

-continued
| Compound | Code | Structure |
|---|---|---|
| 18 | A0013_58_03 | 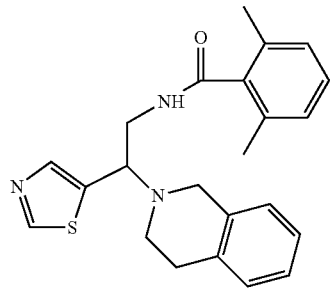 [SMILES: Cc1cccc(C)c1C(=O)NCC(c1cncs1)N1CCc2ccccc2C1] |
| 19 | A0013_58_01 | 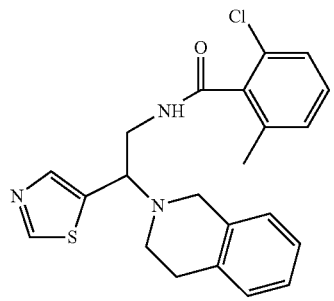 [SMILES: Cc1cccc(Cl)c1C(=O)NCC(c1cncs1)N1CCc2ccccc2C1] |
| 20 | A0013_82_01 | 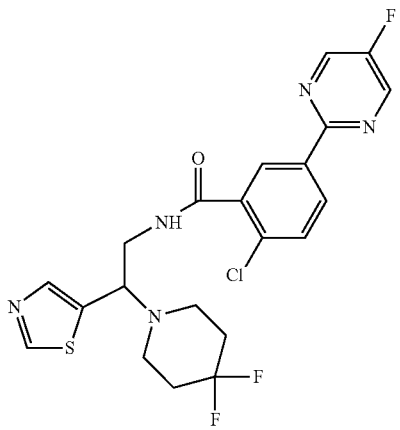 [SMILES: O=C(NCC(c1cncs1)N1CCC(F)(F)CC1)c1cc(-c2ncc(F)cn2)ccc1Cl] |
| 21 | A0017_09_03 | 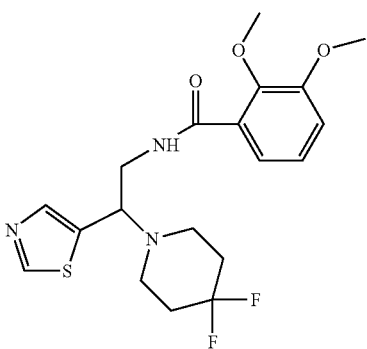 [SMILES: COc1cccc(C(=O)NCC(c2cncs2)N2CCC(F)(F)CC2)c1OC] |

-continued

| Compound | Code | Structure |
|---|---|---|
| 22 | A0017_09_02 | 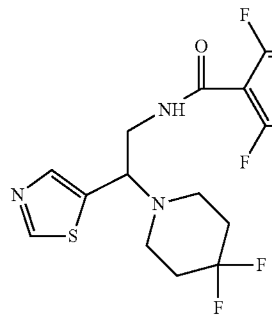 |
| 23 | A0017_05_03 | 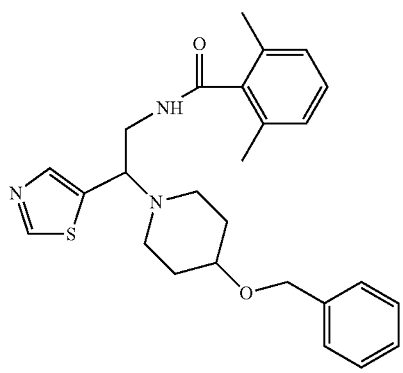 [SMILES: Cc1cccc(C)c1C(=O)NCC(c1cncs1)N1CCC(OCc2ccccc2)CC1] |
| 24 | A0017_05_02 | 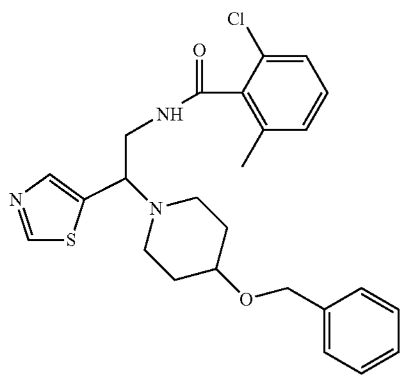 [SMILES: Cc1cccc(Cl)c1C(=O)NCC(c1cncs1)N1CCC(OCc2ccccc2)CC1] |
| 25 | A0017_05_01 | 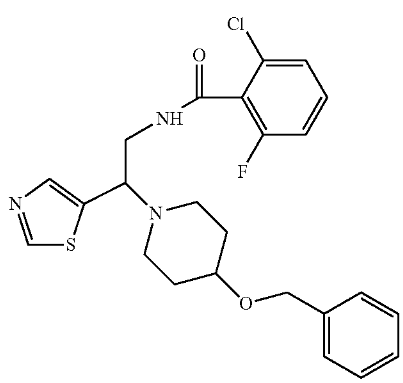 [SMILES: O=C(NCC(c1cncs1)N1CCC(OCc2ccccc2)CC1)c1c(F)cccc1Cl] |

-continued
| Compound | Code | Structure |
|---|---|---|
| 26 | A0016_11_02 | 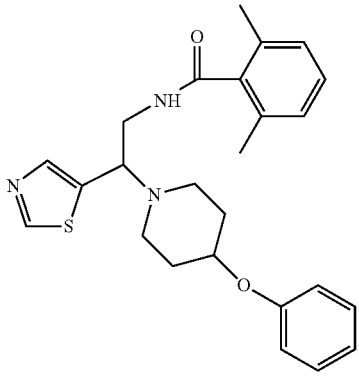 [SMILES: Cc1cccc(C)c1C(=O)NCC(c1cncs1)N1CCC(Oc2ccccc2)CC1] |
| 27 | A0016_10_01 | 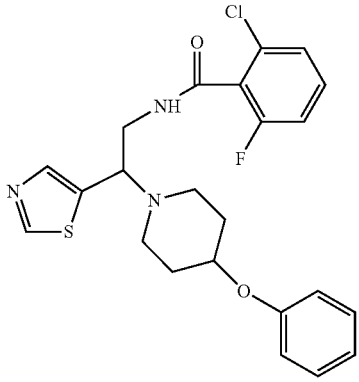 [SMILES: O=C(NCC(c1cncs1)N1CCC(Oc2ccccc2)CC1)c1c(F)cccc1Cl] |
| 28 | A0016_20_03 | 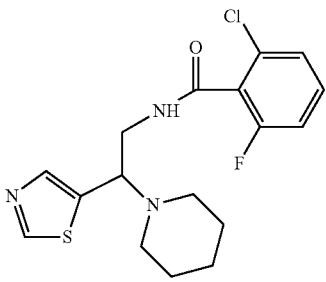 [SMILES: O=C(NCC(c1cncs1)N1CCCCC1)c1c(F)cccc1Cl] |
| 29 | A0015_55_01 | 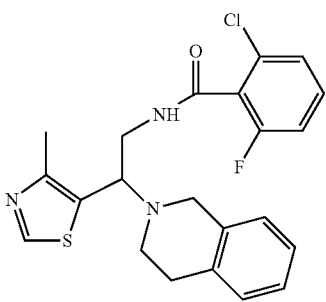 [SMILES: Cc1ncsc1C(CNC(=O)c1c(F)cccc1Cl)N1CCc2ccccc2C1] |

-continued

| Compound | Code | Structure |
|---|---|---|
| 30 | A0015_73_01 | 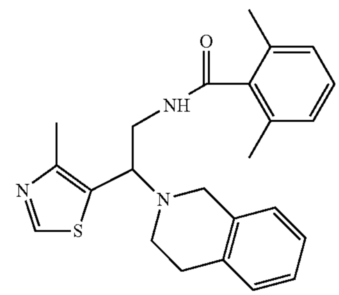 [SMILES: Cc1cccc(C)c1C(=O)NCC(c1scnc1C)N1CCc2ccccc2C1] |
| 31 | A0015_58_02 | 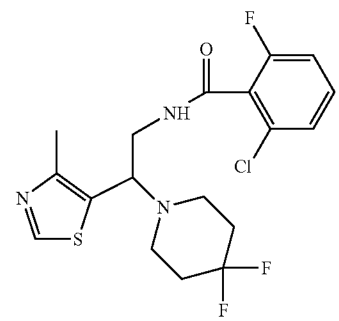 [SMILES: Cc1ncsc1C(CNC(=O)c1c(F)cccc1Cl)N1CCC(F)(F)CC1] |
| 32 | A0015_72_01 | 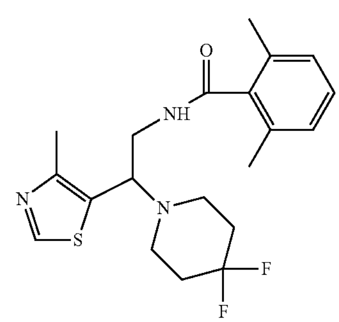 [SMILES: Cc1cccc(C)c1C(=O)NCC(c1scnc1C)N1CCC(F)(F)CC1] |
| 33 | A0016_21_02 | 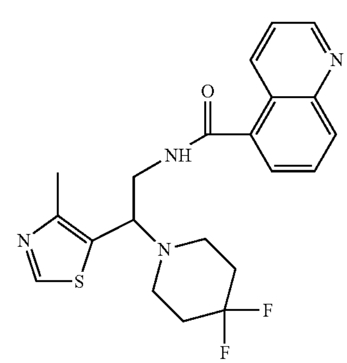 [SMILES: Cc1ncsc1C(CNC(=O)c1cccc2ncccc12)N1CCC(F)(F)CC1] |

-continued
| Compound | Code | Structure |
|---|---|---|
| 34 | A0016_23_02 | 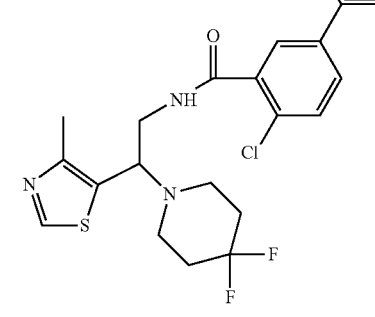 |
| 35 | A0015_57_02 | 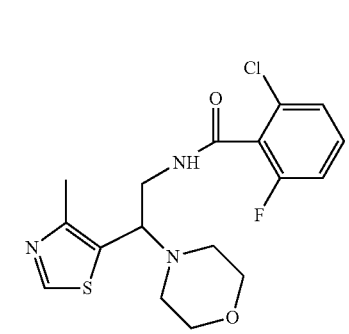 [SMILES: Cc1ncsc1C(CNC(=O)c1c(F)cccc1Cl)N1CCOCC1] |
| 36 | A0015_71_02 | 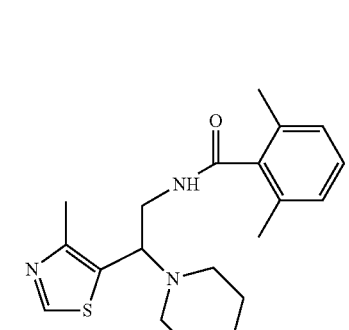 |
| 37 | A0017_13_01 | 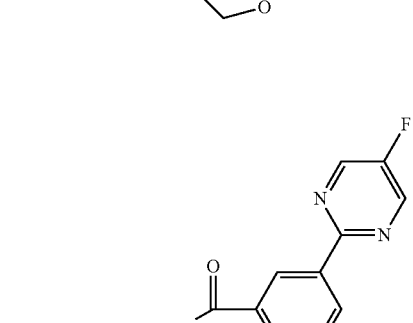 |

-continued

| Compound | Code | Structure |
|---|---|---|
| 38 | A0012_60_01 | 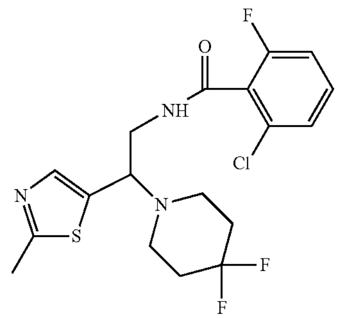 [SMILES: Cc1ncc(C(CNC(=O)c2c(F)cccc2Cl)N2CCC(F)(F)CC2)s1] |
| 39 | A0012_62_01 | 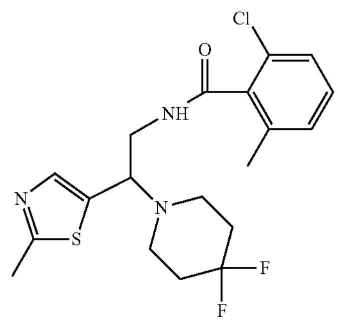 [SMILES: Cc1ncc(C(CNC(=O)c2c(C)cccc2Cl)N2CCC(F)(F)CC2)s1] |
| 40 | A0012_62_02 | 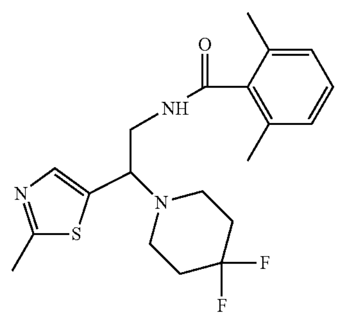 [SMILES: Cc1ncc(C(CNC(=O)c2c(C)cccc2C)N2CCC(F)(F)CC2)s1] |
| 41 | A0012_66_01 | 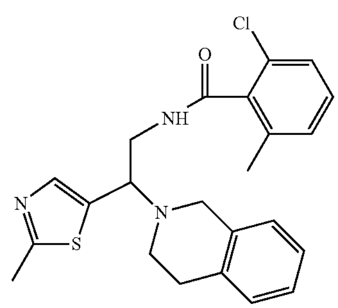 [SMILES: Cc1ncc(C(CNC(=O)c2c(C)cccc2Cl)N2CCc3ccccc3C2)s1] |
| 42 | A0012_65_01 | 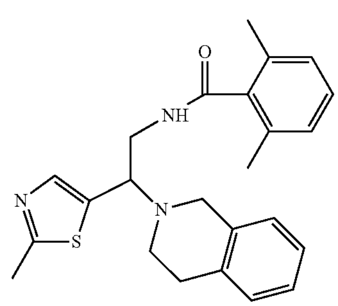 [SMILES: Cc1ncc(C(CNC(=O)c2c(C)cccc2C)N2CCc3ccccc3C2)s1] |

-continued
| Compound | Code | Structure |
|---|---|---|
| 43 | A0012_64_01 | 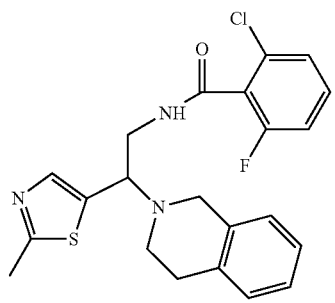 [SMILES: Cc1ncc(C(CNC(=O)c2c(F)cccc2Cl)N2CCc3ccccc3C2)s1] |
| 44 | A0015_62_03 | 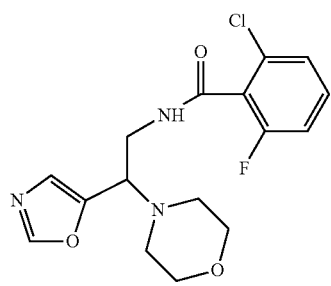 |
| 45 | A0015_68_02 | 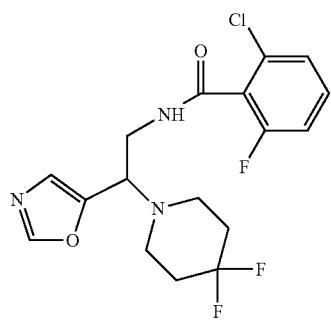 [SMILES: O=C(NCC(c1cnco1)N1CCC(F)(F)CC1)c1c(F)cccc1Cl] |
| 46 | A0016_24_02 | 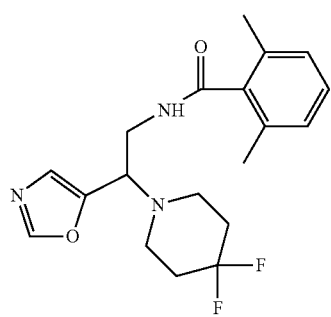 [SMILES: Cc1cccc(C)c1C(=O)NCC(c1cnco1)N1CCC(F)(F)CC1] |

-continued
| Compound | Code | Structure |
|---|---|---|
| 47 | A0016_26_02 | 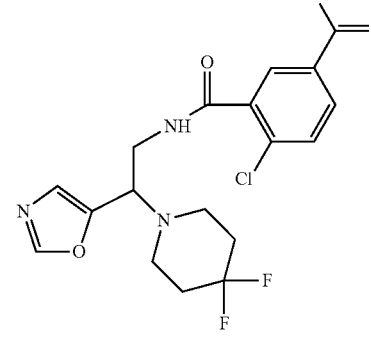 |
| 48 | A0015_69_02 | 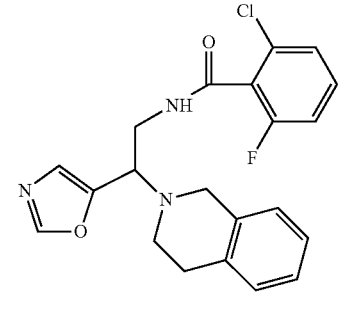 [SMILES: O=C(NCC(c1cnco1)N1CCc2ccccc2C1)c1c(F)cccc1Cl] |
| 49 | A0016_25_02 | 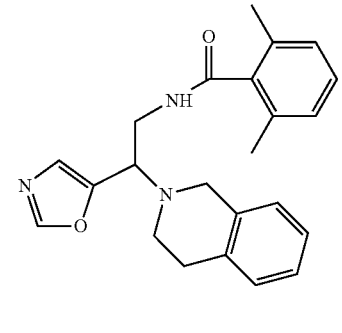 [SMILES: Cc1cccc(C)c1C(=O)NCC(c1cnco1)N1CCc2ccccc2C1] |
| 50 | A0017_37_01 | 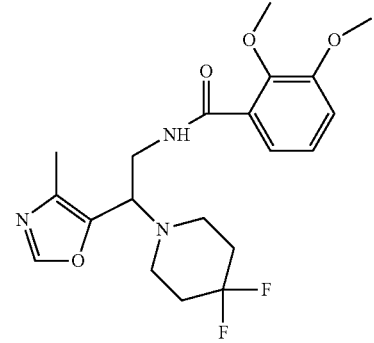 [SMILES: COc1cccc(C(=O)NCC(c2ocnc2C)N2CCC(F)(F)CC2)c1OC] |

-continued

| Compound | Code | Structure |
|---|---|---|
| 51 | A0017_37_04 | 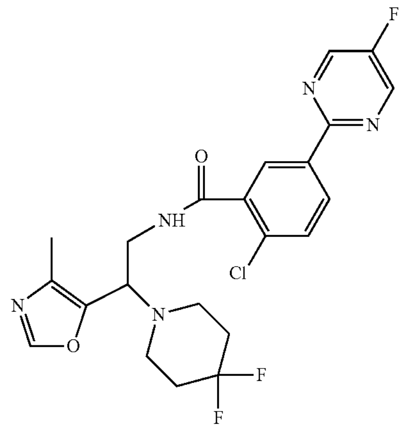 [SMILES: Cc1ncoc1C(CNC(=O)c1cc(-c2ncc(F)cn2)ccc1Cl)N1CCC(F)(F)CC1] |
| 52 | A0017_33_01 | 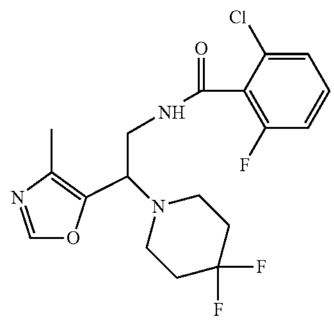 [SMILES: Cc1ncoc1C(CNC(=O)c1c(F)cccc1Cl)N1CCC(F)(F)CC1] |
| 53 | A0017_37_02 | 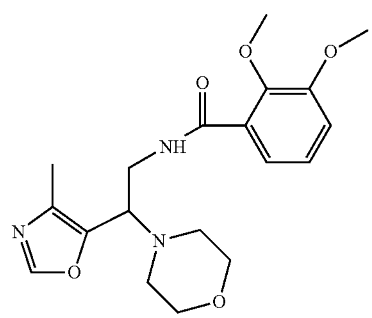 [SMILES: COc1cccc(C(=O)NCC(c2ocnc2C)N2CCOCC2)c1OC] |
| 54 | A0017_37_05 | 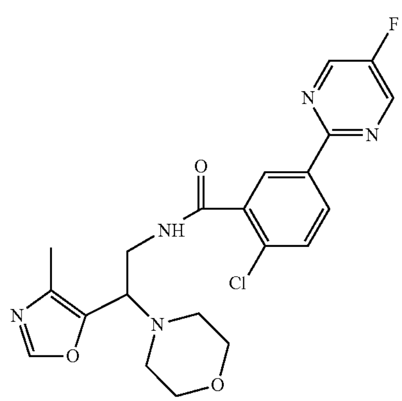 |

-continued

| Compound | Code | Structure |
|---|---|---|
| 55 | A0017_33_02 | 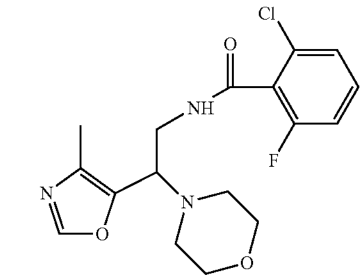 [SMILES: Cc1ncoc1C(CNC(=O)c1c(F)cccc1Cl)N1CCOCC1] |
| 56 | A0017_37_03 | 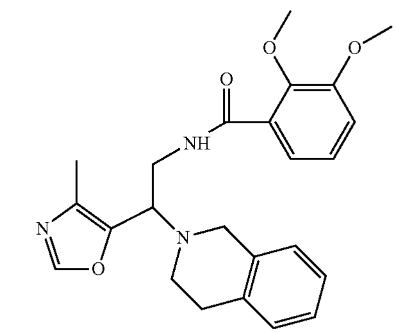 [SMILES: COc1cccc(C(=O)NCC(c2ocnc2C)N2CCc3ccccc3C2)c1OC] |
| 57 | A0017_37_06 | 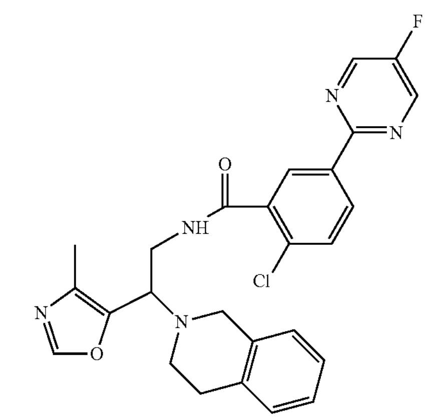 [SMILES: Cc1ncoc1C(CNC(=O)c1cc(-c2ncc(F)cn2)ccc1Cl)N1CCc2ccccc2C1] |
| 58 | A0017_55_01 | 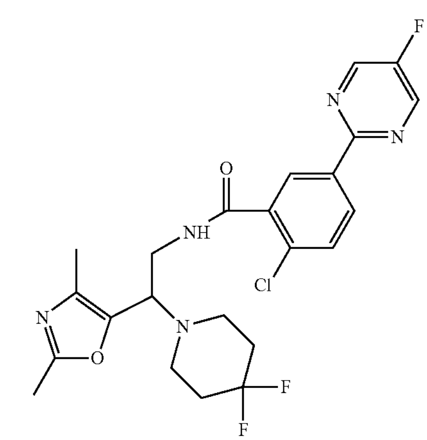 [SMILES: Cc1nc(C)c(C(CNC(=O)c2cc(-c3ncc(F)cn3)ccc2Cl)N2CCC(F)(F)CC2)o1] |

-continued
| Compound | Code | Structure |
|---|---|---|
| 59 | A0017_60_02 | 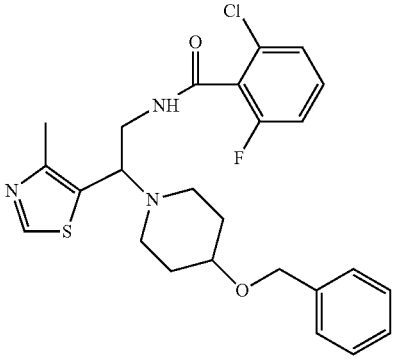 [SMILES: Cc1ncsc1C(CNC(=O)c1c(F)cccc1Cl)N1CCC(OCc2ccccc2)CC1] |
| 60 | A0017_60_01 | 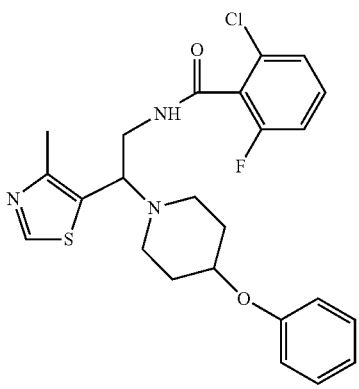 [SMILES: Cc1ncsc1C(CNC(=O)c1c(F)cccc1Cl)N1CCC(Oc2ccccc2)CC1] |
| 61 | A0017_50_01 | 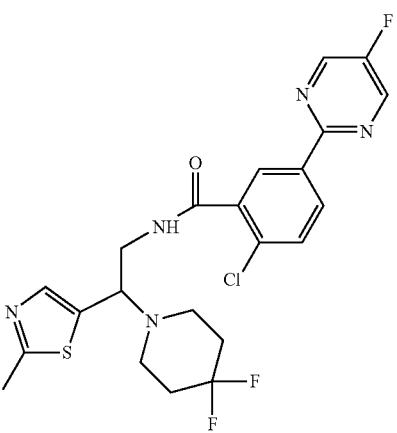 [SMILES: Cc1ncc(C(CNC(=O)c2cc(-c3ncc(F)cn3)ccc2Cl)N2CCC(F)(F)CC2)s1] |
| 62 | A0018_17_01 | 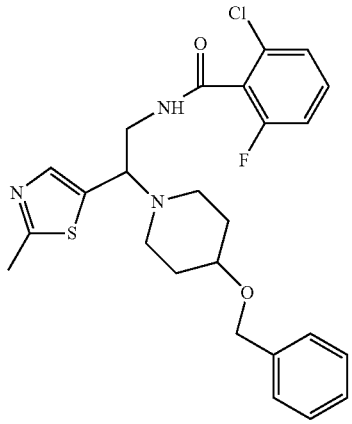 [SMILES: Cc1ncc(C(CNC(=O)c2c(F)cccc2Cl)N2CCC(OCc3ccccc3)CC2)s1] |

| Compound | Code | Structure |
|---|---|---|
| 63 | A0017_68_01 | 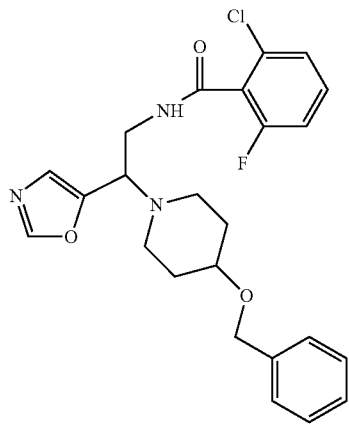 [SMILES: O=C(NCC(c1cnco1)N1CCC(OCc2ccccc2)CC1)c1c(F)cccc1Cl] |
| 64 | A0017_74_02 | 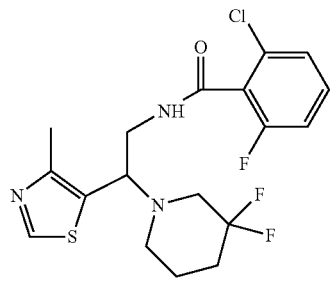 [SMILES: Cc1ncsc1C(CNC(=O)c1c(F)cccc1Cl)N1CCCC(F)(F)C1] |
| 65 | A0017_75_01 | 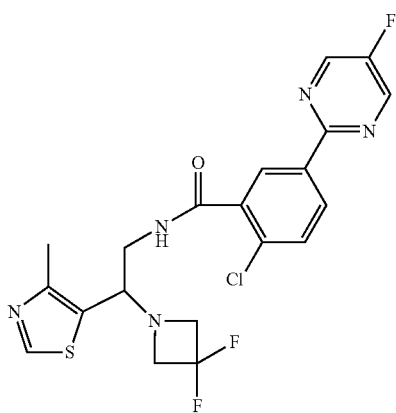 [SMILES: Cc1ncsc1C(CNC(=O)c1cc(-c2ncc(F)cn2)ccc1Cl)N1CC(F)(F)C1] |
| 66 | A0017_75_02 | 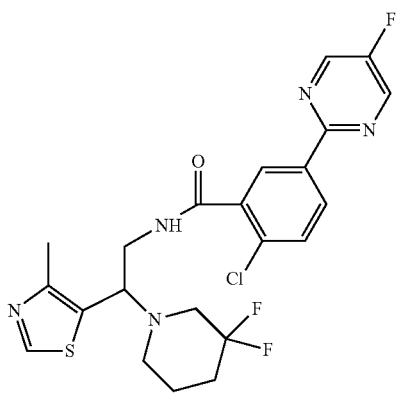 [SMILES: Cc1ncsc1C(CNC(=O)c1cc(-c2ncc(F)cn2)ccc1Cl)N1CCCC(F)(F)C1] |

-continued

| Compound | Code | Structure |
|---|---|---|
| 67 | A0018_59_01 | 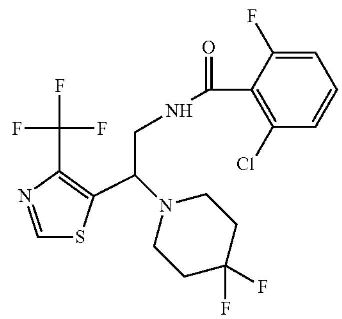 [SMILES: O=C(NCC(c1scnc1C(F)(F)F)N1CCC(F)(F)CC1)c1c(F)cccc1Cl] |
| 68 | A0018_60_01 | 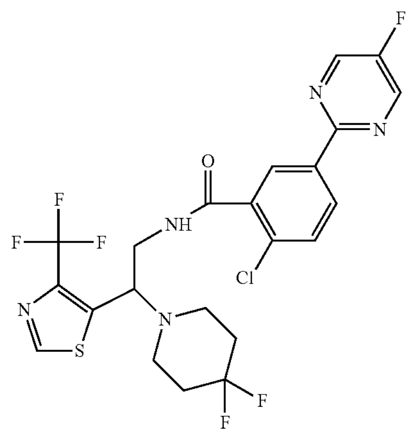 [SMILES: O=C(NCC(c1scnc1C(F)(F)F)N1CCC(F)(F)CC1)c1cc(-c2ncc(F)cn2)ccc1Cl] |
| 69 | A0018_76_01 | 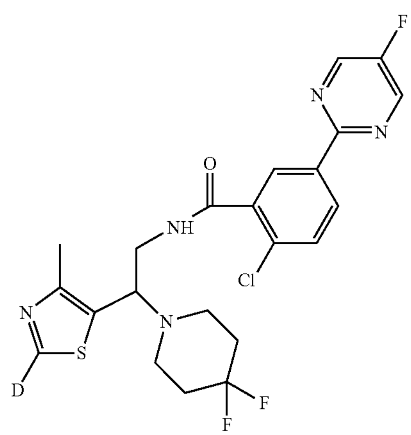 [SMILES: [2H]c1nc(C)c(C(CNC(=O)c2cc(-c3ncc(F)cn3)ccc2Cl)N2CCC(F)(F)CC2)s1] |
| 70 | A0017_81_02 | 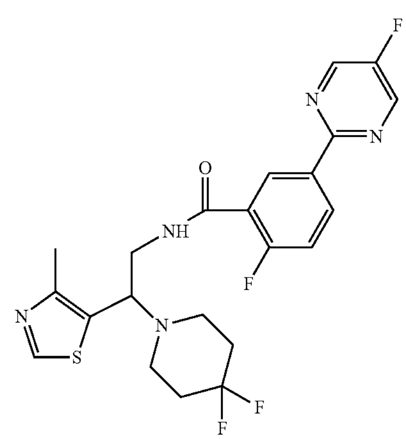 [SMILES: Cc1ncsc1C(CNC(=O)c1cc(-c2ncc(F)cn2)ccc1F)N1CCC(F)(F)CC1] |

-continued
| Compound | Code | Structure |
|---|---|---|
| 71 | A0017_81_03 | 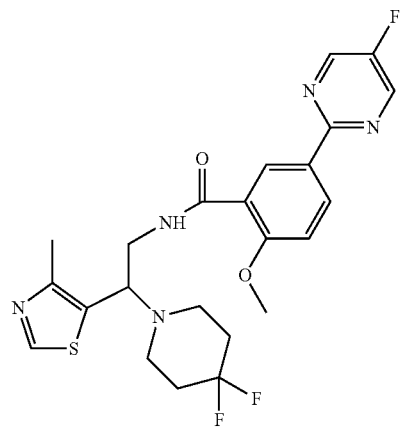 [SMILES: COc1ccc(-c2ncc(F)cn2)cc1C(=O)NCC(c1scnc1C)N1CCC(F)(F)CC1] |
| 72 | A0017_85_01 | 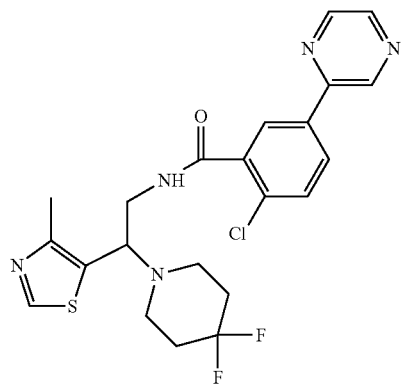 [SMILES: Cc1ncsc1C(CNC(=O)c1cc(-c2cnccn2)ccc1Cl)N1CCC(F)(F)CC1] |
| 73 | A0017_83_01 | 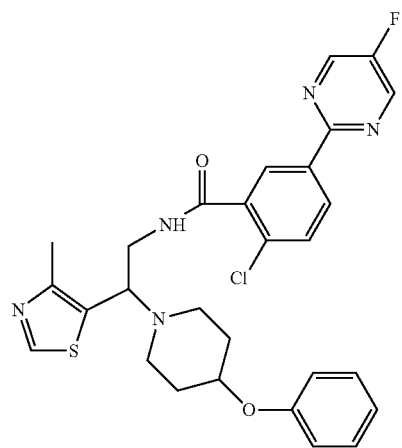 [SMILES: Cc1ncsc1C(CNC(=O)c1cc(-c2ncc(F)cn2)ccc1Cl)N1CCC(Oc2ccccc2)CC1] |

-continued

| Compound | Code | Structure |
|---|---|---|
| 74 | A0018_69_01 | 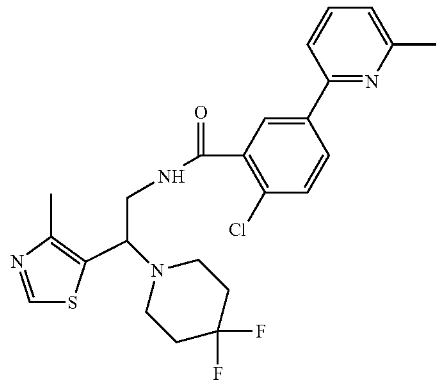 [SMILES: Cc1cccc(-c2ccc(Cl)c(C(=O)NCC(c3scnc3C)N3CCC(F)(F)CC3)c2)n1] |
| 75 | A0011_65_01 (trifluoroacetate salt) | CHIRAL 1 |
| 76 | A0011_65_02 (trifluoroacetate salt) | CHIRAL2 |

| Compound | Code | Structure |
|---|---|---|
| 77 | A0018_81_01 | 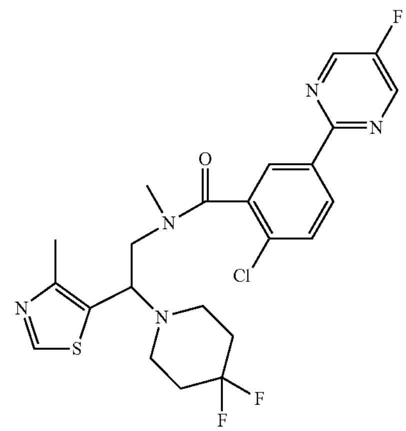 [SMILES: Cc1ncsc1C(CN(C)C(=O)c1cc(-c2ncc(F)cn2)ccc1Cl)N1CCC(F)(F)CC1] |
| 78 | A0018_89_01 | 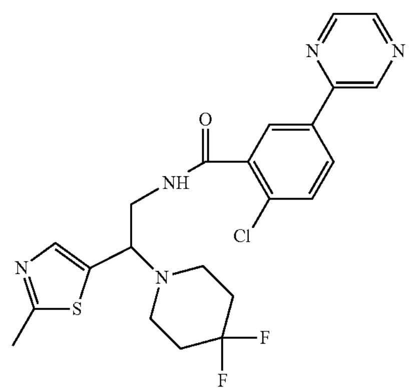 [SMILES: Cc1ncc(C(CNC(=O)c2cc(-c3cnccn3)ccc2Cl)N2CCC(F)(F)CC2)s1] |
| 79 | A0018_89_02 | 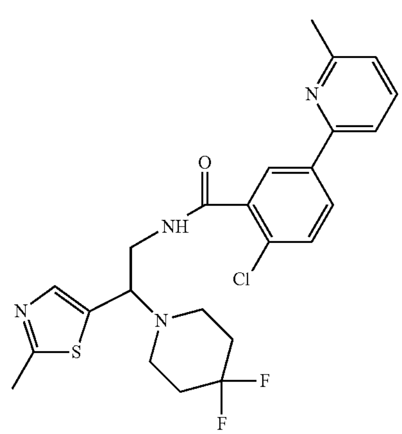 [SMILES: Cc1cccc(-c2ccc(Cl)c(C(=O)NCC(c3cnc(C)s3)N3CCC(F)(F)CC3)c2)n1] |

-continued

| Compound | Code | Structure |
|---|---|---|
| 80 | A0018_88_01 | 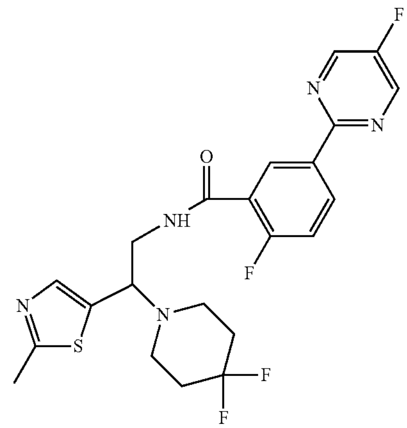 [SMILES: Cc1ncc(C(CNC(=O)c2cc(-c3ncc(F)cn3)ccc2F)N2CCC(F)(F)CC2)s1] |
| 81 | A0018_95_01 | 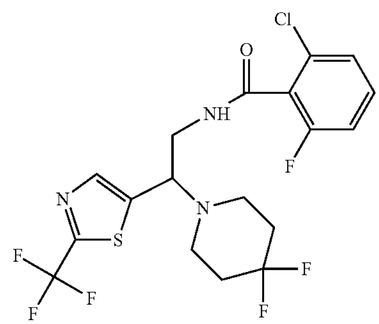 [SMILES: O=C(NCC(c1cnc(C(F)(F)F)s1)N1CCC(F)(F)CC1)c1c(F)cccc1Cl] |
| 82 | A0018_94_01 | 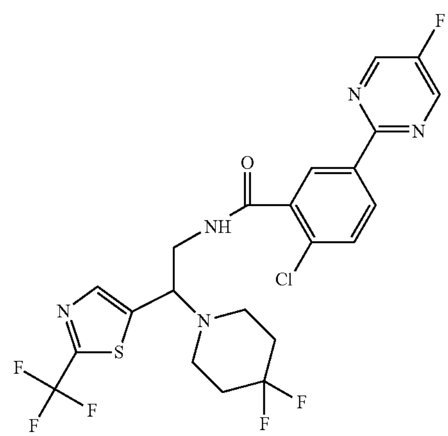 [SMILES: O=C(NCC(c1cnc(C(F)(F)F)s1)N1CCC(F)(F)CC1)c1cc(-c2ncc(F)cn2)ccc1Cl] |
| 83 | A0020_21_02 | 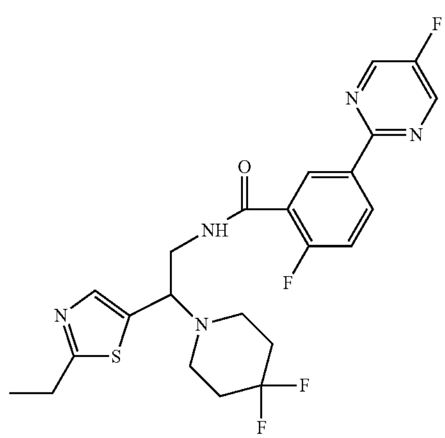 [SMILES: CCc1ncc(C(CNC(=O)c2cc(-c3ncc(F)cn3)ccc2F)N2CCC(F)(F)CC2)s1] |

-continued

| Compound | Code | Structure |
|---|---|---|
| 84 | A0020_21_01 | 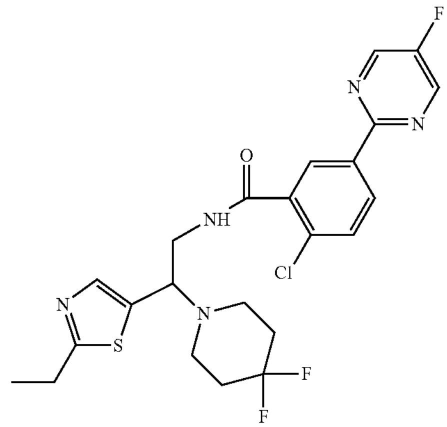 [SMILES: CCc1ncc(C(CNC(=O)c2cc(-c3ncc(F)cn3)ccc2Cl)N2CCC(F)(F)CC2)s1] |
| 85 | A0020_20_01 | 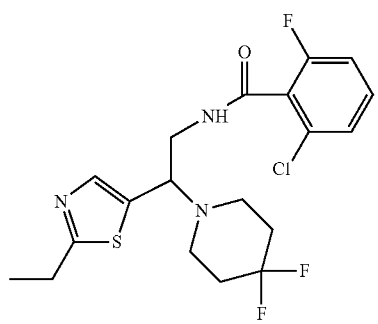 [SMILES: CCc1ncc(C(CNC(=O)c2c(F)cccc2Cl)N2CCC(F)(F)CC2)s1] |
| 86 | A0020_28_01 | 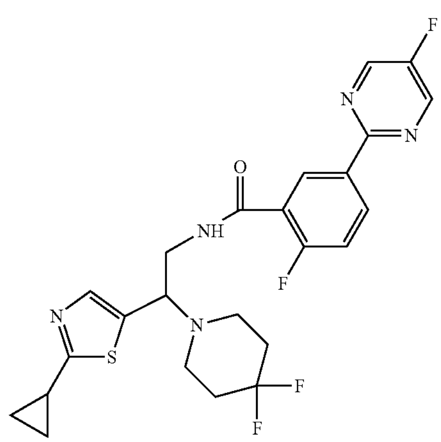 [SMILES: O=C(NCC(c1cnc(C2CC2)s1)N1CCC(F)(F)CC1)c1cc(-c2ncc(F)cn2)ccc1F] |

-continued
| Compound | Code | Structure |
|---|---|---|
| 87 | A0021_17_01 | 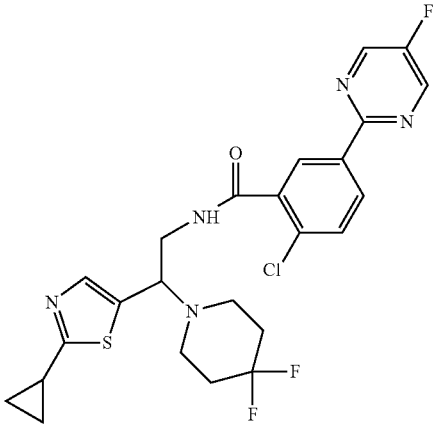 [SMILES: O=C(NCC(c1cnc(C2CC2)s1)N1CCC(F)(F)CC1)c1cc(-c2ncc(F)cn2)ccc1Cl] |
| 88 | A0020_27_01 | 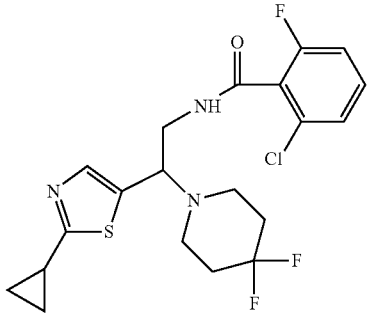 [SMILES: O=C(NCC(c1cnc(C2CC2)s1)N1CCC(F)(F)CC1)c1c(F)cccc1Cl] |
| 89 | A0021_24_01 | 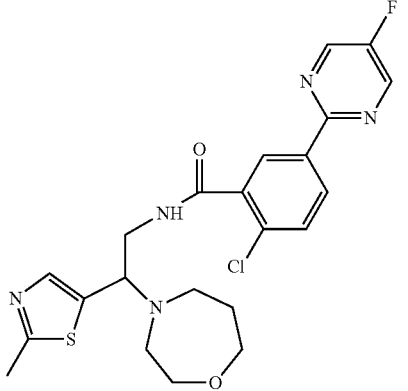 [SMILES: Cc1ncc(C(CNC(=O)c2cc(-c3ncc(F)cn3)ccc2Cl)N2CCCOCC2)s1] |
| 90 | A0021_07_11 | 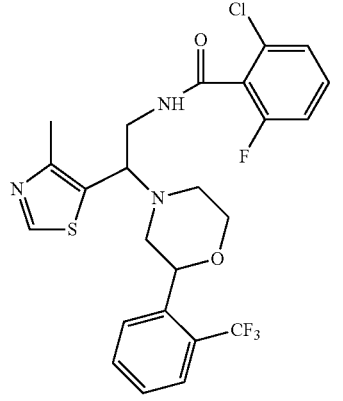 [SMILES: Cc1ncsc1C(CNC(=O)c1c(F)cccc1Cl)N1CCOC(c2ccccc2C(F)(F)F)C1] |

-continued
| Compound | Code | Structure |
|---|---|---|
| 91 | A0021_07_22 | 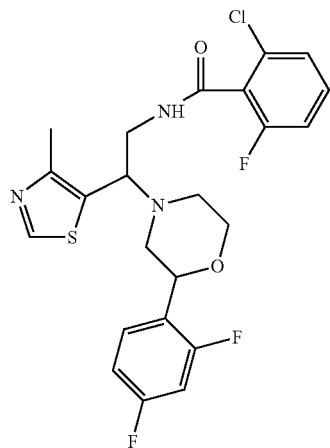 [SMILES: Cc1ncsc1C(CNC(=O)c1c(F)cccc1Cl)N1CCOC(c2ccc(F)cc2F)C1] |
| 92 | A0021_07_44 | 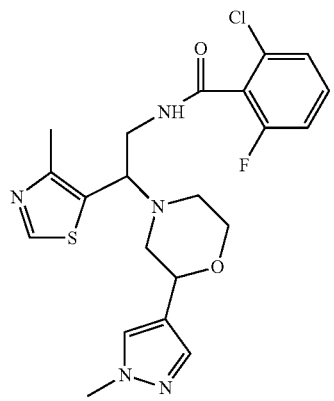 [SMILES: Cc1ncsc1C(CNC(=O)c1c(F)cccc1Cl)N1CCOC(c2cnn(C)c2)C1] |
| 93 | A0021_09_01 | 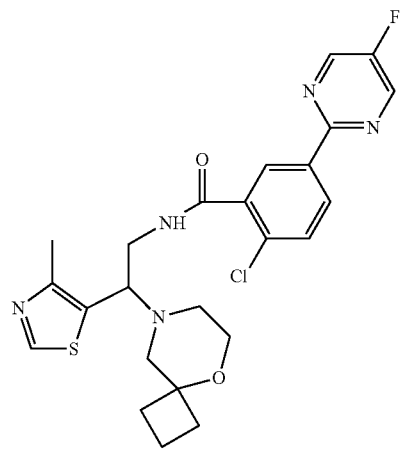 [SMILES: Cc1ncsc1C(CNC(=O)c1cc(-c2ncc(F)cn2)ccc1Cl)N1CCOC2(CCC2)C1] |

-continued

| Compound | Code | Structure |
|---|---|---|
| 94 | A0021_09_02 | 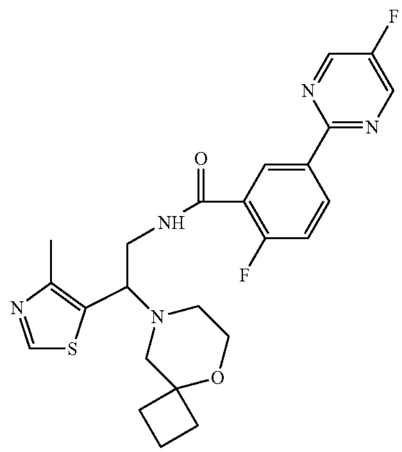 [SMILES: Cc1ncsc1C(CNC(=O)c1cc(-c2ncc(F)cn2)ccc1F)N1CCOC2(CCC2)C1] |
| 95 | A0021_11_01 (trifluoroacetate salt) | 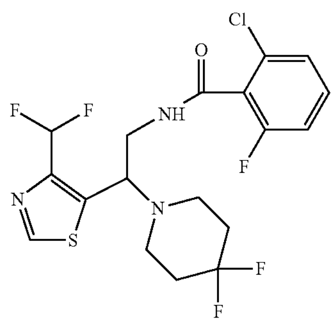 [SMILES: O=C(NCC(c1scnc1C(F)F)N1CCC(F)(F)CC1)c1c(F)cccc1Cl] |
| 96 | A0021_07_33 | 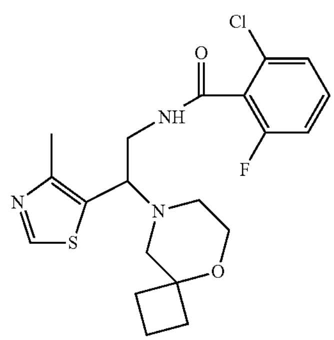 [SMILES: Cc1ncsc1C(CNC(=O)c1c(F)cccc1Cl)N1CCOC2(CCC2)C1] |
| 97 | A0021_10_01 | 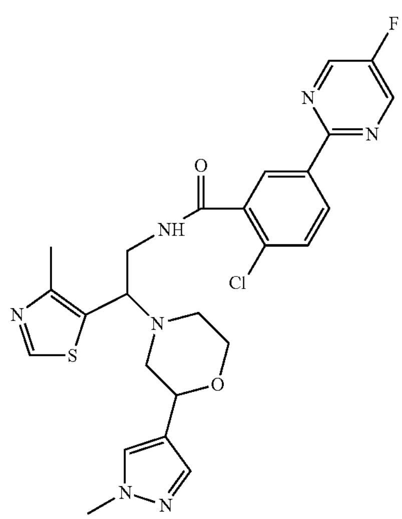 [SMILES: Cc1ncsc1C(CNC(=O)c1cc(-c2ncc(F)cn2)ccc1Cl)N1CCOC(c2cnn(C)c2)C1] |

-continued
| Compound | Code | Structure |
|---|---|---|
| 98 | A0021_10_02 | 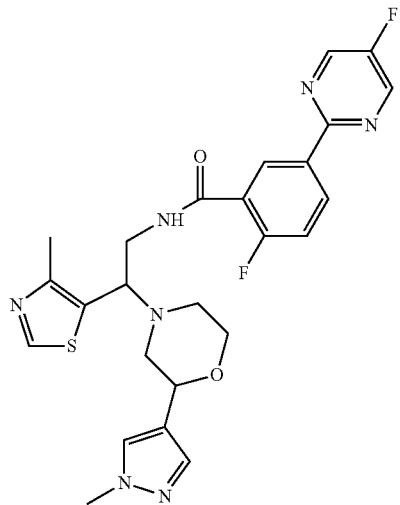 [SMILES: Cc1ncsc1C(CNC(=O)c1cc(-c2ncc(F)cn2)ccc1F)N1CCOC(c2cnn(C)c2)C1] |
| 99 | A0021_26_02 | 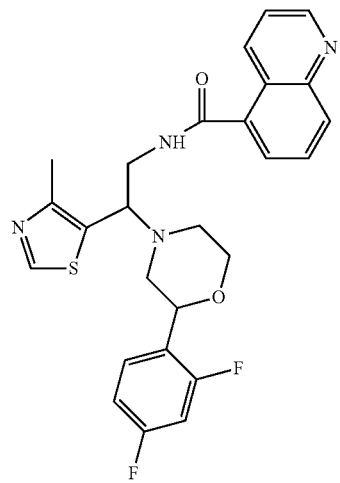 [SMILES: Cc1ncsc1C(CNC(=O)c1cccc2ncccc12)N1CCOC(c2ccc(F)cc2F)C1] |
| 100 | A0021_26_03 (single diastereoisomer) | 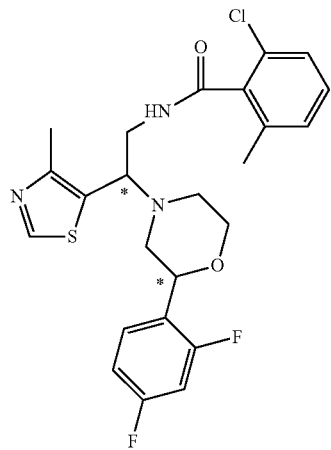 [SMILES: Cc1cccc(Cl)c1C(=O)NCC(c1scnc1C)N1CCOC(c2ccc(F)cc2F)C1] |

-continued
| Compound | Code | Structure |
|---|---|---|
| 101 | A0021_26_04 | 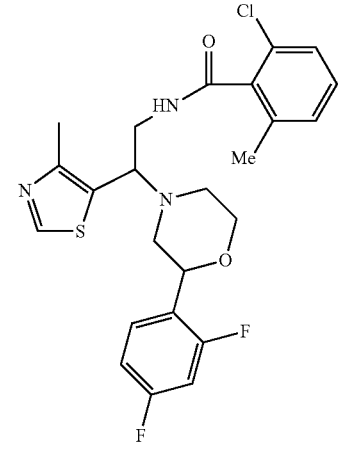 [SMILES: Cc1cccc(Cl)c1C(=O)NCC(c1scnc1C)N1CCOC(c2ccc(F)cc2F)C1] |
| 102 | A0021_24_04 (trifluoroacetate salt) | 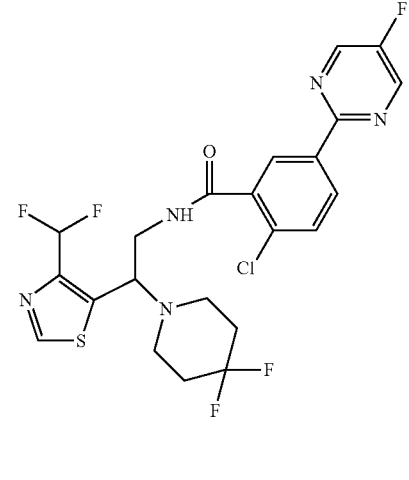 [SMILES: O=C(NCC(c1scnc1C(F)F)N1CCC(F)(F)CC1)c1cc(-c2ncc(F)cn2)ccc1Cl] |
| 103 | A0021_24_02 (trifluoroacetate salt) | 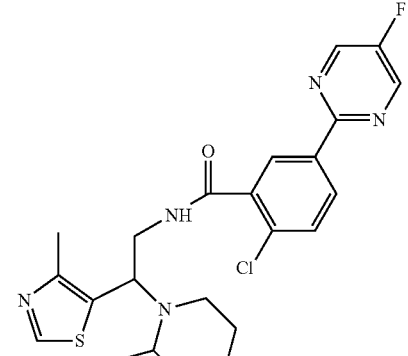 |

-continued

| Compound | Code | Structure |
|---|---|---|
| 104 | A0021_25_02 (trifluoroacetate salt) | 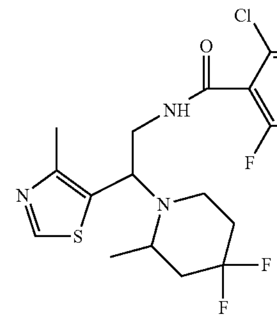 |
| 105 | A0021_38_01 | 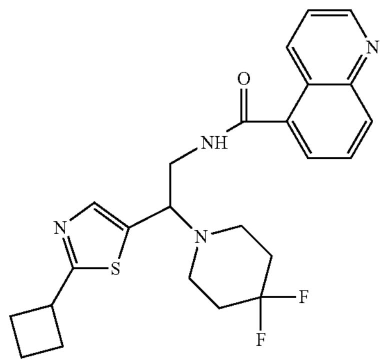 [SMILES: O=C(NCC(c1cnc(C2CCC2)s1)N1CCC(F)(F)CC1)c1cccc2ncccc12] |
| 106 | A0021_38_02 | 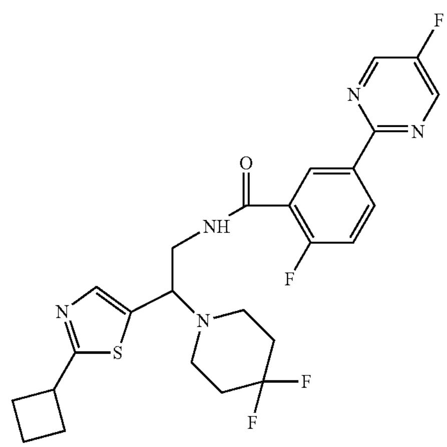 [SMILES: O=C(NCC(c1cnc(C2CCC2)s1)N1CCC(F)(F)CC1)c1cc(-c2ncc(F)cn2)ccc1F] |
| 107 | A0021_39_01 | 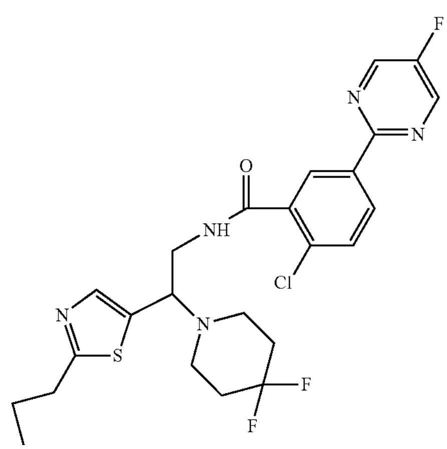 [SMILES: CCCc1ncc(C(CNC(=O)c2cc(-c3ncc(F)cn3)ccc2Cl)N2CCC(F)(F)CC2)s1] |

-continued

| Compound | Code | Structure |
|---|---|---|
| 108 | A0021_39_02 | 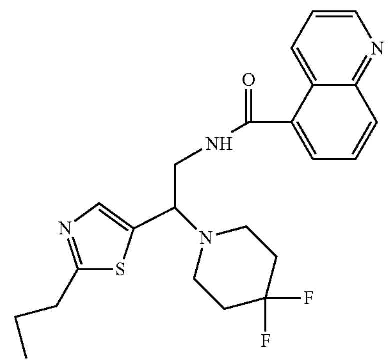 [SMILES: CCCc1ncc(C(CNC(=O)c2cccc3ncccc23)N2CCC(F)(F)CC2)s1] |
| 109 | A0021_40_01 | 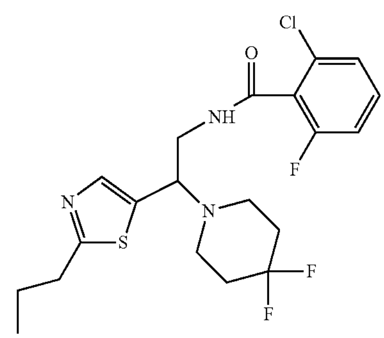 [SMILES: CCCc1ncc(C(CNC(=O)c2c(F)cccc2Cl)N2CCC(F)(F)CC2)s1] |
| 110 | A0020_68_01 | 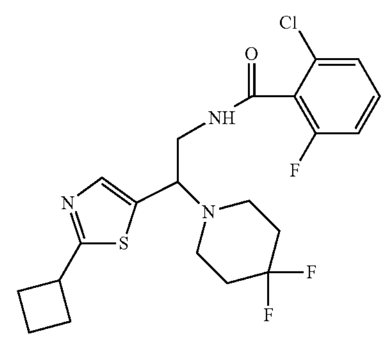 [SMILES: O=C(NCC(c1cnc(C2CCC2)s1)N1CCC(F)(F)CC1)c1c(F)cccc1Cl] |
| 111 | A0020_67_01 | 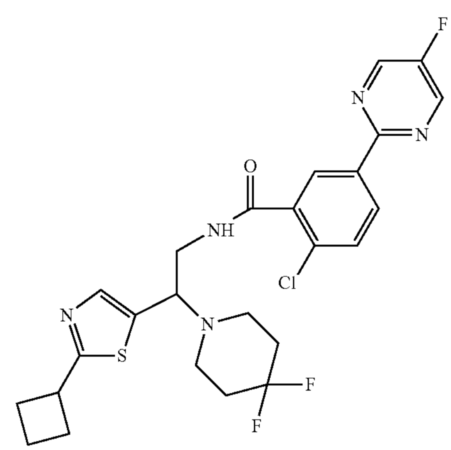 |

-continued

| Compound | Code | Structure |
|---|---|---|
| 112 | A0020_71_01 | 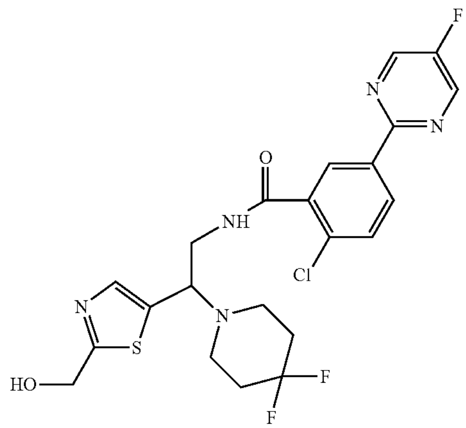 [SMILES: O=C(NCC(c1cnc(CO)s1)N1CCC(F)(F)CC1)c1cc(-c2ncc(F)cn2)ccc1Cl] |
| 113 | A0020_32_01 (trifluoroacetate salt) | 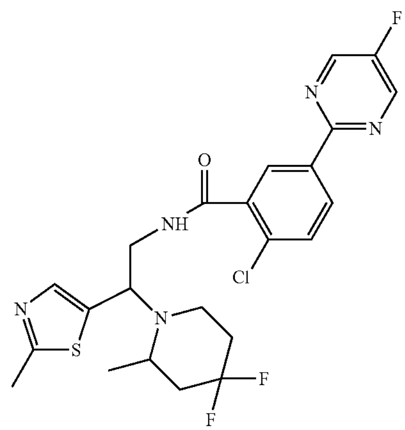 [SMILES: Cc1ncc(C(CNC(=O)c2cc(-c3ncc(F)cn3)ccc2Cl)N2CCC(F)(F)CC2C)s1] |
| 114 | A0016_60_01 | 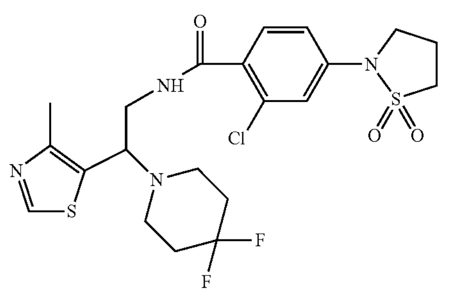 [SMILES: Cc1ncsc1C(CNC(=O)c1ccc(N2CCCS2(=O)=O)cc1Cl)N1CCC(F)(F)CC1] |
| 115 | A0016_54_01 | 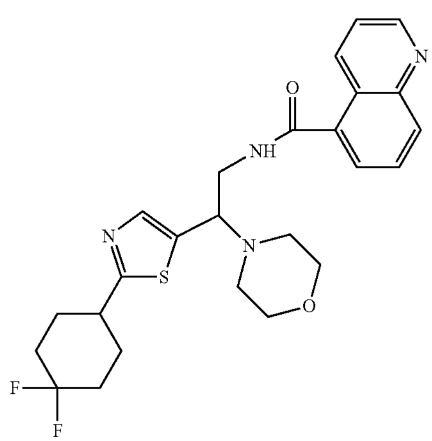 [SMILES: O=C(NCC(c1cnc(C2CCC(F)(F)CC2)s1)N1CCOCC1)c1cccc2ncccc12] |

-continued

| Compound | Code | Structure |
|---|---|---|
| 116 | A0016_52_01 | 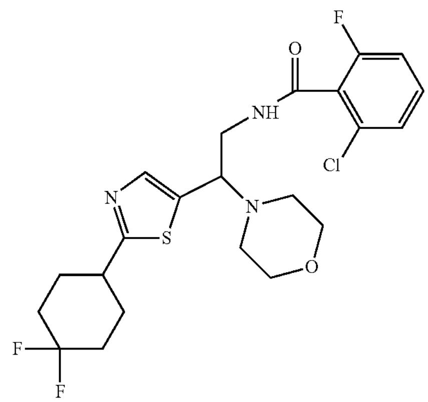 [SMILES: O=C(NCC(c1cnc(C2CCC(F)(F)CC2)s1)N1CCOCC1)c1c(F)cccc1Cl] |
| 117 | A0016_49_01 | 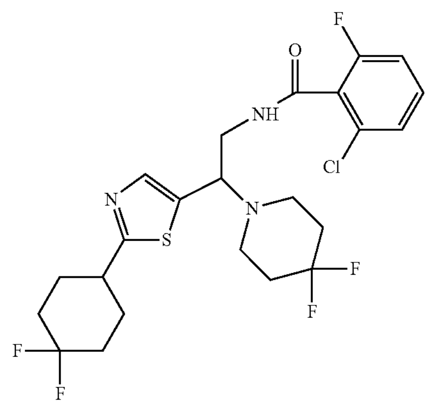 [SMILES: O=C(NCC(c1cnc(C2CCC(F)(F)CC2)s1)N1CCC(F)(F)CC1)c1c(F)cccc1Cl] |
| 118 | A0016_63_01 | 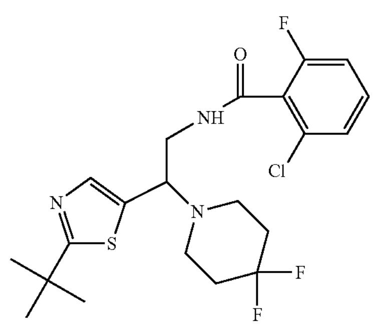 [SMILES: CC(C)(C)c1ncc(C(CNC(=O)c2c(F)cccc2Cl)N2CCC(F)(F)CC2)s1] |
| 119 | A0016_67_01 | 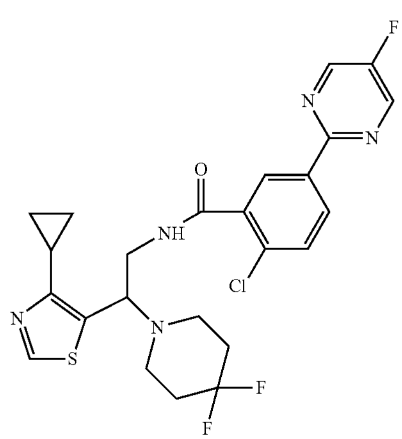 [SMILES: O=C(NCC(c1scnc1C1CC1)N1CCC(F)(F)CC1)c1cc(-c2ncc(F)cn2)ccc1Cl] |

-continued

| Compound | Code | Structure |
|---|---|---|
| 120 | A0016_61_01 | 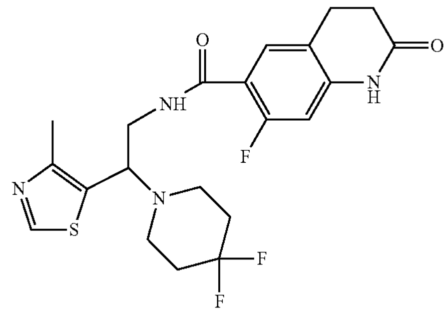 [SMILES: Cc1ncsc1C(CNC(=O)c1cc2c(cc1F)NC(=O)CC2)N1CCC(F)(F)CC1] |
| 121 | A0016_68_01 | 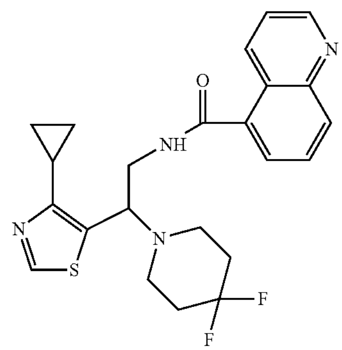 [SMILES: O=C(NCC(c1scnc1C1CC1)N1CCC(F)(F)CC1)c1cccc2ncccc12] |
| 122 | A0016_64_01 | 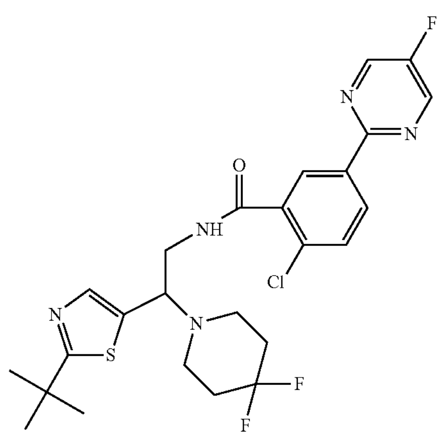 [SMILES: CC(C)(C)c1ncc(C(CNC(=O)c2cc(-c3ncc(F)cn3)ccc2Cl)N2CCC(F)(F)CC2)s1] |
| 123 | A0016_66_01 | 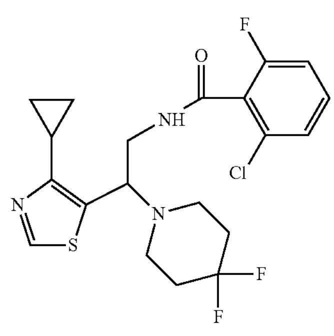 [SMILES: O=C(NCC(c1scnc1C1CC1)N1CCC(F)(F)CC1)c1c(F)cccc1Cl] |

-continued

| Compound | Code | Structure |
|---|---|---|
| 124 | A0016_65_01 | *N-[2-(2-tert-butyl-1,3-thiazol-5-yl)-2-(4,4-difluoropiperidin-1-yl)ethyl]quinoline-5-carboxamide* |
| 125 | A0016_53_01 | *2-chloro-N-{2-[2-(4,4-difluorocyclohexyl)-1,3-thiazol-5-yl]-2-(morpholin-4-yl)ethyl}-5-(5-fluoropyrimidin-2-yl)benzamide* |
| 126 | A0016_50_01 | *2-chloro-N-{2-[2-(4,4-difluorocyclohexyl)-1,3-thiazol-5-yl]-2-(4,4-difluoropiperidin-1-yl)ethyl}-5-(5-fluoropyrimidin-2-yl)benzamide* |

-continued

| Compound | Code | Structure |
|---|---|---|
| 127 | AXX0013_0422_003_01 | 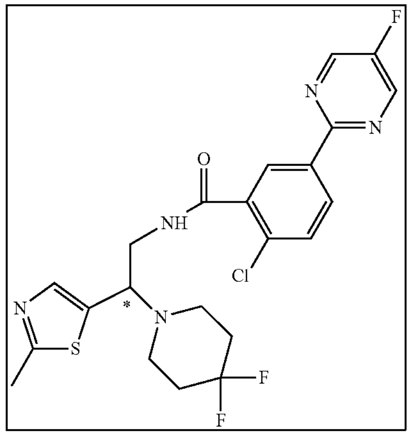 [SMILES: Cc1ncc(C(CNC(=O)c2cc(-c3ncc(F)cn3)ccc2Cl)N2CCC(F)(F)CC2)s1] |
| 128 | AXX0013_0422_003_02 | 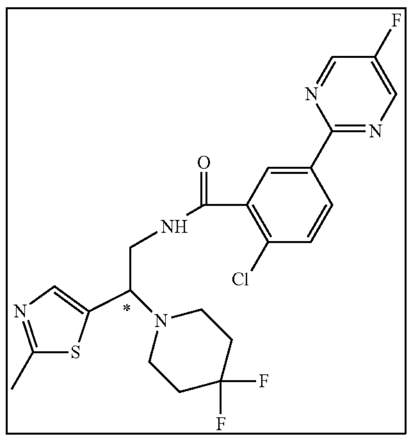 [SMILES: Cc1ncc(C(CNC(=O)c2cc(-c3ncc(F)cn3)ccc2Cl)N2CCC(F)(F)CC2)s1] |
| 129 | A0016_99_01 | 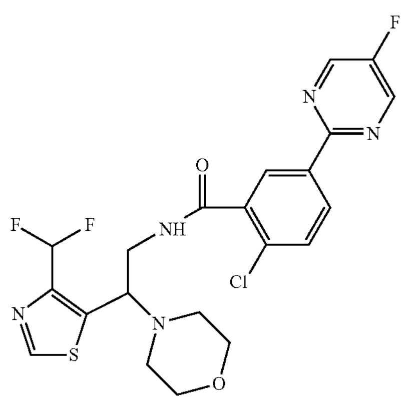 [SMILES: O=C(NCC(c1scnc1C(F)F)N1CCOCC1)c1cc(-c2ncc(F)cn2)ccc1Cl] |
| 130 | A0022_02_01 | 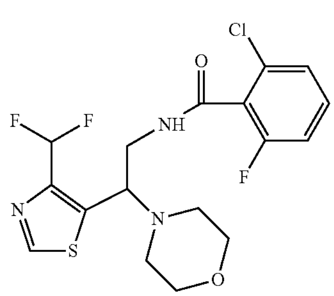 [SMILES: O=C(NCC(c1scnc1C(F)F)N1CCOCC1)c1c(F)cccc1Cl] |

Analytical Part
System Purification
HPLC-MS Preparative
HPLC system Waters with Pump Waters 2525, Sample Manager Waters 2767, Column fluidic organizer with 515 LC Pump, PDA Waters 2996 and mass spectrometer ZQ Micromass with ESI source and single quadrupole detector. Two mobile phases were used, mobile phase A: water (MilliQ) 0.1% TFA; mobile phase B: acetonitrile (Chromasolv Sigma-Aldrich) 0.1% TFA, and the run gradient conditions were set specifically for each compound. Two preparative columns were used: X-Bridge $C_{18}$ Waters 100×19 mm 5 μm for lipophilic compounds and Atlantis $C_{18}$ Waters 100×19 mm 5 μm for very polar compounds. An injection volume between 20 and 900 μl was used and the flow was 20 ml/minutes. The removal of counterion was performed by using the PL-$HCO_3$ MP cartridge, a quaternary amine SAX ($HCO_3^-$ form) device for the removal of TFA from HPLC eluents and the freebasing of TFA salts. The freeze-drying was carried out in the Martin Christ system.

Racemate Separations

Method 1: Compound 34 racemate was processed using an Agilent 1100 module comprising a quaternary pump with degasser, an autosampler, a column oven (set at 40° C.), a diode-array detector DAD (wavelength used 220 nm), in order to collect both enantiomers with enough purity. Reversed phase HPLC semipreparative was carried out on a Chiral C18 column Cyclobond I 2000 HP-RSI Supelco (5 μm, 4.6×150 mm) with a flow rate of 1.2 ml/min. Two mobile phases were used, mobile phase A: water (MilliQ) 0.1% TFA; mobile phase B: acetonitrile (Chromasolv Sigma-Aldrich) 0.1% TFA, and they were employed to performed an isocratic run with 10% B for 20 minutes. An injection volume of 20 μl was used of a solution 2.2 mg/mL.

Method 2: Compound 34 racemate was optionally processed using an WATERS Quaternary Gradient Mobile 2535 equipped with WATERS UV/Visible Detector 2489 (dual-wavelength used 240 and 360 nm), in order to collect both enantiomers with enough purity. Normal phase HPLC analytical was carried out on a Chiral Kromasil 5-Amycoat column (5 μm, 4.6×250 mm) with a flow rate of 1.0 ml/min. Two mobile phases were used, mobile phase A: Hexane (Chromasolv for HPLC Sigma-Aldrich); mobile phase B: isopropanol (Chromasolv for HPLC Sigma-Aldrich), and they were employed to performed an isocratic run with 40% B for 20 minutes. An injection volume of 100 μl was used of a solution 10.0 mg/mL.

Method 3: Compound 61 racemate was processed using an WATERS Quaternary Gradient Mobile 2535 equipped with WATERS UV/Visible Detector 2489 (dual-wavelength used 240 and 360 nm), in order to collect both enantiomers with enough purity. Normal phase HPLC analytical was carried out on a Chiral Kromasil 5-Amycoat column (5 μm, 4.6×250 mm) with a flow rate of 1.0 ml/min. Two mobile phases were used, mobile phase A: Hexane (Chromasolv for HPLC Sigma-Aldrich); mobile phase B: ethanol (Chromasolv for HPLC Sigma-Aldrich), and they were employed to performed an isocratic run with 15% B for 90 minutes. An injection volume of 100 μl was used of a solution 10.0 mg/mL.

Compounds 75 and 76 were obtained as single enantiomer from racemate 34.

Compounds 127 and 128 were obtained as single enantiomer from racemate 61.

LCMS
LCMS General Procedure

The HPLC measurement was performed using an Agilent 1100 module comprising a quaternary pump with degasser, an autosampler, a column oven (set at 40° C.), a diode-array detector DAD (wavelength used 215 nm) and a column as specified in the respective methods below. Flow from the column was split to a MS spectrometer. The MS detector (ion trap analyzer Esquire 3000 plus Bruker) was configured with an electrospray ionization source. Mass spectra were acquired by scanning from 50 to 1500 in 0.2 second. The capillary needle voltage was 4 kV in positive ionization mode and the source temperature was maintained at 365° C. Nitrogen was used as the nebulizer gas, the flow was 10 l/min. Data acquisition was performed with Data Analysis Bruker Program.

LCMS—Procedure 1

In addition to general procedure: Reversed phase HPLC was carried out on a Discovery C18 column Supelco (5 μm, 4.6×150 mm) with a flow rate of 1.0 ml/min. Two mobile phases were used, mobile phase A: water (MilliQ) 0.05% TFA; mobile phase B: acetonitrile (Chromasolv Sigma-Aldrich) 0.05% TFA, and they were employed to run a gradient conditions from 20% B to 90% in 15 minutes, 100% B in 0.9 minutes and 20% B in 0.1 minutes and hold these conditions for 4 minutes in order to reequilibrate the column. An injection volume of 5 μl was used.

LCMS—Procedure 2

In addition to general procedure: Reversed phase HPLC was carried out on a Discovery C18 column Supelco (5 μm, 4.6×150 mm) with a flow rate of 1.0 ml/min. Two mobile phases were used, mobile phase A: water (MilliQ) 0.05% TFA; mobile phase B: acetonitrile (Chromasolv Sigma-Aldrich) 0.05% TFA, and they were employed to run a gradient conditions from 5% B to 50% in 15 minutes, 100% B in 0.9 minutes and 5% B in 0.1 minutes and hold these conditions for 4 minutes in order to reequilibrate the column. An injection volume of 5 μl was used LCMS—Procedure 3

In addition to general procedure: Reversed phase HPLC was carried out on a Atlantis C18 column Waters (3 μm, 4.6×100 mm) with a flow rate of 1.0 ml/min. Two mobile phases were used, mobile phase A: water (MilliQ) 0.05% TFA; mobile phase B: acetonitrile (Chromasolv Sigma-Aldrich) 0.05% TFA, and they were employed to run a gradient conditions from 0% B to 30% in 12 minutes, 50% B in 0.9 minutes and 0% B in 0.1 minutes and hold these conditions for 3 minutes in order to reequilibrate the column. An injection volume of 5 μl was used.

LCMS—Procedure 4

In addition to general procedure: Reversed phase HPLC was carried out on a Chiral C18 column Cyclobond I 2000 HP-RSI Supelco (5 μm, 4.6×150 mm) with a flow rate of 1.0 ml/min. Two mobile phases were used, mobile phase A: water (MilliQ) 0.1% TFA; mobile phase B: acetonitrile (Chromasolv Sigma-Aldrich) 0.1% TFA, and they were employed to run a gradient conditions from 10% B to 20% in 15 minutes. An injection volume of 5 μl was used.

LCMS—Procedure 5

In addition to general procedure: Reversed phase HPLC was carried out on a Ascentis-Express column (3 μm, 4.6×150 mm) with a flow rate of 1.0 ml/min. Two mobile phases were used, mobile phase A: water (MilliQ) 0.1% TFA; mobile phase B: acetonitrile (Chromasolv Sigma-Aldrich) 0.1% TFA, and they were employed to run a gradient conditions from 10% B to 20% in 15 minutes. An injection volume of 5 μl was used.

TABLE F-3

Retention time ($R_t$) in minutes, [M + H]+ peak, LCMS procedure

| Cmpd | $R_t$ | [M + H]+ | LCMS procedure |
|---|---|---|---|
| 1 | 6.8 | 416 | 1 |
| 2 | 8.3 | 404 | 1 |
| 3 | 8.9 | 370 | 2 |
| 4 | 10.1 | 404 | 2 |
| 5 | 8.1 | 371 | 2 |
| 6 | 12.1 | 416 | 2 |
| 7 | 9.6 | 384 | 3 |
| 8 | 11.6 | 404 | 2 |
| 9 | 5.5 | 416 | 1 |
| 10 | 7.3 | 370 | 2 |
| 11 | 3.4 | 346 | 1 |
| 12 | 7 | 367 | 3 |
| 13 | 3.4 | 366 | 1 |
| 14 | 5.7 | 380 | 1 |
| 15 | 7.3 | 400 | 1 |
| 16 | 9.6 | 401 | 2 |
| 17 | 4.9 | 413 | 1 |
| 18 | 6.2 | 392 | 1 |
| 19 | 6.4 | 412 | 1 |
| 20 | 8 | 482 | 1 |
| 21 | 6.4 | 412 | 1 |
| 22 | 5.7 | 388 | 1 |
| 23 | 7.2 | 450 | 1 |
| 24 | 7.4 | 470 | 1 |
| 25 | 7.2 | 475 | 1 |
| 26 | 7.2 | 436 | 1 |
| 27 | 7.1 | 460 | 1 |
| 28 | 3.8 | 368 | 1 |
| 29 | 6.4 | 430 | 1 |
| 30 | 6.1 | 406 | 1 |
| 31 | 11.9 | 418 | 2 |
| 32 | 6 | 394 | 1 |
| 33 | 7.8 | 417 | 2 |
| 34 | 7.5 | 496 | 1 |
| 35 | 8.2 | 384 | 2 |
| 36 | 3.8 | 360 | 1 |
| 37 | 5.3 | 462 | 1 |
| 38 | 6.4 | 418 | 1 |
| 39 | 6.9 | 414 | 1 |
| 40 | 6.6 | 394 | 1 |
| 41 | 6.5 | 426 | 1 |
| 42 | 6.3 | 406 | 1 |
| 43 | 6.1 | 430 | 1 |
| 44 | 7.6 | 354 | 2 |
| 45 | 6.3 | 388 | 1 |
| 46 | 5.8 | 364 | 1 |
| 47 | 7.3 | 466 | 1 |
| 48 | 6.2 | 400 | 1 |
| 49 | 5.7 | 376 | 1 |
| 50 | 11 | 410 | 2 |
| 51 | 12.8 | 480 | 2 |
| 52 | 5.1 | 402 | 1 |
| 53 | 8.5 | 376 | 2 |
| 54 | 10.4 | 446 | 2 |
| 55 | 3.1 | 368 | 1 |
| 56 | 12 | 422 | 2 |
| 57 | 7 | 492 | 1 |
| 58 | 12.7 | 494 | 2 |
| 59 | 7.2 | 488 | 1 |
| 60 | 7.1 | 474 | 1 |
| 61 | 7.9 | 496 | 1 |
| 62 | 7.6 | 488 | 1 |
| 63 | 6.8 | 458 | 1 |
| 64 | 7.8 | 418 | 1 |
| 65 | 8.9 | 468 | 1 |
| 66 | 9.5 | 496 | 1 |
| 67 | 11.3 | 472 | 1 |
| 68 | 12.6 | 550 | 1 |
| 69 | 7.6 | 495 | 1 |
| 70 | 14 | 480 | 2 |
| 71 | 13.9 | 492 | 2 |
| 72 | 11.6 | 478 | 2 |
| 73 | 13.3 | 552 | 2 |
| 74 | 4.7 | 491 | 1 |
| 75 | 11.7 | 496 | 4 |
| 76 | 12.3 | 496 | 4 |
| 77 | 9.0 | 510 | 1 |
| 78 | 6.3 | 478 | 1 |
| 79 | 5.0 | 491 | 1 |
| 80 | 7.9 | 480 | 1 |
| 81 | 12.1 | 472 | 1 |
| 82 | 13.1 | 550 | 1 |
| 83 | 8.7 | 494 | 1 |
| 84 | 8.6 | 510 | 1 |
| 85 | 7.3 | 432 | 1 |
| 86 | 9.0 | 506 | 1 |
| 87 | 8.9 | 522 | 1 |
| 88 | 7.6 | 444 | 1 |
| 89 | 5.2 | 476 | 1 |
| 90 | 9.7 | 528 | 1 |
| 91 | 8.8 | 496 | 1 |
| 92 | 9.2 | 464 | 2 |
| 93 | 7.2 | 502 | 1 |
| 94 | 7.3 | 486 | 1 |
| 95 | 9.7 | 454 | 1 |
| 96 | 5.4 | 424 | 1 |
| 97 | 5.7 | 542 | 1 |
| 98 | 5.7 | 526 | 1 |
| 99 | 6.0 | 495 | 1 |
| 100 | 8.9 | 492 | 1 |
| 101 | 4.8 | 492 | 5 |
| 102 | 10.9 | 532 | 1 |
| 103 | 7.6 | 510 | 1 |
| 104 | 5.9 | 432 | 1 |
| 105 | 5.7 | 457 | 1 |
| 106 | 10.0 | 520 | 1 |
| 107 | 9.5 | 524 | 1 |
| 108 | 5.2 | 445 | 1 |
| 109 | 8.4 | 446 | 1 |
| 110 | 8.7 | 458 | 1 |
| 111 | 9.8 | 536 | 1 |
| 112 | 6.5 | 512 | 1 |
| 113 | 8.3 | 510 | 1 |
| 114 | 5.6 | 519 | 1 |
| 115 | 4.6 | 487 | 1 |
| 116 | 7.2 | 488 | 1 |
| 117 | 9.9 | 522 | 1 |
| 118 | 9.6 | 460 | 1 |
| 119 | 8.9 | 522 | 1 |
| 120 | 4.6 | 453 | 1 |
| 121 | 4.5 | 443 | 1 |
| 122 | 10.7 | 538 | 1 |
| 123 | 7.5 | 444 | 1 |
| 124 | 6.5 | 459 | 1 |
| 125 | 8.4 | 566 | 1 |
| 126 | 10.9 | 600 | 1 |
| 127 | 11.4 | 496 | 4 |
| 128 | 12.6 | 496 | 4 |
| 129 | 7.5 | 497 | 1 |
| 130 | 5.7 | 419 | 1 |

NMR Characterization

For a number of compounds $^1$H NMR spectra were recorded on a Bruker Avance 400 MHz spectrometer using DMSO-d6 or DMSO-d6 with a drop of trifluoroacetic acid as solvents. Chemical shifts (δ) are reported in parts per million (ppm) relative to tetramethylsilane (TMS), which was used as internal standard.

| Compound | ¹H-NMR 400 |
|---|---|
| A0013_29_01 | ¹H NMR (DMSO-d₆) δ: 8.88 (t, J = 5.5 Hz, 1H), 7.84 (d, J = 3.3 Hz, 1H), 7.71 (d, J = 3.3 Hz, 1H), 7.40-7.49 (m, 1H), 7.30-7.36 (m, 1H), 7.26 (t, J = 8.7 Hz, 1H), 7.06-7.14 (m, 3H), 7.00-7.07 (m, 1H), 4.42-4.51 (m, 1H), 3.90-4.03 (m, 2H), 3.85-3.90 (m, 2H), 2.89-2.99 (m, 1H), 2.79-2.86 (m, 2H), 2.70-2.78 (m, 1H) |
| A0013_29_03 | ¹H NMR (DMSO-d₆) δ: 9.36 (t, J = 5.5 Hz, 1H), 8.36 (d, J = 3.3 Hz, 1H), 8.25 (d, J = 3.3 Hz, 1H), 7.98 (td, J = 8.2, 6.4 Hz, 1H), 7.84-7.89 (m, 1H), 7.80 (t, J = 8.7 Hz, 1H), 4.94 (t, J = 6.8 Hz, 1H), 4.33-4.40 (m, 2H), 3.29-3.38 (m, 2H), 3.14-3.25 (m, 2H), 2.43-2.57 (m, 4H) |
| A0015_09_02 | ¹H NMR (DMSO-d₆) δ: 8.81 (t, J = 5.7 Hz, 1H), 7.82 (d, J = 3.3 Hz, 1H), 7.71 (d, J = 3.3 Hz, 1H), 7.47 (td, J = 8.2, 6.2 Hz, 1H), 7.32-7.38 (m, 1H), 7.28 (t, J = 8.3 Hz, 1H), 4.23 (t, J = 7.1 Hz, 1H), 3.79-3.86 (m, 2H), 3.58 (t, J = 4.5 Hz, 4H), 2.58-2.67 (m, 2H), 2.52-2.56 (m, 2H) |
| A0013_29_02 | ¹H NMR (DMSO-d₆) δ: 9.12 (s, 1H), 8.68 (t, J = 5.4 Hz, 1H), 7.65 (s, 1H), 7.46 (td, J = 8.2, 6.2 Hz, 1H), 7.32-7.38 (m, 1H), 7.24-7.32 (m, 1H), 4.16-4.31 (m, 1H), 3.91 (dt, J = 13.6, 6.8 Hz, 1H), 3.61-3.73 (m, 1H), 2.65-2.81 (m, 2H), 2.40-2.56 (m, 1H), 1.86-2.06 (m, 4H) |
| A0013_32_01 | ¹H NMR (DMSO-d₆) δ: 9.10 (s, 1H), 8.62 (t, J = 4.4 Hz, 1H), 7.58 (s, 1H), 7.45 (td, J = 8.3, 6.3 Hz, 1H), 7.30-7.35 (m, 1H), 7.26 (t, J = 8.6 Hz, 1H), 4.05 (t, J = 7.3 Hz, 1H), 3.81-3.92 (m, 1H), 3.65 (dt, J = 13.5, 6.5 Hz, 1H), 3.48-3.60 (m, 4H), 2.47-2.56 (m, 2H), 2.25-2.38 (m, 2H) |
| A0015_13_01 | ¹H NMR (DMSO-d₆) δ: 9.10 (d, J = 1.8 Hz, 1H), 8.69 (t, J = 5.7 Hz, 1H), 7.66 (d, J = 1.8 Hz, 1H), 7.42 (td, J = 8.2, 6.2 Hz, 1H), 7.27-7.32 (m, 1H), 7.23 (t, J = 8.6 Hz, 1H), 6.99-7.10 (m, 4H), 4.29 (t, J = 7.4 Hz, 1H), 3.87-3.98 (m, 2H), 3.73-3.84 (m, 2H), 3.58-3.66 (m, 1H), 2.83-2.92 (m, 1H), 2.71-2.83 (m, 2H), 2.45-2.49 (m, 1H) |
| A0015_28_03 | ¹H NMR (DMSO-d₆) δ: 9.05 (s, 1H), 8.83 (t, J = 5.5 Hz, 1H), 7.88 (s, 1H), 7.47 (td, J = 8.1, 6.4 Hz, 1H), 7.32-7.37 (m, 1H), 7.28 (t, J = 8.6 Hz, 1H), 4.35-4.48 (m, 1H), 3.75-3.87 (m, 1H), 3.56-3.73 (m, 5H), 2.76-2.89 (m, 2H), 2.61-2.76 (m, 2H), 1.80 (quin, J = 5.9 Hz, 2H) |
| A0015_10_02 | ¹H NMR (DMSO-d₆) δ: 9.07 (s, 1H), 8.81 (t, J = 5.4 Hz, 1H), 7.86 (s, 1H), 7.40-7.54 (m, 1H), 7.32-7.38 (m, 1H), 7.29 (t, J = 8.6 Hz, 1H), 4.33 (t, J = 7.3 Hz, 1H), 3.75-3.86 (m, 1H), 3.61 (dt, J = 13.3, 6.3 Hz, 1H), 2.58-2.69 (m, 2H), 2.40-2.48 (m, 2H), 1.88-2.04 (m, 4H) |
| A0015_12_01 | ¹H NMR (DMSO-d₆) δ: 9.07 (s, 1H), 8.85 (t, J = 5.7 Hz, 1H), 7.91 (s, 1H), 7.44 (td, J = 8.2, 6.2 Hz, 1H), 7.30-7.34 (m, 1H), 7.22-7.29 (m, 1H), 7.06-7.12 (m, 3H), 7.02-7.06 (m, 1H), 4.41 (t, J = 7.2 Hz, 1H), 3.91 (ddd, J = 13.3, 7.1, 5.8 Hz, 1H), 3.65-3.75 (m, 3H), 2.75-2.88 (m, 1H), 2.55-2.64 (m, 1H) |
| A0015_08_01 | ¹H NMR (DMSO-d₆) δ: 9.07 (s, 1H), 8.77 (t, J = 5.3 Hz, 1H), 7.82 (s, 1H). 7.46 (td, J = 8.4, 6.3 Hz, 1H), 7.34 (d, J = 8.1 Hz, 1H), 7.24-7.32 (m, 1H), 4.17 (t, J = 7.2 Hz, 1H), 3.83 (dt, J = 13.2, 6.4 Hz, 1H), 3.50-3.66 (m, 5H), 2.43-2.49 (m, 2H), 2.36-2.43 (m, 2H) |
| A0013_42_05 | ¹H NMR (DMSO-d₆) δ: 9.08 (s, 1H), 8.36 (t, J = 5.4 Hz, 1H), 7.84 (s, 1H), 7.14 (t, J = 7.6 Hz, 1H), 7.01 (d, J = 7.8 Hz, 2H), 4.26 (t, J = 7.4 Hz, 1H), 3.76 (ddd, J = 13.4, 7.6, 5.4 Hz, 1H), 3.54-3.64 (m, 5H), 2.44-2.50 (m, 2H), 2.28-2.39 (m, 2H), 2.14 (s, 6H) |
| A0013_42_04 | ¹H NMR (DMSO-d₆) δ: 9.06 (s, 1H), 8.27 (t, J = 5.5 Hz, 1H), 7.82 (s, 1H), 7.04 (d, J = 8.6 Hz, 1H), 6.57 (dd, J = 8.6, 2.5 Hz, 1H), 6.53 (d, J = 2.8 Hz, 1H), 5.37 (s, 2H), 4.18 (t, J = 7.2 Hz, 1H), 3.69-3.82 (m, 1H), 3.54-3.63 (m, 4H), 3.43-3.54 (m, 1H), 2.44-2.49 (m, 2H), 2.33-2.43 (m, 2H) |
| A0013_42_02 | ¹H NMR (DMSO-d₆) δ: 9.07 (s, 1H), 8.56 (t, J = 5.5 Hz, 1H), 7.84 (s, 1H), 7.25-7.29 (m, 2H), 7.16-7.21 (m, 1H), 4.23 (t, J = 7.4 Hz, 1H), 3.78 (ddd, J = 13.2, 7.3, 5.7 Hz, 1H), 3.49-3.66 (m, 5H), 2.43-2.49 (m, 2H), 2.30-2.41 (m, 2H), 2.18 (s, 3H) |
| A0013_55_05 | ¹H NMR (DMSO-d₆) δ: 9.08 (s, 1H), 8.32-8.50 (m, 1H), 7.88 (s, 1H), 7.07-7.23 (m, J = 7.6, 7.6 Hz, 1H), 6.96-7.07 (m, 2H), 4.33-4.52 (m, 1H), 3.70-3.81 (m, 1H), 3.58-3.70 (m, 1H), 2.59-2.73 (m, 2H), 2.37-2.48 (m, 2H), 2.16 (s, 6H), 1.89-2.06 (m, 4H) |
| A0013_55_02 | ¹H NMR (DMSO-d₆) δ: 9.09 (s, 1H), 8.62 (t, J = 5.5 Hz, 1H), 7.90 (s, 1H), 7.24-7.36 (m, 2H), 7.13-7.22 (m, 1H), 4.38-4.49 (m, 1H), 3.79 (dt, J = 12.5, 6.6 Hz, 1H), 3.65 (dt, J = 13.5, 6.6 Hz, 1H), 2.61-2.74 (m, 2H), 2.45-2.56 (m, 2H), 2.19 (s, 3H), 1.90-2.07 (m, 4H) |
| A0013_55_04 | ¹H NMR (DMSO-d₆ + TFA) δ: 9.13 (s, 1H), 8.44 (t, J = 5.1 Hz, 1H), 7.88-8.00 (m, 1H), 7.10 (d, J = 8.6 Hz, 1H), 6.67 (dd, J = 8.6, 2.5 Hz, 1H), 6.57-6.63 (m, 1H), 4.50-4.67 (m, 1H), 3.80-3.94 (m, 1H), 3.58-3.68 (m, 1H), 2.69-2.88 (m, 4H), 1.97-2.17 (m, 4H) |
| A0013_58_02 | ¹H NMR (DMSO-d₆ + TFA) δ: 9.27 (s, 1H), 8.57 (t, J = 5.5 Hz, 1H), 8.16 (s, 1H), 7.16-7.31 (m, 4H), 7.02-7.08 (m, 1H), 6.57-6.65 (m, |

-continued

| Compound | ¹H-NMR 400 |
|---|---|
| | 1H), 6.48-6.53 (m, 1H), 5.03-5.24 (m, 1H), 4.29-4.35 (m, 1H), 4.25-4.52 (m, 1H), 4.06-4.19 (m, 1H), 3.81-3.94 (m, 1H), 3.23-3.50 (m, 2H), 3.01-3.17 (m, 2H) |
| A0013_58_03 | ¹H NMR (CDCl₃) δ: 8.96 (s, 1H), 8.00 (s, 1H), 7.10-7.27 (m, 4H), 7.03-7.10 (m, 1H), 6.93-7.02 (m, J = 7.6 Hz, 2H), 6.61-6.71 (m, 1H), 4.95 (t, J = 7.3 Hz, 1H), 4.13-4.34 (m, 3H), 4.04-4.11 (m, 1H), 3.07-3.31 (m, 4H), 2.20 (s, 6H) |
| A0013_58_01 | ¹H NMR (CDCl₃) δ: 9.03 (s, 1H), 8.11 (s, 1H), 7.45 (t, J = 5.3 Hz, 1H), 7.24-7.33 (m, 2H), 7.15-7.23 (m, 3H), 7.05-7.13 (m, 2H), 5.28 (t, J = 7.3 Hz, 1H), 4.41-4.54 (m, 2H), 4.26-4.34 (m, 1H), 4.20 (ddd, J = 14.4, 6.8, 5.5 Hz, 1H), 3.34-3.52 (m, 2H), 3.17-3.33 (m, 2H), 2.23 (s, 3H) |
| A0013_82_01 | ¹H NMR (DMSO-d₆) δ: 9.14 (s, 1H), 9.06 (s, 2H), 8.73 (t, J = 5.5 Hz, 1H), 8.38-8.43 (m, 2H), 7.95 (s, 1H), 7.70-7.74 (m, 1H), 4.48 (dd, J = 8.3, 6.8 Hz, 1H), 3.90 (ddd, J = 13.8, 8.3, 6.0 Hz, 1H), 3.61-3.70 (m, 1H), 2.68-2.75 (m, 2H), 2.47-2.55 (m, 2H), 2.00-2.13 (m, 4H) |
| A0017_09_03 | ¹H NMR (DMSO-d₆) δ: 9.15 (s, 1H), 8.45 (t, J = 5.0 Hz, 1H), 7.97 (s, 1H), 7.09-7.27 (m, 3H), 4.59-4.74 (m, 1H), 3.87-3.97 (m, 1H), 3.83 (s, 3H), 3.74 (dt, J = 13.3, 6.4 Hz, 1H), 3.67 (s, 3H), 2.72-2.91 (m, 2H), 2.00-2.16 (m, 6H) |
| A0017_05_03 | ¹H NMR (DMSO-d₆ + TFA) δ: 9.31 (s, 1H), 8.60 (t, J = 5.0 Hz, 1H), 7.92-7.97 (m, 1H), 7.23-7.35 (m, 5H), 7.07-7.15 (m, 1H), 6.94-6.99 (m, 2H), 5.17 (dd, J = 9.8, 2.8 Hz, 1H), 4.47 (s, 2H), 4.11-4.20 (m, 1H), 3.92 (ddd, J = 13.1, 11.1, 6.5 Hz, 1H), 3.53-3.82 (m, 2H), 2.86-3.31 (m, 2H), 1.99 (s, 6H), 1.81-2.27 (m, 4H), 1.61-1.81 (m, 1H) |
| A0017_05_02 | ¹H NMR (DMSO-d₆ + TFA) δ: 9.32 (s, 1H), 8.80 (t, J = 5.8 Hz, 1H), 8.20 (s, 1H), 7.20-7.40 (m, 7H), 7.16 (d, J = 7.1 Hz, 1H), 5.10-5.24 (m, 1H), 4.48 (s, 2H), 4.17 (dt, J = 13.1, 4.5 Hz, 1H), 3.92 (ddd, J = 13.0, 11.0, 6.3 Hz, 1H), 3.57-3.81 (m, 2H), 2.97-3.26 (m, 2H), 1.99-2.04 (m, 3H), 1.82-2.26 (m, 4H), 1.63-1.79 (m, 1H) |
| A0017_05_01 | ¹H NMR (DMSO-d₆) δ: 9.04 (s, 1H), 8.75 (t, J = 5.0 Hz, 1H), 7.81 (s, 1H), 7.40-7.52 (m, 1H), 7.18-7.38 (m, 7H), 4.46 (s, 2H), 4.22 (t, J = 7.1 Hz, 1H), 3.78 (dt, J = 13.5, 6.5 Hz, 1H), 3.58 (dt, J = 13.5, 6.6 Hz, 1H), 3.24-3.31 (m, 1H), 2.75-2.84 (m, 1H), 2.61-2.71 (m, 1H), 2.20-2.30 (m, 1H), 2.05-2.15 (m, 1H), 1.82-1.91 (m, 2H), 1.46-1.58 (m, 2H) |
| A0016_11_02 | ¹H NMR (DMSO-d₆ + TFA) δ: 9.32 (s, 1H), 8.62 (t, J = 5.3 Hz, 1H), 8.23 (s, 1H), 7.22-7.31 (m, 2H), 7.09-7.16 (m, 1H), 6.90-7.01 (m, 5H), 5.22 (dd, J = 10.8, 3.8 Hz, 1H), 4.51-4.73 (m, 1H), 4.09-4.25 (m, 1H), 3.94 (td, J = 12.2, 6.3 Hz, 1H), 3.04-3.86 (m, 4H), 2.00 (s, 6H), 1.89-2.35 (m, 4H) |
| A0016_10_01 | ¹H NMR (DMSO-d₆) δ: 9.06 (s, 1H), 8.77 (t, J = 5.5 Hz, 1H), 7.84 (s, 1H), 7.47 (td, J = 8.1, 6.5 Hz, 1H), 7.32-7.37 (m, 1H), 7.20-7.32 (m, 3H), 6.90 (m, 3H), 4.23-4.33 (m, 2H), 3.81 (dt, J = 13.5, 6.6 Hz, 1H), 3.60 (dt, J = 13.5, 6.6 Hz, 1H), 2.78-2.87 (m, 1H), 2.65-2.74 (m, 1H), 2.35-2.44 (m, 1H), 2.17-2.27 (m, 1H), 1.90-1.99 (m, 2H), 1.57-1.71 (m, 2H) |
| A0016_20_03 | ¹H NMR (DMSO-d₆) δ: 9.29 (s, 1H), 8.92-9.07 (m, 1H), 8.17 (s, 1H), 7.39-7.57 (m, 1H), 7.17-7.38 (m, 2H), 4.94-5.13 (m, 1H), 4.13-4.33 (m, 1H), 3.82-4.06 (m, 1H), 3.65-3.82 (m, 2H), 2.73-2.95 (m, 2H), 1.59-1.89 (m, 5H), 1.25-1.42 (m, 1H) |
| A0015_55_01 | ¹H NMR (DMSO-d₆) δ: 8.96 (s, 1H), 8.75 (t, J = 5.5 Hz, 1H), 7.38-7.53 (m, 1H), 7.20-7.36 (m, 2H), 6.96-7.15 (m, 4H), 4.32 (t, J = 6.9 Hz, 1H), 3.88-3.97 (m, 1H), 3.82, 3.61 (AB$_q$, J$_{AB}$ = 14.6 Hz, 2H,), 3.44-3.56 (m, 1H), 2.72-2.86 (m, 3H), 2.57-2.69 (m, 1H), 2.42 (s, 3H) |
| A0015_73_01 | ¹H NMR (DMSO-d₆) δ: 8.98 (s, 1H), 8.32 (t, J = 5.5 Hz, 1H), 7.02-7.15 (m, 6H), 6.94-7.01 (m, 1H), 4.44 (t, J = 7.1 Hz, 1H), 3.73-3.84 (m, 2H), 3.55-3.68 (m, 2H), 2.75-2.87 (m, 3H), 2.57-2.66 (m, 1H), 2.44 (s, 3H), 2.06 (s, 6H) |
| A0015_58_02 | ¹H NMR (DMSO-d₆ + TFA) δ: 9.16-9.29 (m, 1H), 8.86-8.98 (m, 1H), 7.46 (td, J = 8.2, 6.3 Hz, 1H), 7.30-7.35 (m, 1H), 7.26 (t, J = 8.6 Hz, 1H), 4.82-5.03 (m, 1H), 4.06-4.22 (m, 1H), 3.58-3.74 (m, 1H), 3.00-3.48 (m, 4H), 2.45 (s, 3H), 2.14-2.32 (m, 4H) |
| A0015_72_01 | ¹H NMR (DMSO-d₆) δ: 9.02 (s, 1H), 8.37 (t, J = 5.4 Hz, 1H), 7.14 (t, J = 7.6 Hz, 1H), 6.95-7.05 (m, 2H), 4.41-4.61 (m, 1H), 3.64-3.85 (m, 1H), 3.56 (dt, J = 13.6, 6.5 Hz, 1H), 2.57-2.80 (m, 4H), 2.41 (s, 3H), 2.10 (s, 6H), 1.89-2.07 (m, 4H) |
| A0016_21_02 | ¹H NMR (DMSO-d₆) δ: 9.01 (s, 1H), 8.95 (dd, J = 4.0, 1.5 Hz, 1H), 8.64 (t, J = 5.5 Hz, 1H), 8.49 (dd, J = 8.5, 1.3 Hz, 1H), 8.08-8.14 (m, 1H), 7.75-7.85 (m, 1H), 7.61 (dd, J = 7.0, 1.0 Hz, 1H), 7.54 (dd, J = 8.6, 4.0 Hz, 1H), 4.46 (t, J = 7.3 Hz, 1H), 3.84 (ddd, J = 13.5, 7.4, 5.8 Hz, 1H), 3.54 (dt, J = 13.3, 6.4 Hz, 1H), 2.57-2.70 (m, 4H), 2.40 (s, 3H), 1.90-2.06 (m, 4H) |

| Compound | ¹H-NMR 400 |
|---|---|
| A0016_23_02 | ¹H NMR (DMSO-d₆ + TFA) δ: 9.25 (s, 1H), 9.01 (s, 2H), 8.82 (t, J = 5.3 Hz, 1H), 8.34 (dd, J = 8.6, 2.0 Hz, 1H), 8.19-8.23 (m, 1H), 7.61-7.66 (m, 1H), 5.01-5.09 (m, 1H), 4.10-4.20 (m, 1H), 3.66-3.76 (m, 1H), 3.33-3.47 (m, 2H), 3.16-3.29 (m, 2H), 2.49 (s, 3H), 2.21-2.38 (m, 4H) |
| A0015_57_02 | ¹H NMR (DMSO-d₆) δ: 8.96 (s, 1H), 8.69 (t, J = 5.3 Hz, 1H), 7.39-7.50 (m, 1H), 7.30-7.36 (m, 1H), 7.26 (t, J = 8.6 Hz, 1H), 4.09 (t, J = 6.5 Hz, 1H), 3.83 (dt, J = 12.3, 5.8 Hz, 1H), 3.51-3.63 (m, 4H), 3.33-3.44 (m, 1H), 2.45-2.52 (m, 2H), 2.31-2.44 (m, 5H) |
| A0015_71_02 | ¹H NMR (DMSO-d₆ + TFA) δ: 9.24 (s, 1H), 8.56 (dd, J = 6.3, 4.3 Hz, 1H), 7.13 (t, J = 7.6 Hz, 1H), 6.98 (d, J = 7.6 Hz, 2H), 5.06 (dd, J = 10.3, 4.3 Hz, 1H), 4.16 (dt, J = 13.3, 4.2 Hz, 1H), 3.66-3.95 (m, 7H), 3.02-3.27 (m, 2H), 2.47 (s, 3H), 1.96 (s, 6H) |
| A0017_13_01 | ¹H NMR (DMSO-d₆) δ: 9.09-9.19 (m, 1H), 9.03 (s, 2H), 8.64-8.77 (m, 1H), 8.34 (dd, J = 8.6, 2.0 Hz, 1H), 8.23 (s, 1H), 7.62-7.67 (m, 1H), 4.55-4.88 (m, 1H), 3.95-4.15 (m, 5H), 3.71-3.88 (m, 5H), 2.63-3.23 (m, 4H), 2.46 (s, 3H) |
| A0012_60_01 | ¹H NMR (DMSO-d₆) δ: 8.81 (t, J = 5.5 Hz, 1H), 7.59 (s, 1H), 7.47 (td, J = 8.2, 6.2 Hz, 1H), 7.33-7.38 (m, 1H), 7.25-7.33 (m, 1H), 4.25-4.36 (m, 1H), 3.76-3.87 (m, 1H), 3.57 (dt, J = 13.4, 6.5 Hz, 1H), 2.65-2.75 (m, 2H), 2.64 (s, 3H), 2.53-2.61 (m, 2H), 1.91-2.06 (m, 4H) |
| A0012_62_01 | ¹H NMR (DMSO-d₆) δ: 8.85 (t, J = 5.5 Hz, 1H), 7.92 (d, J = 2.3 Hz, 1H), 7.21-7.33 (m, 2H), 7.12-7.21 (m, 1H), 4.98-5.13 (m, 1H), 4.11-4.22 (m, 1H), 3.73-3.90 (m, 1H), 3.11-3.65 (m, 4H), 2.70 (s, 3H), 2.18-2.41 (m, 4H), 2.07 (s, 3H) |
| A0012_62_02 | ¹H NMR (DMSO-d₆) δ: 8.39 (t, J = 5.8 Hz, 1H), 7.55 (s, 1H), 7.15 (t, J = 7.5 Hz, 1H), 6.94-7.07 (m, J = 7.6 Hz, 2H), 4.28 (t, J = 7.6 Hz, 1H), 3.69 (ddd, J = 13.6, 8.4, 5.5 Hz, 1H), 3.58 (dt, J = 13.6, 6.6 Hz, 1H), 2.55-2.71 (m, 5H), 2.34-2.47 (m, 2H), 2.18 (s, 6H), 1.84-2.04 (m, 4H) |
| A0012_66_01 | ¹H NMR (DMSO-d₆) δ: 8.69-8.84 (m, 1H), 7.77-7.91 (m, 1H), 7.08-7.32 (m, 7H), 4.87-5.17 (m, 1H), 4.02-4.42 (m, 3H), 3.75-3.93 (m, 2H), 3.00-3.12 (m, 3H), 2.68 (s, 3H), 2.07 (s, 3H) |
| A0012_65_01 | ¹H NMR (DMSO-d₆) δ: 8.51-8.63 (m, 1H), 7.82-7.92 (m, 1H), 7.19-7.33 (m, 4H), 7.09-7.19 (m, 1H), 6.99 (m, 2H), 4.97-5.15 (m, 1H), 4.07-4.44 (m, 3H), 3.81-3.99 (m, 2H), 2.99-3.14 (m, 3H), 2.69 (s, 3H), 2.04 (s, 6H) |
| A0012_64_01 | ¹H NMR (DMSO-d₆ + TFA) δ: 9.06 (t, J = 5.3 Hz, 1H), 7.91 (s, 1H), 7.43-7.53 (m, 1H), 7.19-7.37 (m, 6H), 5.15 (dd, J = 10.3, 4.3 Hz, 1H), 4.37-4.46 (m, 1H), 4.36-4.80 (m, 1H), 4.30 (dt, J = 13.0, 4.3 Hz, 1H), 3.91 (ddd, J = 13.2, 10.7, 6.8 Hz, 1H), 3.37-3.64 (m, 1H), 3.08-3.19 (m, 2H), 2.70 (s, 3H) |
| A0015_62_03 | ¹H NMR (DMSO-d₆ + TFA) δ: 8.99 (t, J = 5.8 Hz, 1H), 8.59 (s, 1H), 7.42-7.53 (m, 2H), 7.31-7.36 (m, 1H), 7.23-7.31 (m, 1H), 4.90 (dd, J = 10.6, 4.5 Hz, 1H), 4.14 (dt, J = 13.3, 4.9 Hz, 1H), 3.76-3.93 (m, 5H), 3.24-3.45 (m, 2H), 3.07-3.21 (m, 2H) |
| A0015_68_02 | ¹H NMR (DMSO-d₆) δ: 8.77 (t, J = 5.5 Hz, 1H), 8.36 (s, 1H), 7.47 (td, J = 8.2, 6.3 Hz, 1H), 7.33-7.38 (m, 1H), 7.24-7.33 (m, 1H), 7.18 (s, 1H), 4.12-4.22 (m, 1H), 3.72-3.84 (m, 1H), 3.59-3.69 (m, 1H), 2.65-2.79 (m, 2H), 2.39-2.54 (m, 2H), 1.90-2.07 (m, 4H) |
| A0016_24_02 | ¹H NMR (DMSO-d₆ + TFA) δ: 8.58 (t, J = 5.5 Hz, 1H), 8.55 (s, 1H), 7.46 (s, 1H), 7.14 (t, J = 7.6 Hz, 1H), 6.98-7.02 (m, 2H), 4.86-4.98 (m, 1H), 4.00-4.12 (m, 1H), 3.79-3.91 (m, 1H), 3.16-3.39 (m, 4H), 2.15-2.38 (m, 4H), 2.07 (s, 6H) |
| A0016_26_02 | ¹H NMR (DMSO-d₆ + TFA) δ: 9.00 (s, 2H), 8.77-8.85 (m, 1H), 8.53 (s, 1H), 8.36 (dd, J = 8.3, 2.3 Hz, 1H), 8.29 (s, 1H), 7.65 (dd, J = 8.6, 1.5 Hz, 1H), 7.38-7.48 (m, 1H), 4.72-4.80 (m, 1H), 3.98-4.12 (m, 1H), 3.75-3.88 (m, 1H), 3.04-3.26 (m, 4H), 2.16-2.33 (m, 4H) |
| A0015_69_02 | ¹H NMR (DMSO-d₆) δ: 9.04 (t, J = 5.3 Hz, 1H), 8.58 (s, 1H), 7.55 (s, 1H), 7.42-7.52 (m, 2H), 7.10-7.39 (m, 5H), 5.07 (dd, J = 10.6, 4.0 Hz, 1H), 4.40-4.59 (m, 2H), 4.14-4.28 (m, 1H), 4.00-4.11 (m, 1H), 3.59-3.77 (m, 1H), 3.41-3.57 (m, 1H), 3.04-3.22 (m, 2H) |
| A0016_25_02 | ¹H NMR (DMSO-d₆) δ: 8.45-8.65 (m, 2H), 7.42-7.52 (m, 1H), 7.10-7.27 (m, 5H), 6.94-7.06 (m, 2H), 4.69-5.06 (m, 1H), 4.18-4.41 (m, 2H), 3.86-4.13 (m, 3H), 2.88-3.17 (m, 3H), 2.10 (s, 6H) |
| A0017_37_01 | ¹H NMR (DMSO-d₆ + TFA) δ: 8.48 (s, 1H), 8.44 (s, 1H), 7.14-7.19 (m, 1H), 7.09-7.14 (m, 1H), 7.02-7.07 (m, 1H), 5.00 (dd, J = 9.1, 5.5 Hz, 1H), 4.10 (dt, J = 12.7, 5.5 Hz, 1H), 3.86 (dd, J = 8.1, 6.5 Hz, 1H), 3.82 (s, 3H), 3.65 (s, 3H), 3.24-3.53 (m, 4H), 2.22-2.40 (m, 4H), 2.17 (s, 3H) |
| A0017_37_04 | ¹H NMR (DMSO-d₆ + TFA) δ: 9.01 (s, 2H), 8.82 (t, J = 5.5 Hz, 1H), 8.47 (s, 1H), 8.35 (dd, J = 8.6, 2.0 Hz, 1H), 8.23 (d, J = 2.0 Hz, 1H), 7.65 (d, J = 8.6 Hz, 1H), 4.95 (dd, J = 9.6, 4.5 Hz, 1H), 4.09-4.21 (m, 1H), 3.78-3.93 (m, 1H), 3.23-3.53 (m, 4H), 2.27-2.43 (m, 4H), 2.24 (s, 3H) |

| Compound | ¹H-NMR 400 |
|---|---|
| A0017_33_01 | ¹H NMR (DMSO-d₆ + TFA) δ: 8.89 (t, J = 5.8 Hz, 1H), 8.42 (s, 1H), 7.42-7.54 (m, 1H), 7.32-7.37 (m, 1H), 7.28 (t, J = 8.6 Hz, 1H), 4.55-4.61 (m, 1H), 4.05-4.15 (m, 1H), 3.82 (ddd, J = 13.0, 10.4, 5.8 Hz, 1H), 3.12-3.32 (m, 4H), 2.26 (ddd, J = 18.6, 13.3, 5.3 Hz, 4H), 2.17 (s, 3H) |
| A0017_37_02 | ¹H NMR (DMSO-d₆ + TFA) δ: 8.50 (s, 1H), 8.43 (t, J = 5.8 Hz, 1H), 7.07-7.22 (m, 2H), 6.98-7.07 (m, 1H), 5.07 (m, 1H), 4.07-4.17 (m, 1H), 3.72-3.94 (m, 8H), 3.64 (s, 3H), 3.08-3.23 (m, 4H), 2.18 (s, 3H) |
| A0017_37_05 | ¹H NMR (DMSO-d₆ + TFA) δ: 9.02 (s, 2H), 8.83 (t, J = 5.3 Hz, 1H), 8.49 (s, 1H), 8.35 (dd, J = 8.3, 1.8 Hz, 1H), 8.22 (s, 1H), 7.65 (d, J = 8.6 Hz, 1H), 4.93 (dd, J = 10.1, 4.5 Hz, 1H), 4.13-4.24 (m, 1H), 3.80-3.95 (m, 5H), 3.14-3.27 (m, 4H), 2.24 (s, 3H) |
| A0017_33_02 | ¹H NMR (DMSO-d₆ + TFA) δ: 8.94 (t, J = 4.8 Hz, 1H), 8.48 (s, 1H), 7.42-7.54 (m, 1H), 7.32-7.37 (m, 1H), 7.27 (t, J = 8.6 Hz, 1H), 4.88 (dd, J = 10.1, 3.0 Hz, 1H), 4.14-4.24 (m, 1H), 3.74-3.94 (m, 5H), 3.12-3.25 (m, 4H), 2.19 (s, 3H) |
| A0017_37_03 | ¹H NMR (DMSO-d₆) δ: 8.41-8.53 (m, 2H), 7.95 (d, J = 8.1 Hz, 1H), 7.45-7.56 (m, 1H), 7.02-7.31 (m, 5H), 4.98-5.11 (m, 1H), 4.06-4.58 ((m, 3H), 3.87-4.03 (m, 2H), 3.82 (s, 3H), 3.64 (s, 3H), 2.91-3.18 (m, 3H), 2.11-2.26 (m, 3H) |
| A0017_37_06 | ¹H NMR (DMSO-d₆) δ: 9.02 (s, 2H), 8.74-8.88 (m, 1H), 8.41-8.50 (m, 1H), 8.32-8.39 (m, 1H), 8.24 (d, J = 2.0 Hz, 1H), 7.92-7.99 (m, 1H), 7.63-7.69 (m, 1H), 7.48-7.54 (m, 1H), 7.14-7.31 (m, 2H), 4.92-5.11 (m, 1H), 4.06-4.52 (m, 3H), 3.87-4.04 (m, 2H), 2.99-3.18 (m, 3H), 2.23 (s, 3H) |
| A0017_55_01 | ¹H NMR (DMSO-d₆ + TFA) δ: 9.02 (s, 2H), 8.79 (t, J = 6.0 Hz, 1H), 8.36 (dd, J = 8.6, 2.3 Hz, 1H), 8.24 (d, J = 2.3 Hz, 1H), 7.66 (d, J = 8.6 Hz, 1H), 4.81-4.91 (m, 1H), 4.09-4.19 (m, 1H), 3.73-3.84 (m, 1H), 3.24-3.54 (m, 2H), 2.39 (s, 3H), 2.25-2.38 (m, 6H), 2.17 (s, 3H) |
| A0017_60_02 | ¹H NMR (DMSO-d₆ + TFA) δ: 9.25 (s, 1H), 8.95 (t, J = 5.2 Hz, 1H), 7.44 (td, J = 8.3, 6.3 Hz, 1H), 7.19-7.37 (m, 7H), 4.94-5.09 (m, 1H), 4.49 (s, 2H), 4.18-4.27 (m, 1H), 3.46-3.91 (m, 3H), 2.93-3.39 (m, 3H), 2.45 (s, 3H), 1.83-2.30 (m, 3H), 1.54-1.80 (m, 1H) |
| A0017_60_01 | ¹H NMR (DMSO-d₆ + TFA) δ: 9.25 (s, 1H), 8.91-9.01 (m, 1H), 7.41-7.49 (m, 1H), 7.18-7.36 (m, 4H), 6.91-7.01 (m, 3H), 4.99-5.11 (m, 1H), 4.48-4.77 (m, 1H), 4.19-4.30 (m, 1H), 3.62-4.05 (m, 2H), 3.00-3.54 (m, 3H), 2.46 (s, 3H), 1.71-2.34 (m, 4H) |
| A0017_50_01 | ¹H NMR (DMSO-d₆ + TFA) δ: 8.99 (s, 2H), 8.88 (t, J = 5.7 Hz, 1H), 8.34 (dd, J = 8.4, 2.0 Hz, 1H), 8.23 (d, J = 2.0 Hz, 1H), 7.90 (s, 1H), 7.63 (d, J = 8.6 Hz, 1H), 5.07 (dd, J = 8.7, 5.2 Hz, 1H), 4.13 (dt, J = 13.3, 5.3 Hz, 1H), 3.75-3.87 (m, 1H), 3.28-3.43 (m, 2H), 3.16-3.28 (m, 2H), 2.71 (s, 3H), 2.22-2.38 (m, 4H) |
| A0018_17_01 | ¹H NMR (DMSO-d₆ + TFA) δ: 9.01 (t, J = 5.8 Hz, 1H), 7.89 (s, 1H), 7.42-7.53 (m, 1H), 7.20-7.40 (m, 7H), 4.94-5.06 (m, 1H), 4.49 (s, 2H), 4.13-4.23 (m, 1H), 3.75-3.90 (m, 1H), 3.48-3.78 (m, 2H), 2.89 (d, J = 19.6 Hz, 4H), 2.69 (s, 3H), 1.79-2.29 (m, 2H), 1.57-1.80 (m, 1H) |
| A0017_75_02 | ¹H NMR (DMSO-d₆ + TFA) δ: 9.22 (s, 1H), 9.01 (s, 2H), 8.66 (t, J = 5.5 Hz, 1H), 8.34 (dd, J = 8.6, 1.8 Hz, 1H), 8.22-8.26 (m, 1H), 7.63 (d, J = 8.3 Hz, 1H), 4.59 (t, J = 7.3 Hz, 1H), 3.90-4.01 (m, 1H), 3.53-3.62 (m, 1H), 3.05-3.19 (m, 1H), 2.89-3.02 (m, 1H), 2.71-2.84 (m, 2H), 2.45 (s, 3H), 1.86-2.01 (m, 2H), 1.70-1.81 (m, 2H) |
| A0017_75_01 | ¹H NMR (DMSO-d₆) δ: 9.04 (s, 2H), 8.98 (s, 1H), 8.67 (t, J = 5.9 Hz, 1H), 8.32-8.37 (m, 1H), 8.29-8.31 (m, 1H), 7.65 (dd, J = 8.6, 1.0 Hz, 1H), 4.12-4.17 (m, 1H), 3.56-3.77 (m, 5H), 3.18-3.27 (m, 1H), 2.45 (s, 3H) |
| A0017_74_02 | ¹H NMR (DMSO-d₆ + TFA) δ: 9.19 (s, 1H), 8.80 (t, J = 5.7 Hz, 1H), 7.45 (td, J = 8.3, 6.3 Hz, 1H), 7.30-7.35 (m, 1H), 7.26 (td, J = 8.7, 0.9 Hz, 1H), 4.46-4.53 (m, 1H), 3.89-3.98 (m, 1H), 3.58 (ddd, J = 13.9, 8.2, 6.0 Hz, 1H), 3.03-3.18 (m, 1H), 2.86-3.00 (m, 1H), 2.69-2.83 (m, 2H), 2.41 (s, 3H), 1.86-1.98 (m, 2H), 1.69-1.79 (m, 2H) |
| A0017_68_01 | ¹H NMR (CDCl₃) δ: 8.26-8.35 (m, 1H), 8.10 (s, 1H), 7.45-7.51 (m, 1H), 7.28-7.38 (m, 5H), 7.17-7.24 (m, 2H), 7.04 (t, J = 8.6 Hz, 1H), 4.84-4.93 (m, 1H), 4.37-4.49 (m, 3H), 4.08-4.18 (m, 1H), 3.78-3.84 (m, 1H), 3.35-3.45 (m, 2H), 2.97-3.25 (m, 2H), 2.30-2.53 (m, 2H), 2.08 (t, J = 15.1 Hz, 2H) |
| A0018_69_01 | ¹H NMR (DMSO-d₆) δ: 9.03 (s, 1H), 8.58 (t, J = 4.7 Hz, 1H), 8.07-8.12 (m, 1H), 7.99-8.02 (m, 1H), 7.74-7.84 (m, 2H), 7.55-7.59 (m, 1H), 7.25-7.30 (m, 1H), 4.44-4.54 (m, 1H), 3.79-3.91 (m, 1H), 3.45-3.50 (m, 1H), 2.64-2.78 (m, 4H), 2.56 (s, 3H), 2.43 (s, 3H), 1.95-2.11 (m, 4H) |
| A0018_60_01 | ¹H NMR (DMSO-d₆) δ: 9.26 (s, 1H), 9.00 (s, 2H), 8.70 (t, J = 5.9 Hz, 1H), 8.31-8.37 (m, 2H), 7.62-7.67 (m, 1H), 4.63 (t, J = 6.9 Hz, 1H), 3.88 (dt, J = 13.7, 6.7 Hz, 1H), 3.45-3.54 (m, 1H), 2.57-2.65 (m, 4H), 1.92-2.09 (m, 4H) |

| Compound | ¹H-NMR 400 |
|---|---|
| A0018_59_01 | ¹H NMR (DMSO-d₆) δ: 9.31 (s, 1H), 8.89 (t, J = 5.8 Hz, 1H), 7.48-7.56 (m, 1H), 7.40 (s, 1H), 7.30-7.37 (m, 1H), 4.63 (t, J = 6.8 Hz, 1H), 3.88 (dt, J = 13.5, 6.6 Hz, 1H), 3.56-3.67 (m, 1H), 2.59-2.70 (m, 4H), 1.95-2.10 (m, 4H) |
| A0017_81_02 | ¹H NMR (DMSO-d₆ + TFA) δ: 9.28 (s, 1H), 8.97-9.01 (m, 2H), 8.73 (t, J = 5.7 Hz, 1H), 8.48-8.53 (m, 1H), 8.42-8.48 (m, 1H), 7.39-7.47 (m, 1H), 5.15-5.21 (m, 1H), 4.11-4.20 (m, 1H), 3.71-3.81 (m, 1H), 3.44-3.64 (m, 2H), 3.25-3.38 (m, 2H), 2.48 (s, 3H), 2.24-2.38 (m, 4H) |
| A0017_81_03 | ¹H NMR (DMSO-d₆ + TFA) δ: 9.28 (s, 1H), 8.94 (s, 2H), 8.68-8.73 (m, 1H), 8.39-8.48 (m, 2H), 7.28 (d, J = 8.8 Hz, 1H), 5.18 (t, J = 5.7 Hz, 1H), 4.15 (dt, J = 13.8, 5.7 Hz, 1H), 3.87 (s, 3H), 3.73-3.84 (m, 1H), 3.39-3.69 (m, 2H), 3.22-3.38 (m, 2H), 2.47 (s, 3H), 2.22-2.41 (m, 4H) |
| A0017_85_01 | ¹H NMR (DMSO-d₆ + TFA) δ: 9.19-9.32 (m, 2H), 8.82 (t, J = 5.3 Hz, 1H), 8.72-8.76 (m, 1H), 8.65-8.69 (m, 1H), 8.20 (dd, J = 8.4, 2.1 Hz, 1H), 7.97-8.00 (m, 1H), 7.63 (d, J = 8.3 Hz, 1H), 5.10 (dd, J = 8.8, 4.9 Hz, 1H), 4.17 (dt, J = 13.5, 5.3 Hz, 1H), 3.73 (ddd, J = 13.5, 8.8, 6.4 Hz, 1H), 3.38-3.56 (m, 2H), 3.22-3.33 (m, 2H), 2.50 (s, 3H), 2.23-2.38 (m, 4H) |
| A0017_83_01 | ¹H NMR (DMSO-d₆ + TFA) δ: 9.28 (s, 1H), 9.00 (s, 2H), 8.85 (t, J = 5.4 Hz, 1H), 8.34 (dd, J = 8.4, 2.1 Hz, 1H), 8.17-8.22 (m, 1H), 7.62 (d, J = 8.6 Hz, 1H), 7.24-7.33 (m, 2H), 6.91-7.00 (m, 3H), 5.09-5.22 (m, 1H), 4.49-4.82 (m, 1H), 4.22 (dt, J = 12.8, 4.4 Hz, 1H), 3.65-4.03 (m, 2H), 3.10-3.54 (m, 3H), 2.50 (s, 3H), 1.71-2.36 (m, 4H) |
| A0018_69_01 | ¹H NMR (DMSO-d₆) δ: 8.96 (s, 1H), 8.51 (t, J = 4.7 Hz, 1H), 8.00-8.05 (m, 1H), 7.92-7.95 (m, 1H), 7.68-7.77 (m, 2H), 7.51 (d, J = 8.3 Hz, 1H), 7.21 (d, J = 7.3 Hz, 1H), 4.36-4.51 (m, 1H), 3.73-3.84 (m, 1H), 3.37-3.43 (m, 1H), 2.54-2.75 (m, 4H), 2.49 (s, 3H), 2.37 (s, 3H), 1.86-2.07 (m, 4H) |
| A0018_81_01 | ¹H NMR (DMSO-d₆ + TFA) δ: 9.19 (s, 1H), 9.01 (s, 2H), 8.34 (ddd, J = 8.4, 2.1, 1.0 Hz, 1H), 8.01-8.26 (m, 1H), 7.59-7.71 (m, 1H), 4.99-5.17 (m, 1H), 4.13-4.40 (m, 1H), 3.78-4.08 (m, 1H), 2.90-3.32 (m, 4H), 2.75 (s, 3H), 2.47 (s, 3H), 2.12-2.32 (m, 4H) |
| A0018_89_01 | ¹H NMR (DMSO-d₆ + TFA) δ: 9.27 (s, 1H), 8.86 (t, J = 5.3 Hz, 1H), 8.74 (dd, J = 2.5, 1.5 Hz, 1H), 8.67 (d, J = 2.5 Hz, 1H), 8.21 (dd, J = 8.3, 2.3 Hz, 1H), 8.03-8.06 (m, 1H), 7.89 (s, 1H), 7.62-7.68 (m, 1H), 4.95-5.06 (m, 1H), 4.06-4.16 (m, 1H), 3.72-3.83 (m, 1H), 3.11-3.41 (m, 4H), 2.71 (s, 3H), 2.18-2.36 (m, 4H) |
| A0018_89_02 | ¹H NMR (DMSO-d₆) δ: 8.61 (t, J = 5.7 Hz, 1H), 8.06-8.15 (m, 2H), 7.74-7.83 (m, 2H), 7.53-7.64 (m, 2H), 7.27 (dd, J = 5.7, 2.9 Hz, 1H), 4.30 (t, J = 7.4 Hz, 1H), 3.75-3.85 (m, 1H), 3.48-3.58 (m, 1H), 2.60-2.73 (m, 5H), 2.55 (s, 3H), 2.44-2.49 (m, 2H), 1.89-2.07 (m, 4H) |
| A0018_88_01 | ¹H NMR (DMSO-d₆) δ: 9.00 (s, 2H), 8.59 (dd, J = 7.1, 2.3 Hz, 1H), 8.42-8.51 (m, 2H), 7.57 (s, 1H), 7.47 (dd, J = 10.2, 8.7 Hz, 1H), 4.33 (dd, J = 8.3, 6.5 Hz, 1H), 3.80 (ddd, J = 13.7, 8.3, 5.5 Hz, 1H), 3.55-3.64 (m, 1H), 2.63-2.71 (m, 2H), 2.64 (s, 3H), 2.42-2.51 (m, 2H), 1.91-2.04 (m, 4H) |
| A0018_95_01 | ¹H NMR (DMSO-d₆) δ: 8.90 (t, J = 5.9 Hz, 1H), 8.11 (s, 1H), 7.44-7.52 (m, 1H), 7.34-7.38 (m, 1H), 7.30 (t, J = 8.6 Hz, 1H), 4.42 (t, J = 7.2 Hz, 1H), 3.80-3.89 (m, 1H), 3.68-3.77 (m, 1H), 2.64-2.72 (m, 2H), 2.53-2.62 (m, 2H), 1.91-2.04 (m, 4H) |
| A0018_94_01 | ¹H NMR (DMSO-d₆) δ: 9.01 (s, 2H), 8.78 (t, J = 5.4 Hz, 1H), 8.31-8.39 (m, 2H), 8.14 (s, 1H), 7.67 (d, J = 8.3 Hz, 1H), 4.52 (t, J = 7.3 Hz, 1H), 3.82-3.94 (m, 1H), 3.67-3.77 (m, 1H), 2.65-2.78 (m, 2H), 2.55-2.65 (m, 2H), 1.96-2.12 (m, 4H) |
| A0020_21_02 | ¹H NMR (DMSO-d₆) δ: 9.00 (s, 2H), 8.60 (dd, J = 7.1, 2.5 Hz, 1H), 8.41-8.53 (m, 2H), 7.60 (s, 1H), 7.47 (dd, J = 10.1, 8.8 Hz, 1H), 4.34 (dd, J = 8.4, 6.4 Hz, 1H), 3.80 (ddd, J = 13.7, 8.6, 5.7 Hz, 1H), 3.55-3.67 (m, 1H), 2.97 (q, J = 7.6 Hz, 2H), 2.61-2.73 (m, 2H), 2.41-2.50 (m, 2H), 1.90-2.05 (m, 4H), 1.30 (t, J = 7.6 Hz, 3H) |
| A0020_21_01 | ¹H NMR (DMSO-d₆) δ: 9.00 (s, 2H), 8.66 (t, J = 5.8 Hz, 1H), 8.30-8.44 (m, 2H), 7.62-7.71 (m, 1H), 7.60 (s, 1H), 4.26-4.38 (m, 1H), 3.80 (ddd, J = 13.8, 8.3, 6.0 Hz, 1H), 3.56 (dt, J = 13.5, 6.2 Hz, 1H), 2.98 (q, J = 7.6 Hz, 2H), 2.61-2.73 (m, 2H), 2.42-2.50 (m, 2H), 1.93-2.07 (m, 1H), 1.30 (t, J = 7.6 Hz, 3H) |
| A0020_20_01 | ¹H NMR (DMSO-d₆) δ: 8.79 (t, J = 5.8 Hz, 1H), 7.57 (s, 1H), 7.47 (td, J = 8.2, 6.2 Hz, 1H), 7.34-7.37 (m, 1H), 7.27-7.32 (m, 1H), 4.20-4.25 (m, 1H), 3.77 (ddd, J = 13.7, 8.0, 5.8 Hz, 1H), 3.52-3.60 (m, 1H), 2.96 (q, J = 7.6 Hz, 2H), 2.59-2.67 (m, 2H), 2.40-2.48 (m, 2H), 1.89-2.02 (m, 4H), 1.29 (t, J = 7.6 Hz, 3H) |
| A0020_28_01 | ¹H NMR (DMSO-d₆ + TFA) δ: 8.98 (s, 2H), 8.77 (t, J = 5.2 Hz, 1H), 8.51-8.58 (m, 1H), 8.41-8.51 (m, 1H), 7.83-7.89 (m, 1H), 7.44 (t, |

-continued

| Compound | ¹H-NMR 400 |
|---|---|
| | J = 9.3 Hz, 1H), 5.09-5.21 (m, 1H), 4.08-4.18 (m, 1H), 3.77-3.89 (m, 1H), 3.23-3.53 (m, 4H), 2.40-2.50 (m, 1H), 2.23-2.40 (m, 4H), 1.11-1.20 (m, 2H), 0.96-1.06 (m, 2H) |
| A0021_17_01 | ¹H NMR (DMSO-$d_6$ + TFA) δ: 8.99 (s, 2H), 8.90 (t, J = 5.4 Hz, 1H), 8.35 (dd, J = 8.4, 2.1 Hz, 1H), 8.23-8.27 (m, 1H), 7.82-7.88 (m, 1H), 7.59-7.66 (m, 1H), 5.03-5.17 (m, 1H), 4.07-4.21 (m, 1H), 3.75-3.89 (m, 1H), 3.19-3.60 (m, 4H), 2.43-2.49 (m, 1H), 2.19-2.41 (m, 4H), 1.12-1.20 (m, 2H), 0.96-1.05 (m, 2H) |
| A0020_27_01 | ¹H NMR (DMSO-$d_6$ + TFA) δ: 9.02 (t, J = 5.8 Hz, 1H), 7.78-7.87 (m, 1H), 7.39-7.50 (m, 1H), 7.18-7.36 (m, 2H), 4.95-5.08 (m, 1H), 4.10-4.23 (m, 1H), 3.70-3.84 (m, 1H), 3.35-3.57 (m, 2H), 3.17-3.33 (m, 2H), 2.41-2.49 (m, 1H), 2.23-2.36 (m, 4H), 1.12-1.20 (m, 2H), 0.97-1.03 (m, 2H) |
| A0021_24_01 | ¹H NMR (DMSO-$d_6$ + TFA) δ: 9.28 (s, 1H), 9.03 (t, J = 5.4 Hz, 1H), 7.44 (td, J = 8.3, 6.3 Hz, 1H), 7.30 (d, J = 8.3 Hz, 1H), 7.24 (t, J = 8.7 Hz, 1H), 5.12-5.37 (m, 1H), 3.99-4.28 (m, 2H), 3.14-3.92 (m, 3H), 2.19-2.48 (m, 7H), 1.57-1.73 (m, 3H) |
| A0021_07_11 | Two diastereoisomers (52/48): ¹H NMR (DMSO-$d_6$ + TFA) δ: 9.28 (s, 1H), 8.96 (t, J = 5.3 Hz, 1H), 7.66-7.88 (m, 3H), 7.52-7.66 (m, 1H), 7.38-7.48 (m, 1H), 7.16-7.33 (m, 2H), 4.87-5.11 (m, 2H), 4.09-4.38 (m, 2H), 3.76-4.02 (m, 2H), 3.69 (br. s., 1H), 3.20-3.43 (m, 1H), 2.97-3.14 (m, 2H), 2.38-2.48 (m, 3H) |
| A0021_07_22 | Diastereoisomer 1 (60%): ¹H NMR (DMSO-$d_6$) δ: 8.96 (d, J = 11.1 Hz, 1H), 8.71-8.80 (m, 1H), 7.40-7.50 (m, 2H), 7.33 (d, J = 8.1 Hz, 1H), 7.24-7.30 (m, 1H), 7.14-7.23 (m, 1H), 7.06 (tt, J = 8.5, 2.9 Hz, 1H), 4.67 (dd, J = 9.8, 1.8 Hz, 1H), 4.13-4.23 (m, 1H), 3.90-3.99 (m, 1H), 3.80-3.90 (m, 1H), 3.73 (td, J = 11.3, 2.4 Hz, 1H), 3.35-3.44 (m, 1H), 2.99 (d, J = 11.3 Hz, 1H), 2.77 (d, J = 10.8 Hz, 1H), 2.31-2.39 (m, 4H), 2.04 (t, J = 10.6 Hz, 1H). Diastereoisomer 2 (40%): ¹H NMR (DMSO-$d_6$) δ: 8.96 (d, J = 11.1 Hz, 1H), 8.71-8.81 (m, 1H), 7.39-7.51 (m, 2H), 7.33 (d, J = 8.1 Hz, 1H), 7.24-7.30 (m, 1H), 7.16-7.24 (m, 1H), 7.06 (tt, J = 8.5, 2.9 Hz, 1H), 4.74 (dd, J = 9.9, 1.9 Hz, 1H), 4.18 (dt, J = 14.0, 7.0 Hz, 1H), 3.91-3.99 (m, 1H), 3.80-3.91 (m, 1H), 3.66 (td, J = 11.2, 2.0 Hz, 1H), 3.35-3.44 (m, 1H), 3.03 (d, J = 10.6 Hz, 1H), 2.71 (d, J = 11.1 Hz, 1H), 2.31-2.39 (m, 3H), 2.21-2.29 (m, 1H), 2.15 (t, J = 10.6 Hz, 1H) |
| A0021_07_44 | Two diastereoisomers (60/40): ¹H NMR (DMSO-$d_6$ + TFA) δ: 9.27 (s, 1H), 8.97 (t, J = 5.4 Hz, 1H), 7.65-7.81 (m, 1H), 7.38-7.52 (m, 2H), 7.28-7.32 (m, 1H), 7.19-7.27 (m, 1H), 5.01-5.10 (m, 1H), 4.69-4.79 (m, 1H), 4.19-4.43 (m, 1H), 3.60-4.19 (m, 6H), 3.00-3.43 (m, 4H), 2.43-2.48 (m, 3H) |
| A0021_09_01 | ¹H NMR (DMSO-$d_6$) δ: 9.02 (s, 2H), 8.98 (s, 1H), 8.58 (t, J = 5.5 Hz, 1H), 8.34 (dd, J = 8.4, 2.1 Hz, 1H), 8.29 (d, J = 2.0 Hz, 1H), 7.65 (d, J = 8.6 Hz, 1H), 4.19 (t, J = 6.7 Hz, 1H), 3.80-3.90 (m, 1H), 3.49-3.55 (m, 2H), 3.34-3.43 (m, 1H), 2.49-2.53 (m, 1H), 2.31-2.48 (m, 6H), 1.93-2.06 (m, 2H), 1.80-1.93 (m, 2H), 1.65-1.76 (m, 1H), 1.49-1.61 (m, 1H) |
| A0021_09_02 | ¹H NMR (DMSO-$d_6$) δ: 9.01 (s, 2H), 8.97 (s, 1H), 8.59 (dd, J = 7.1, 2.3 Hz, 1H), 8.45 (ddd, J = 8.6, 5.0, 2.3 Hz, 1H), 8.31-8.37 (m, 1H), 7.46 (dd, J = 10.3, 8.8 Hz, 1H), 4.23 (t, J = 6.8 Hz, 1H), 3.81-3.91 (m, 1H), 3.47-3.55 (m, 2H), 3.36-3.47 (m, 1H), 2.50 (s, 1H), 2.31-2.43 (m, 6H), 1.80-2.05 (m, 4H), 1.64-1.75 (m, 1H), 1.49-1.61 (m, 1H) |
| A0021_11_01 | ¹H NMR (DMSO-$d_6$ + TFA) δ: 9.31 (s, 1H), 8.94 (t, J = 5.5 Hz, 1H), 7.38-7.48 (m, 1H), 7.11-7.33 (m, 3H), 4.97-5.07 (m, 1H), 4.05-4.14 (m, 1H), 3.72 (m, 1H), 3.08-3.27 (m, 2H), 2.91-3.08 (m, 2H), 2.10-2.27 (m, 4H) |
| A0021_07_33 | ¹H NMR (DMSO-$d_6$) δ: 8.96 (s, 1H), 8.71 (t, J = 5.7 Hz, 1H), 7.45 (td, J = 8.2, 6.2 Hz, 1H), 7.31-7.35 (m, 1H), 7.23-7.30 (m, 1H), 4.06-4.12 (m, 1H), 3.81 (dt, J = 13.3, 6.0 Hz, 1H), 3.48 (t, J = 4.8 Hz, 2H), 3.36-3.44 (m, 1H), 2.46-2.52 (m, 1H), 2.37-2.42 (m, 5H), 2.29-2.35 (m, 1H), 1.90-2.03 (m, 2H), 1.81-1.90 (m, 2H), 1.62-1.75 (m, 1H), 1.49-1.61 (m, 1H) |
| A0021_10_01 | Two diastereoisomeri (50/50): ¹H NMR (DMSO-$d_6$ + TFA) δ: 9.30 (s, 1H), 8.99 (s, 2H), 8.83-8.92 (m, 1H), 8.34 (dd, J = 8.4, 1.9 Hz, 1H), 8.15-8.22 (m, 1H), 7.78 (s, 0.5H), 7.70 (s, 0.5H), 7.61 (d, J = 8.3 Hz, 1H), 7.52 (s, 0.5H), 7.43 (s, 0.5H), 5.09-5.20 (m, 1H), 4.68-4.82 (m, 1H), 4.19-4.32 (m, 1H), 3.69-4.18 (m, 6H), 3.20-3.45 (m, 2H), 3.03-3.20 (m, 2H), 2.51 (s, 3H) |
| A0021_10_02 | Two diastereoisomer (55/45): ¹H NMR (DMSO-$d_6$ + TFA) δ: 9.31 (s, 1H), 8.92 (s, 2H), 8.65-8.76 (m, 1H), 8.49-8.55 (m, 1H), 8.39-8.49 (m, 1H), 7.76 (s, 0.45H), 7.68 (s, 0.55H), 7.51 (s, 0.45H), 7.43 (s, 0.55H), 7.37 (t, J = 9.6 Hz, 1H), 5.11-5.23 (m, 1H), 4.69-4.82 (m, 1H), 4.16-4.26 (m, 1H), 3.72-4.16 (m, 6H), 3.20-3.43 (m, 2H), 3.07-3.19 (m, 2H), 2.48 (s, 3H) |

| Compound | ¹H-NMR 400 |
| --- | --- |
| A0021_26_02 | Two diastereoisomer (60/40): ¹H NMR (DMSO-d$_6$ + TFA) δ: 9.22-9.38 (m, 2H), 8.92-9.22 (m, 2H), 8.25-8.40 (m, 1H), 7.90-8.15 (m, 2H), 7.79-7.87 (m, 0.6H), 7.73-7.80 (m, 0.4H), 7.56-7.63 (m, 0.4H), 7.48-7.55 (m, 0.6H), 7.09-7.35 (m, 2H), 4.92-5.20 (m, 2H), 4.11-4.30 (m, 2H), 3.76-4.04 (m, 3H), 2.95-3.40 (m, 4H), 2.46 (s, 1.2H), 2.43 (s, 1.8H) |
| A0021_26_03 | ¹H NMR (DMSO-d$_6$) δ: 8.96 (s, 1H), 8.54 (t, J = 5.7 Hz, 1H), 7.39-7.48 (m, 1H), 7.25-7.30 (m, 2H), 7.16-7.24 (m, 2H), 7.06 (td, J = 8.4, 2.3 Hz, 1H), 4.64-4.71 (m, 1H), 4.25 (t, J = 7.2 Hz, 1H), 3.95 (dd, J = 11.1, 1.5 Hz, 1H), 3.67-3.81 (m, 2H), 3.45-3.54 (m, 1H), 2.95 (d, J = 11.3 Hz, 1H), 2.82 (d, J = 10.8 Hz, 1H), 2.36-2.40 (m, 3H), 2.28-2.36 (m, 1H), 2.14 (s, 3H), 2.04 (t, J = 10.4 Hz, 1H) |
| A0021_26_04 | Diastereoisomer 1 (30%): ¹H NMR (DMSO-d$_6$) δ: 8.96 (s, 1H), 8.54 (t, J = 5.7 Hz, 1H), 7.39-7.48 (m, 1H), 7.25-7.30 (m, 2H), 7.16-7.24 (m, 2H), 7.06 (td, J = 8.4, 2.3 Hz, 1H), 4.64-4.71 (m, 1H), 4.25 (t, J = 7.2 Hz, 1H), 3.95 (dd, J = 11.1, 1.5 Hz, 1H), 3.67-3.81 (m, 2H), 3.45-3.54 (m, 1H), 2.95 (d, J = 11.3 Hz, 1H), 2.82 (d, J = 10.8 Hz, 1H), 2.36-2.40 (m, 3H), 2.28-2.36 (m, 1H), 2.14 (s, 3H), 2.04 (t, J = 10.4 Hz, 1H). Diastereoisomer 2 (70%):: ¹H NMR (DMSO-d$_6$) δ: 8.98 (s, 1H), 8.51-8.59 (m, 1H), 7.38-7.49 (m, 1H), 7.14-7.31 (m, 4H), 7.06 (td, J = 8.6, 2.3 Hz, 1H), 4.73 (d, J = 8.3 Hz, 1H), 4.22-4.29 (m, 1H), 3.95 (d, J = 10.8 Hz, 1H), 3.62-3.80 (m, 2H), 3.38-3.53 (m, 1H), 3.02 (d, J = 11.3 Hz, 1H), 2.75 (d, J = 11.6 Hz, 1H), 2.34 (s, 3H), 2.24 (td, J = 11.2, 2.8 Hz, 1H), 2.10-2.17 (m, 4H) |
| A0021_24_04 | ¹H NMR (DMSO-d$_6$ + TFA) δ: 9.35 (s, 1H), 8.98 (s, 2H), 8.75-8.89 (m, 1H), 8.34 (dd, J = 8.6, 2.0 Hz, 1H), 8.26 (s, 1H), 7.56-7.65 (m, 1H), 7.24 (t, J = 53.1 Hz, 1H), 5.06-5.25 (m, 1H), 4.05-4.20 (m, 1H), 3.63-3.78 (m, 2H), 3.18-3.44 (m, 2H), 2.96-3.18 (m, 2H), 2.12-2.32 (m, 4H) |
| A0021_24_02 | Two diastereoisomer (60/40): ¹H NMR (DMSO-d$_6$ + TFA) δ: 9.32-9.38 (m, 1H), 9.29 (s, 1H), 9.18 (t, J = 5.3 Hz, 1H), 9.02-9.14 (m, 1H), 8.31-8.38 (m, 1H), 8.03-8.17 (m, 2H), 7.75-7.89 (m, 1H), 7.46-7.64 (m, 1H), 7.08-7.36 (m, 2H), 5.11-5.21 (m, 1H), 4.97-5.10 (m, 1H), 3.72-4.34 (m, 5H), 3.06-3.47 (m, 3H), 2.40-2.48 (m, 3H) |
| A0021_25_02 | ¹H NMR (DMSO-d$_6$ + TFA) δ: 9.28 (s, 1H), 9.03 (t, J = 5.4 Hz, 1H), 7.44 (td, J = 8.3, 6.3 Hz, 1H), 7.30 (d, J = 8.3 Hz, 1H), 7.24 (t, J = 8.7 Hz, 1H), 5.12-5.37 (m, 1H), 3.99-4.28 (m, 2H), 3.14-3.92 (m, 3H), 2.19-2.48 (m, 7H), 1.57-1.73 (m, 3H) |
| A0021_38_01 | ¹H NMR (DMSO-d$_6$ + TFA) δ: 9.24-9.38 (m, 1H), 9.01-9.24 (m, 2H), 8.27-8.38 (m, 1H), 7.91-8.18 (m, 3H), 7.83-7.91 (m, 1H), 5.13-5.27 (m, 1H), 4.13-4.27 (m, 1H), 3.82-3.98 (m, 2H), 3.23-3.52 (m, 4H), 2.21-2.46 (m, 8H), 1.95-2.11 (m, 1H), 1.80-1.95 (m, 1H) |
| A0021_38_02 | ¹H NMR (DMSO-d$_6$ + TFA) δ: 8.98 (s, 2H), 8.78 (t, J = 4.9 Hz, 1H), 8.55 (dd, J = 6.9, 2.1 Hz, 1H), 8.43-8.49 (m, 1H), 7.93-7.98 (m, 1H), 7.44 (t, J = 9.4 Hz, 1H), 5.10-5.26 (m, 1H), 4.08-4.19 (m, 1H), 3.80-3.96 (m, 2H), 3.20-3.57 (m, 4H), 2.20-2.47 (m, 8H), 1.96-2.10 (m, 1H), 1.83-1.94 (m, 1H) |
| A0021_39_01 | ¹H NMR (DMSO-d$_6$ + TFA) δ: 8.99 (s, 2H), 8.90 (t, J = 5.5 Hz, 1H), 8.35 (dd, J = 8.6, 2.0 Hz, 1H), 8.25 (d, J = 2.0 Hz, 1H), 7.95 (d, J = 2.8 Hz, 1H), 7.63 (d, J = 8.6 Hz, 1H), 5.05-5.22 (m, 1H), 4.05-4.22 (m, 1H), 3.76-3.95 (m, 1H), 3.18-3.56 (m, 4H), 2.99 (t, J = 7.4 Hz, 2H), 2.22-2.41 (m, 4H), 1.75 (s × t, J = 7.4 Hz, 2H), 0.95 (t, J = 7.3 Hz, 3H) |
| A0021_39_02 | ¹H NMR (DMSO-d$_6$ + TFA) δ: 9.29-9.37 (m, 1H), 9.08-9.23 (m, 2H), 8.30-8.37 (m, 1H), 8.00-8.15 (m, 2H), 7.95-7.99 (m, 1H), 7.84-7.92 (m, 1H), 5.14-5.26 (m, 1H), 4.13-4.26 (m, 1H), 3.87-4.00 (m, 1H), 3.23-3.51 (m, 4H), 2.99 (t, J = 7.6 Hz, 2H), 2.23-2.42 (m, 4H), 1.74 (s × t, J = 7.4 Hz, 2H), 0.88-0.98 (m, 3H) |
| A0021_40_01 | ¹H NMR (DMSO-d$_6$ + TFA) δ: 9.03 (t, J = 5.5 Hz, 1H), 7.92 (d, J = 2.8 Hz, 1H), 7.38-7.54 (m, 1H), 7.29-7.34 (m, 1H), 7.25 (t, J = 8.4 Hz, 1H), 4.93-5.11 (m, 1H), 4.07-4.25 (m, 1H), 3.73-3.92 (m, 1H), 3.13-3.56 (m, 4H), 2.98 (t, J = 7.6 Hz, 2H), 2.19-2.42 (m, 4H), 1.75 (s × t, J = 7.5 Hz, 2H), 0.96 (t, J = 7.3 Hz, 3H) |
| A0020_68_01 | ¹H NMR (DMSO-d$_6$ + TFA) δ: 9.02 (t, J = 5.7 Hz, 1H), 7.93 (d, J = 4.0 Hz, 1H), 7.40-7.49 (m, 1H), 7.29-7.34 (m, 1H), 7.20-7.29 (m, 1H), 5.00-5.11 (m, 1H), 4.12-4.22 (m, 1H), 3.77-3.96 (m, 2H), 3.17-3.56 (m, 4H), 2.21-2.48 (m, 8H), 1.96-2.10 (m, 1H), 1.83-1.95 (m, 1H) |
| A0020_67_01 | ¹H NMR (DMSO-d$_6$ + TFA) δ: 8.99 (s, 2H), 8.86-8.93 (m, 1H), 8.35 (dd, J = 8.6, 2.3 Hz, 1H), 8.26 (d, J = 2.0 Hz, 1H), 7.92-7.99 (m, 1H), 7.63 (d, J = 8.6 Hz, 1H), 5.06-5.22 (m, 1H), 4.08-4.21 (m, 1H), 3.78-3.97 (m, 2H), 3.10-3.63 (m, 4H), 2.19-2.48 (m, 8H), 1.97-2.10 (m, 1H), 1.83-1.95 (m, 1H) |

| Compound | ¹H-NMR 400 |
| --- | --- |
| A0020_71_01 | ¹H NMR (DMSO-d₆ + TFA) δ: 8.99 (s, 2H), 8.92 (t, J = 5.3 Hz, 1H), 8.35 (dd, J = 8.4, 2.1 Hz, 1H), 8.25 (d, J = 2.0 Hz, 1H), 7.98 (d, J = 3.0 Hz, 1H), 7.63 (d, J = 8.6 Hz, 1H), 5.08-5.29 (m, 1H), 4.77 (s, 2H), 4.12-4.25 (m, 1H), 3.78-3.92 (m, 1H), 3.17-3.63 (m, 4H), 2.22-2.44 (m, 4H), 1.11 (s, 1H) |
| A0016_60_01 | ¹H NMR (DMSO-d₆ + TFA) δ: 9.17-9.32 (m, 1H), 8.63 (t, J = 4.8 Hz, 1H), 7.23-7.28 (m, 1H), 7.15-7.22 (m, 2H), 5.02-5.14 (m, 1H), 4.05-4.17 (m, 1H), 3.76 (t, J = 6.5 Hz, 2H), 3.62-3.73 (m, 1H), 3.34-3.61 (m, 4H), 3.18-3.34 (m, 2H), 2.46 (s, 3H), 2.41 (quin, J = 6.9 Hz, 2H), 2.21-2.36 (m, 4H) |
| A0016_54_01 | ¹H NMR (DMSO-d₆ + TFA) δ: 9.17-9.32 (m, 1H), 9.04-9.17 (m, 1H), 8.80-9.04 (m, 1H), 8.18-8.36 (m, 1H), 7.67-8.14 (m, 4H), 5.07-5.32 (m, 1H), 4.11-4.33 (m, 1H), 3.75-4.04 (m, 5H), 2.97-3.66 (m, 5H), 1.88-2.18 (m, 6H), 1.68-1.87 (m, 2H) |
| A0016_52_01 | ¹H NMR (DMSO-d₆ + TFA) δ: 9.00 (t, J = 5.7 Hz, 1H), 7.92 (s, 1H), 7.46 (td, J = 8.3, 6.3 Hz, 1H), 7.29-7.34 (m, 1H), 7.21-7.29 (m, 1H), 5.06 (dd, J = 10.2, 3.1 Hz, 1H), 4.18 (dt, J = 13.0, 4.6 Hz, 1H), 3.73-4.03 (m, 5H), 3.03-3.66 (m, 5H), 1.92-2.19 (m, 6H), 1.70-1.84 (m, 2H) |
| A0016_49_01 | ¹H NMR (DMSO-d₆ + TFA) δ: 8.93-9.05 (m, 1H), 7.91 (d, J = 4.3 Hz, 1H), 7.45 (td, J = 8.1, 6.4 Hz, 1H), 7.20-7.38 (m, 2H), 4.85-5.15 (m, 1H), 4.04-4.25 (m, 1H), 3.75-3.96 (m, 1H), 3.08-3.54 (m, 5H), 2.22-2.39 (m, 4H), 1.91-2.21 (m, 6H), 1.64-1.85 (m, 2H) |
| A0016_63_01 | ¹H NMR (DMSO-d₆ + TFA) δ: 9.02 (t, J = 5.5 Hz, 1H), 7.92 (s, 1H), 7.37-7.51 (m, 1H), 7.17-7.35 (m, 2H), 5.02-5.19 (m, 1H), 4.05-4.24 (m, 1H), 3.79-3.99 (m, 1H), 3.18-3.63 (m, 4H), 2.19-2.41 (m, 4H), 1.39 (d, J = 1.8 Hz, 9H) |
| A0016_67_01 | ¹H NMR (DMSO-d₆ + TFA) δ: 9.15 (s, 1H), 8.98 (d, J = 3.5 Hz, 2H), 8.91 (t, J = 5.5 Hz, 1H), 8.34 (dd, J = 8.6, 2.3 Hz, 1H), 8.23 (d, J = 2.3 Hz, 1H), 7.62 (dd, J = 8.4, 2.9 Hz, 1H), 5.29-5.42 (m, 1H), 4.21-4.34 (m, 1H), 3.25-3.87 (m, 5H), 2.24-2.44 (m, 5H), 0.78-1.07 (m, 4H) |
| A0016_61_01 | ¹H NMR (DMSO-d₆ + TFA) δ: 10.36 (s, 1H), 9.25 (s, 1H), 8.19-8.35 (m, 1H), 7.42 (d, J = 7.8 Hz, 1H), 6.65 (d, J = 12.1 Hz, 1H), 5.05-5.20 (m, 1H), 4.00-4.15 (m, 1H), 3.64-3.80 (m, 1H), 3.40-3.64 (m, 2H), 3.20-3.40 (m, 2H), 2.87 (t, J = 7.68 Hz, 2H), 2.42-2.49 (m, 5H), 2.18-2.39 (m, 4H) |
| A0016_68_01 | ¹H NMR (DMSO-d₆ + TFA) δ: 9.28-9.40 (m, 1H), 9.04-9.26 (m, 2H), 8.28-8.42 (m, 1H), 7.99-8.20 (m, 2H), 7.80-7.95 (m, 1H), 5.37-5.53 (m, 1H), 4.28 (dt, J = 13.4, 5.3 Hz, 1H), 3.87 (dt, J = 13.6, 7.1 Hz, 1H), 3.31-3.75 (m, 4H), 2.25-2.44 (m, 5H), 0.78-1.04 (m, 4H) |
| A0016_64_01 | ¹H (NMR DMSO-d₆ + TFA) δ: 8.96 (s, 2H), 8.90 (t, J = 5.5 Hz, 1H), 8.35 (dd, J = 8.4, 2.1 Hz, 1H), 8.26 (d, J = 2.3 Hz, 1H), 7.91-8.00 (m, 1H), 7.58-7.65 (m, 1H), 5.13-5.28 (m, 1H), 4.05-4.19 (m, 1H), 3.84-3.99 (m, 1H), 3.13-3.71 (m, 4H), 2.22-2.44 (m, 4H), 1.34 (s, 9H) |
| A0016_66_01 | ¹H NMR (DMSO-d₆ + TFA) δ: 9.13 (s, 1H), 9.03 (t, J = 5.7 Hz, 1H), 7.36-7.50 (m, 1H), 7.14-7.36 (m, 2H), 5.20-5.35 (m, 1H), 4.22-4.37 (m, 1H), 3.68-3.85 (m, 1H), 3.23-3.68 (m, 4H), 2.21-2.42 (m, 5H), 0.78-1.08 (m, 4H) |
| A0016_65_01 | ¹H NMR (DMSO-d₆ + TFA) δ: 9.28-9.39 (m, 1H), 9.09-9.27 (m, 2H), 8.29-8.39 (m, 1H), 8.00-8.17 (m, 2H), 7.89-8.02 (m, 1H), 7.82-7.89 (m, 1H), 5.17-5.32 (m, 1H), 4.14-4.28 (m, 1H), 3.87-4.03 (m, 1H), 3.17-3.64 (m, 4H), 2.24-2.44 (m, 4H), 1.41 (s, 9H) |
| A0016_53_01 | ¹H NMR (DMSO-d₆ + TFA) δ: 9.00 (s, 2H), 8.87 (t, J = 5.7 Hz, 1H), 8.34 (dd, J = 8.6, 1.0 Hz, 1H), 8.21 (d, J = 2.0 Hz, 1H), 7.95 (s, 2H), 7.63 (d, J = 8.3 Hz, 1H), 5.06-5.21 (m, 1H), 4.15 (dt, J = 13.5, 4.7 Hz, 1H), 3.74-4.01 (m, 5H), 3.07-3.73 (m, 4H), 1.90-2.21 (m, 7H), 1.67-1.87 (m, 2H) |
| A0016_50_01 | ¹H NMR (DMSO-d₆ + TFA) δ: 8.98 (s, 2H), 8.88 (t, J = 5.5 Hz, 1H), 8.28-8.39 (m, 1H), 8.23 (d, J = 2.3 Hz, 1H), 7.98 (s, 1H), 7.58-7.66 (m, 1H), 5.10-5.26 (m, 1H), 4.07-4.20 (m, 1H), 3.82-3.97 (m, 1H), 3.19-3.67 (m, 5H), 2.22-2.41 (m, 4H), 1.91-2.20 (m, 6H), 1.69-1.83 (m, 2H) |
| A0016_99_01 | ¹H NMR (DMSO-d₆ + TFA) Shift: 9.42 (s, 1H), 8.91-9.01 (m, 2H), 8.87 (t, J = 5.7 Hz, 1H), 8.33 (dd, J = 8.4, 2.1 Hz, 1H), 8.21 (d, J = 2.0 Hz, 1H), 7.59 (dd, J = 8.3, 1.5 Hz, 1H), 7.31 (t, J = 52.4 Hz, 1H), 5.24-5.39 (m, 1H), 4.18-4.30 (m, 1H), 3.69-3.93 (m, 5H), 3.31-3.58 (m, 2H), 3.04-3.24 (m, 2H) |
| A0022_02_01 | ¹H NMR (DMSO-d₆ + TFA) Shift: 9.39 (s, 1H), 9.00 (t, J = 5.4 Hz, 1H), 7.35-7.52 (m, 1H), 7.09-7.33 (m, 3H), 5.16-5.33 (m, 1H), 4.20-4.38 (m, 1H), 3.69-3.96 (m, 5H), 3.28-3.57 (m, 2H), 2.98-3.20 (m, 2H) |

Pharmacological Examples

Examples of the Invention were found to be P2X7 inhibitors using a Screen Quest™ Fluo-8 No Wash Calcium Assay Kit.

Extracellular binding of Bz-ATP to P2X7 receptor opens the channel and allows Ca2+ influx into the cells. This Ca2+ entry was measured in HEK-293 cells stably transfected with P2X7 receptor using Screen Quest™ Fluo-8 No Wash Calcium Assay Kit (AAt Bioquest®, cat. 36316). Once inside the cell, the lipophilic blocking groups of Fluo-8 are cleaved by non-specific cell esterases, resulting in a negatively-charged fluorescent dye that stays inside cells. Its fluorescence increases upon binding to calcium. When HEK-293/P2X7 cells are stimulated with Bz-ATP, Ca2+ enters the cells and the fluorescence of Fluo-8 NW increases. The dye has an absorption spectrum compatible with excitation at 488 nm by argon laser sources and its emission wavelength is in the range of 515-575 nm.

HEK-293 cells stably transfected with P2X7 receptor were seeded overnight in growth medium at 10,000 to 20,000 cells/well in 384-well plate. 24 hours later, the medium was removed and the cells were pre-loaded at RT for 1 hour with 20 μL/w of Fluo-8 NW. Then 10 μL/w of test compounds and reference antagonist A438079 at 3×-concentration were injected with the FLIPR$_{TETRA}$ and the kinetic response over a period of five minutes was monitored. A second injection of 15 μL/w of 3× reference activator (Bz-ATP at EGO was performed with the FLIPR$_{TETRA}$ and the signal of the emitted fluorescence was recorded for additional three minutes. All the experiment was carried out in a Low Divalent Cation Assay Buffer (0.3 mM Ca2+ and 0 mM Mg2+). The effect of the test compounds was measured as percent inhibition vs the reference antagonist and IC$_{50}$ values were calculated accordingly.

| Compound | hP2X7 (IC$_{50}$; nM) | Example | hP2X7 (IC$_{50}$; nM) |
|---|---|---|---|
| 1 | 1020 | 70 | 32 |
| 2 | 306 | 71 | 355 |
| 4 | 845 | 72 | 30 |
| 5 | 7430 | 73 | 238 |
| 6 | 800 | 74 | 55 |
| 7 | 840 | 75 | 30 |
| 8 | 28 | 76 | 238 |
| 9 | 100 | 77 | 1756 |
| 10 | 57 | 78 | 133 |
| 11 | 81 | 79 | 206 |
| 12 | 143 | 80 | 292 |
| 13 | 64 | 81 | 38 |
| 14 | 27 | 82 | 737 |
| 15 | 8 | 83 | 487 |
| 16 | 32 | 84 | 218 |
| 17 | 136 | 85 | 62 |
| 18 | 90 | 86 | 495 |
| 19 | 104 | 87 | 179 |
| 20 | 34 | 88 | 36 |
| 21 | 31 | 89 | 57 |
| 23 | 118 | 90 | 412 |
| 24 | 111 | 91 | 72 |
| 25 | 48 | 92 | 171 |
| 26 | 119 | 93 | 116 |
| 27 | 63 | 94 | 321 |
| 29 | 130 | 95 | 54 |
| 30 | 46 | 96 | 989 |
| 31 | 31 | 97 | 139 |
| 32 | 55 | 98 | 142 |
| 33 | 158 | 99 | 32 |
| 34 | 111 | 100 | 68 |
| 35 | 469 | 101 | 114 |
| 36 | 149 | 102 | 60 |
| 37 | 106 | 103 | 186 |
| 38 | 87 | 104 | 1868 |

-continued

| Compound | hP2X7 (IC$_{50}$; nM) | Example | hP2X7 (IC$_{50}$; nM) |
|---|---|---|---|
| 39 | 28 | 105 | 292 |
| 40 | 30 | 106 | 1237 |
| 41 | 853 | 107 | 631 |
| 44 | 677 | 108 | 199 |
| 46 | 18 | 109 | 78 |
| 47 | 43 | 110 | 119 |
| 48 | 541 | 111 | 1015 |
| 49 | 104 | 112 | 119 |
| 50 | 4967 | 113 | 743 |
| 51 | 101 | 114 | 367 |
| 54 | 114 | 115 | 117 |
| 56 | 147 | 116 | 60 |
| 57 | 214 | 117 | 429 |
| 58 | 1121 | 118 | 243 |
| 59 | 242 | 119 | 319 |
| 60 | 188 | 120 | 6908 |
| 61 | 280 | 121 | 531 |
| 62 | 576 | 122 | 1060 |
| 63 | 69 | 123 | 279 |
| 64 | 253 | 124 | 3946 |
| 65 | 39 | 125 | 336 |
| 66 | 22 | 126 | 1428 |
| 67 | 108 | 127 | 73 |
| 68 | 103 | 128 | 141 |
| 69 | 98 | 129 | 32 |
|  |  | 130 | 22 |

Examples of the Invention were found to be P2X7 inhibitors using a YO-PRO®-1 Uptake Assay.

YO-PRO®-1 is a fluorescent DNA-binding dye with a MW of 374 Da (Molecular Probes®, cat. Y3603). This method is based upon the presumed ability of YO-PRO®-1 to enter through the dilated or "large pore form" of P2X7 receptor and to bind to intracellular DNA whereupon it increases many fold its fluorescence intensity. The dye has an absorption spectrum compatible with excitation at 488 nm by argon laser sources and its emission wavelength is in the range of 515-575 nm. The aim of this assay was to validate the interaction of antagonists with P2X7 receptor using an alternative readout to Ca$^{2+}$-sensitive fluorescent dyes.

HEK-293 cells stably transfected with P2X7 receptor were seeded overnight in growth medium at 20,000 cells/well in 384-well plate. 24 hours later, the medium was removed, the cells were washed with Low Divalent Cation Assay Buffer (0.3 mM Ca2+ and 0 mM Mg2+) and then pre-loaded with 20 μL/w of 5 μM YO-PRO®-1 dye. FLIPR$_{TETRA}$ fluorescence measurement immediately started. Then, 10 μL/w of test compounds and reference antagonist A438079 at 3×-concentration were injected with the FLIPR$_{TETRA}$ and the kinetic response over a period of five minutes was monitored. A second injection of 10 μL/w of 3× Bz-ATP EC80 (30 μM) was performed with the FLIPR$_{TETRA}$ and the signal of the emitted fluorescence was recorded for additional 60 minutes. All the experiment was carried out with a Low Divalent Cation Assay Buffer (0.3 mM Ca$^{2+}$ and 0 mM Mg$^{2+}$).

The effect of the test compounds was measured as percent inhibition vs the reference antagonist and IC$_{50}$ values were calculated accordingly.

| Compound | YO-PRO®-1 Uptake Assay (IC$_{50}$; nM) | Example | YO-PRO®-1 Uptake Assay (IC$_{50}$; nM) |
|---|---|---|---|
| 1 | 1356 | 51 | 71 |
| 2 | 1300 | 52 | 2067 |
| 4 | 3300 | 53 | 4903 |

| Compound | YO-PRO ®-1 Uptake Assay (IC$_{50}$; nM) | Example | YO-PRO ®-1 Uptake Assay (IC$_{50}$; nM) |
|---|---|---|---|
| 5 | 7430 | 54 | 279 |
| 6 | 1255 | 56 | 414 |
| 7 | 1687 | 57 | 197 |
| 8 | 389 | 58 | 2971 |
| 9 | 464 | 59 | 55 |
| 10 | 57 | 60 | 79 |
| 11 | 220 | 61 | 124 |
| 12 | 846 | 62 | 1107 |
| 13 | 271 | 63 | 158 |
| 14 | 24 | 66 | 58 |
| 15 | 38 | 67 | 287 |
| 16 | 98 | 68 | 181 |
| 17 | 690 | 70 | 183 |
| 18 | 190 | 72 | 60 |
| 19 | 197 | 74 | 87 |
| 20 | 30 | 75 | 28 |
| 21 | 129 | 76 | 637 |
| 23 | 40 | 81 | 16 |
| 24 | 44 | 84 | 61 |
| 25 | 42 | 85 | 48 |
| 26 | 44 | 87 | 126 |
| 27 | 52 | 88 | 28 |
| 29 | 90 | 89 | 75 |
| 30 | 37 | 91 | 53 |
| 31 | 229 | 93 | 82 |
| 32 | 44 | 95 | 82 |
| 33 | 176 | 99 | 79 |
| 34 | 41 | 100 | 72 |
| 35 | 4083 | 101 | 42 |
| 36 | 302 | 102 | 34 |
| 37 | 90 | 105 | 135 |
| 38 | 49 | 106 | 807 |
| 39 | 18 | 107 | 158 |
| 40 | 18 | 108 | 77 |
| 41 | 996 | 109 | 50 |
| 44 | 500 | 110 | 46 |
| 45 | 225 | 111 | 326 |
| 46 | 55 | 112 | 36 |
| 47 | 36 | 115 | 32 |
| 48 | 1068 | 116 | 41 |
| 49 | 945 | 127 | 22 |
| 50 | 2094 | 128 | 24 |
| | | 129 | 27 |
| | | 130 | 26 |

Examples of the Invention were found to be active on a human P2X7 channel assay by automated patch-clamp.

In order to directly monitor the block of P2X7 channel, an electrophysiological assay was developed and implemented on the QPatch 16X automated electrophysiology instrument.

HEK-293 cells expressing the P2X7 channels were cultured in modified EMEM.

72 hours before experiment, 5 million cells were seeded onto T225 flasks. Just before the experiment cells were washed twice, detached from the flask with trypsin-EDTA, re-suspended in the suspension solution and placed on the QPatch 16x.

The compounds (20 mM in a 100% DMSO) stored at −20° C. were prepared the day of the experiment (a first dilution 1:20 in 100% DMSO to prepare a 1 mM stock solution, then a 1 microM solution in external solution+a serial dilution 1:10).

The standard whole-cell voltage clamp experiments were performed at room temperature. For these experiments the multihole technology was used and the data were sampled at 2 KHz.

The intracellular solution contained (mM) 135 CsF, 10 NaCl, 1 EGTA, 10 HEPES, (pH 7.2 with CsOH) whereas the extracellular contained (mM) 145 NaCl, 4 KCl, 0.5 MgCl$_2$, 1 CaCl$_2$, 10 HEPES, 10 Glc (pH 7.4 with NaOH).

After establishment of the seal and the passage in the whole cell configuration, the cells were held at −80 mV. The P2XR7 current was evoked by applying 100 microM of BzATP alone (4 times) and then in the presence increasing concentrations of the compound under investigation (1, 10, 100 and 1000 nM).

The pre-incubation periods 5 to 8 contain increasing concentrations of the compound of interest (1, 10, 100 and 1000 nM), as illustrated in Figure (application protocol).

The maximal inward current evoked by BzATP in absence or presence of increasing concentrations of the compounds under investigation was measured and normalized. The potential agonist effect was measured as % of control and as IC$_{50}$ determined fitting the dose-response curves data with the following equation:

$$Y=100/(1+10\textasciicircum((\text{Log } IC50-X)*\text{HillSlope}))$$

where:
X: log of concentration
Y: normalized response, 100% down to 0%, decreasing as X increases.
Log IC$_{50}$: same log units as X
HillSlope: slope factor or HS, unitless

| Compound | hP2X7 (IC$_{50}$; nM) | ±SEM |
|---|---|---|
| 14 | 22.74 | 3.17 |
| 29 | 36.13 | 7.54 |
| 34 | 130.70 | 7.56 |
| 35 | 947 | 184 |
| 39 | 61.91 | 12.79 |
| 47 | 33.93 | 4.78 |
| 57 | 70.99 | 16.31 |
| 59 | 69.21 | 17.52 |
| 60 | 58.87 | 10.25 |
| 61 | 56.33 | 12.63 |
| 66 | 82.49 | 8.86 |
| 67 | 117.13 | 18.26 |
| 68 | 63.13 | 0.63 |
| 69 | 31.41 | 2.15 |
| 70 | 58.40 | 9.19 |
| 72 | 78.09 | 15.42 |
| 74 | 65.22 | 2.01 |
| 76 | 35.88 | 1.42 |
| 77 | 183.13 | 55.36 |
| 88 | 52.06 | 6.02 |
| 102 | 57.12 | 8.84 |
| 127 | 65.72 | 13.57 |

The invention claimed is:
1. A compound of the following formula (I) or a pharmaceutically acceptable salt thereof:

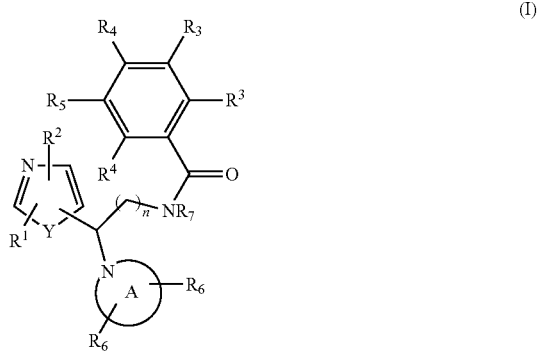

including any stereochemically isomeric form thereof, wherein n is 1 or 2;
Y represents oxygen or sulfur;
each of $R^1$ and $R^2$ is independently selected from the group consisting of hydrogen, deuterium, halogen, C1-C4 alkyl, optionally substituted with hydroxy or halogen, such as hydroxymethyl, fluoromethyl, difluoromethyl, trifluoromethyl, C3-C6 cycloalkyl, optionally substituted with hydroxy or halogen, or C1-C4 alkyloxy; each of $R^3$ and $R^4$ is independently selected from the group consisting of hydrogen, halogen, C1-C4 alkyl, difluoromethyl, trifluoromethyl, C1-C4 alkyloxy, $NR^9R^{10}$, wherein $R^9$ and $R^{10}$ independently are hydrogen or C1-C4 alkyl, or 2-thiazolidin-1,1-dione; or the two $R^3$ groups or the $R^3$ and $R^4$ groups taken together form a six membered heterocyclic ring containing a nitrogen atom;
$R^5$ is selected from hydrogen, halogen, or is an heterocyclic ring selected from pyrimidin-2-yl, pyridin-2-yl or pyrazin-2-yl, optionally substituted with halogen, C1-C4 alkyl, fluoromethyl, difluoromethyl, trifluoromethyl or C1-C4 alkyloxy;
$R^7$ is hydrogen or C1-C4 alkyl;
the radical

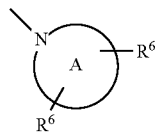

represents an optionally substituted azetidine, pyrrolidine, piperidine, morpholine, oxazepane or 1,2,3,4-tetrahydroisoquinoline ring, wherein each of $R^6$ is independently selected from the group consisting of hydrogen, halogen, C1-C4 alkyl, C3-C6 cycloalkyl, C3-C6 spirocycloalkyl difluoromethyl, trifluoromethyl, C1-C4 alkyloxy, aryl, heteroaryl, C1-C4 aryloxy or C1-C4 arylalkoxy wherein the aryl group or heteroaryl group is optionally substituted with halogen C1-C4 alkyl, fluoromethyl, difluoromethyl, trifluoromethyl or C1-C4 alkyloxy.

2. A compound of Formula (I) according to claim 1 wherein $R_7$ is hydrogen and n is 1.

3. A compound of Formula (I) according to claim 1 wherein both $R^1$ and $R^2$ are hydrogen or one is hydrogen and the other is methyl, ethyl, propyl, tert-butyl, optionally substituted with hydroxy or fluorine, C3-C6 cycloalkyl, optionally substituted with hydroxy or fluorine.

4. A compound of Formula (I) according to claim 1 wherein $R^5$ is hydrogen and each of $R^3$ and $R^4$ independently is hydrogen, halogen, C1-C4 alkyl, C1-C4 alkyloxy, $NR^9R^{10}$, wherein $R^9$ and $R^{10}$ independently are hydrogen or C1-C4 alkyl, or 2-thiazolidin-1,1-dione; or the two $R^3$ groups or the $R^3$ and $R^4$ groups taken together form a six membered heterocyclic ring containing a nitrogen atom.

5. A compound of Formula (I) according to claim 1 wherein $R^4$ is hydrogen, the $R^3$ in meta position is hydrogen and the $R^3$ in ortho position is selected from the group consisting of halogen, or C1-C4 alkyl, and $R^5$ is an heterocyclic ring selected from pyrimidin-2-yl, pyridin-2-yl or pyrazin-2-yl, optionally substituted with halogen.

6. A compound of Formula (I) according to claim 1 wherein the ring A is selected from the group consisting of

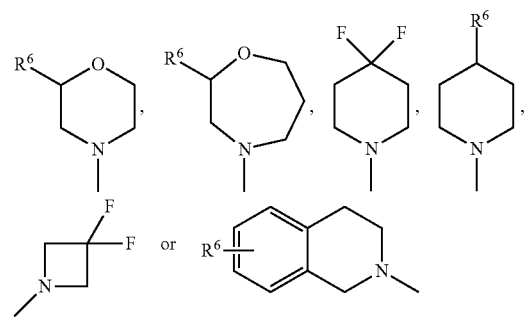

wherein $R^6$ is hydrogen, halogen, benzyloxy or phenoxy, phenyl, pyrazole, C3-C6 cycloalkyl, optionally substituted with halogen, preferably substituted with fluoro.

7. A compound of Formula (I) according to claim 1 selected from the group consisting of:

| Compound | IUPAC NAME |
|---|---|
| 1 | 2-chloro-N-[2-(3,4-dihydro-1H-isoquinolin-2-yl)-2-(1,3-thiazol-2-yl)-ethyl]-6-fluoro-benzamide |
| 2 | 2-chloro-N-[2-(4,4-difluoro-piperidin-1-yl)-2-(1,3-thiazol-2-yl)-ethyl]-6-fluoro-benzamide |
| 3 | 2-chloro-6-fluoro-N-[2-(morpholin-4-yl)-2-(1,3-thiazol-2-yl)ethyl]benzamide |
| 4 | 2-chloro-N-[2-(4,4-difluoropiperidin-1-yl)-2-(1,3-thiazol-4-yl)ethyl]-6-fluorobenzamide |
| 5 | 2-chloro-6-fluoro-N-[2-(morpholin-4-yl)-2-(1,3-thiazol-4-yl)ethyl]benzamide |
| 6 | 2-chloro-N-[2-(3,4-dihydro-1H-isoquinolin-2-yl)-2-(1,3-thiazol-4-yl)-ethyl]-6-fluoro-benzamide |
| 7 | 2-chloro-6-fluoro-N-[2-(4-methyl-1,3-thiazol-5-yl)-2-(1,4-oxazepan-4-yl)ethyl]benzamide; 2-hydroxy-2-oxo-acetate |
| 8 | 2-chloro-N-[2-(4,4-difluoro-piperidin-1-yl)-2-(1,3-thiazol-5-yl)ethyl]-6-fluoro-benzamide |
| 9 | 2-chloro-N-[2-(3,4-dihydro-1H-isoquinolin-2-yl)-2-(1,3-thiazol-5-yl)-ethyl]-6-fluoro-benzamide |
| 10 | 2-chloro-6-fluoro-N(2-(morpholin-4-yl)-2-(thiazol-5-yl)-ethyl)benzamide |
| 11 | 2,6-dimethyl-N-[2-(morpholin-4-yl)-2-(1,3-thiazol-5-yl)ethyl]benzamide |
| 12 | 5-amino-2-chloro-N-[2-(morpholin-4-yl)-2-(1,3-thiazol-5-yl)ethyl]benzamide- |
| 13 | 2-chloro-6-methyl-N-[2-(morpholin-4-yl)-2-(1,3-thiazol-5-yl)ethyl]benzamide |
| 14 | N-[2-(4,4-difluoropiperidin-1-yl)-2-(1,3-thiazol-5-yl)ethyl]-2,6-dimethylbenzamide |
| 15 | 2-chloro-N-[2-(4,4-difluoropiperidin-1-yl)-2-(1,3-thiazol-5-yl)ethyl]-6-methylbenzamide |
| 16 | 5-amino-2-chloro-N-[2-(4,4-difluoropiperidin-1-yl)-2-(1,3-thiazol-5-yl)ethyl]benzamide |
| 17 | 5-amino-2-chloro-N-[2-(1,2,3,4-tetrahydroisoquinolin-2-yl)-2-(1,3-thiazol-5-yl)ethyl]benzamide |
| 18 | 2,6-dimethyl-N-[2-(1,2,3,4-tetrahydroisoquinolin-2-yl)-2-(1,3-thiazol-5-yl)ethyl]benzamide |
| 19 | 2-chloro-6-methyl-N-[2-(1,2,3,4-tetrahydroisoquinolin-2-yl)-2-(1,3-thiazol-5-yl)ethyl]benzamide |
| 20 | 2-chloro-N-[2-(4,4-difluoropiperidin-1-yl)-2-(1,3-thiazol-5-yl)ethyl]-5-(5-fluoropyrimidin-2-yl)-benzamide |
| 21 | N-[2-(4,4-difluoropiperidin-1-yl)-2-(1,3-thiazol-5-yl)ethyl]-2,3-dimethoxybenzamide |
| 22 | N-[2-(4,4-difluoropiperidin-1-yl)-2-(1,3-thiazol-5-yl)ethyl]-2,6-difluorobenzamide |
| 23 | N-{2-[4-(benzyloxy)piperidin-1-yl]-2-(1,3-thiazol-5-yl)ethyl}-2,6-dimethylbenzamide |
| 24 | N-{2-[4-(benzyloxy)piperidin-1-yl]-2-(1,3-thiazol-5-yl)ethyl}-2-chloro-6-methylbenzamide |
| 25 | N-{2-[4-(benzyloxy)piperidin-1-yl]-2-(1,3-thiazol-5-yl)ethyl}-2-chloro-6-fluorobenzamide |
| 26 | 2,6-dimethyl-N-[2-(4-phenoxypiperidin-1-yl)-2-(1,3-thiazol-5-yl)ethyl]benzamide |

| Compound | IUPAC NAME |
|---|---|
| 27 | 2-chloro-6-fluoro-N-[2-(4-phenoxypiperidin-1-yl)-2-(1,3-thiazol-5-yl)ethyl]benzamide |
| 28 | 2-chloro-6-fluoro-N-[2-(piperidin-1-yl)-2-(1,3-thiazol-5-yl)ethyl]benzamide |
| 29 | 2-chloro-6-fluoro-N-[2-(4-methyl-1,3-thiazol-5-yl)-2-(1,2,3,4-tetrahydroisoquinolin-2-yl)ethyl]benzamide |
| 30 | 2,6-dimethyl-N-[2-(4-methyl-1,3-thiazol-5-yl)-2-(1,2,3,4-tetrahydroisoquinolin-2-yl)ethyl]benzamide |
| 31 | 2-chloro-N-[2-(4,4-difluoropiperidin-1-yl)-2-(4-methyl-1,3-thiazol-5-yl)ethyl]-6-fluorobenzamide |
| 32 | N-[2-(4,4-difluoropiperidin-1-yl)-2-(4-methyl-1,3-thiazol-5-yl)ethyl]-2,6-dimethylbenzamide |
| 33 | N-[2-(4,4-difluoropiperidin-1-yl)-2-(4-methyl-1,3-thiazol-5-yl)ethyl]quinoline-5-carboxamide |
| 34 | 2-chloro-N-[2-(4,4-difluoropiperidin-1-yl)-2-(4-methyl-1,3-thiazol-5-yl)ethyl]-5-(5-fluoropyrimidin-2-yl)benzamide |
| 35 | 2-chloro-6-fluoro-N-[2-(4-methyl-1,3-thiazol-5-yl)-2-(morpholin-4-yl)ethyl]benzamide |
| 36 | 2,6-dimethyl-N-[2-(4-methyl-1,3-thiazol-5-yl)-2-(morpholin-4-yl)ethyl]benzamide |
| 37 | 2-chloro-5-(5-fluoropyrimidin-2-yl)-N-[2-(4-methyl-1,3-thiazol-5-yl)-2-(morpholin-4-yl)ethyl]benzamide |
| 38 | 2-chloro-N-[2-(4,4-difluoropiperidin-1-yl)-2-(2-methyl-1,3-thiazol-5-yl)ethyl]-6-fluorobenzamide |
| 39 | 2-chloro-N-[2-(4,4-difluoropiperidin-1-yl)-2-(2-methyl-1,3-thiazol-5-yl)ethyl]-6-methylbenzamide |
| 40 | N-[2-(4,4-difluoropiperidin-1-yl)-2-(2-methyl-1,3-thiazol-5-yl)ethyl]-2,6-dimethylbenzamide |
| 41 | 2-chloro-6-methyl-N-[2-(2-methyl-1,3-thiazol-5-yl)-2-(1,2,3,4-tetrahydroisoquinolin-2-yl)ethyl]benzamide |
| 42 | 2,6-dimethyl-N-[2-(2-methyl-1,3-thiazol-5-yl)-2-(1,2,3,4-tetrahydroisoquinolin-2-yl)ethyl]benzamide |
| 43 | 2-chloro-6-fluoro-N-[2-(2-methyl-1,3-thiazol-5-yl)-2-(1,2,3,4-tetrahydroisoquinolin-2-yl)ethyl]benzamide |
| 44 | 2-chloro-6-fluoro-N-[2-(morpholin-4-yl)-2-(1,3-oxazol-5-yl)ethyl]benzamide |
| 45 | 2-chloro-N-[2-(4,4-difluoropiperidin-1-yl)-2-(1,3-oxazol-5-yl)ethyl]-6-fluorobenzamide |
| 46 | N-[2-(4,4-difluoropiperidin-1-yl)-2-(1,3-oxazol-5-yl)ethyl]-2,6-dimethylbenzamide |
| 47 | 2-chloro-N-[2-(4,4-difluoropiperidin-1-yl)-2-(1,3-oxazol-5-yl)ethyl]-5-(5-fluoropyrimidin-2-yl)benzamide |
| 48 | 2-chloro-6-fluoro-N-[2-(1,3-oxazol-5-yl)-2-(1,2,3,4-tetrahydroisoquinolin-2-yl)ethyl]benzamide |
| 49 | 2,6-dimethyl-N-[2-(1,3-oxazol-5-yl)-2-(1,2,3,4-tetrahydroisoquinolin-2-yl)ethyl]benzamide |
| 50 | N-[2-(4,4-difluoropiperidin-1-yl)-2-(4-methyl-1,3-oxazol-5-yl)ethyl]-2,3-dimethoxybenzamide |
| 51 | 2-chloro-N-[2-(4,4-difluoropiperidin-1-yl)-2-(4-methyl-1,3-oxazol-5-yl)ethyl]-5-(5-fluoropyrimidin-2-yl)benzamide |
| 52 | 2-chloro-N-[2-(4,4-difluoropiperidin-1-yl)-2-(4-methyl-1,3-oxazol-5-yl)ethyl]-6-fluorobenzamide |
| 53 | 2,3-dimethoxy-N-[2-(4-methyl-1,3-oxazol-5-yl)-2-(morpholin-4-yl)ethyl]benzamide |
| 54 | 2-chloro-5-(5-fluoropyrimidin-2-yl)-N-[2-(4-methyl-1,3-oxazol-5-yl)-2-(morpholin-4-yl)ethyl]benzamide |
| 55 | 2-chloro-6-fluoro-N-[2-(4-methyl-1,3-oxazol-5-yl)-2-(morpholin-4-yl)ethyl]benzamide |
| 56 | 2,3-dimethoxy-N-[2-(4-methyl-1,3-oxazol-5-yl)-2-(1,2,3,4-tetrahydroisoquinolin-2-yl)ethyl]benzamide |
| 57 | 2-chloro-4-(5-fluoropyrimidin-2-yl)-N-[2-(4-methyl-1,3-oxazol-5-yl)-2-(1,2,3,4-tetrahydroisoquinolin-2-yl)ethyl]benzamide |
| 58 | 2-chloro-N-[2-(4,4-difluoropiperidin-1-yl)-2-(2,4-dimethyl-1,3-oxazol-5-yl)ethyl]-5-(5-fluoropyrimidin-2-yl)benzamide |
| 59 | N-{2-[4-(benzyloxy)piperidin-1-yl]-2-(4-methyl-1,3-thiazol-5-yl)ethyl}-2-chloro-6-fluorobenzamide |
| 60 | 2-chloro-6-fluoro-N-[2-(4-methyl-1,3-thiazol-5-yl)-2-(4-phenoxypiperidin-1-yl)ethyl]benzamide |
| 61 | 2-chloro-N-[2-(4,4-difluoropiperidin-1-yl)-2-(2-methyl-1,3-thiazol-5-yl)ethyl]-5-(5-fluoropyrimidin-2-yl)benzamide |
| 62 | N-{2-[4-(benzyloxy)piperidin-1-yl]-2-(2-methyl-1,3-thiazol-5-yl)ethyl}-2-chloro-6-fluorobenzamide |
| 63 | N-{2-[4-(benzyloxy)piperidin-1-yl]-2-(1,3-oxazol-5-yl)ethyl}-2-chloro-6-fluorobenzamide |
| 64 | 2-chloro-N-[2-(3,3-difluoropiperidin-1-yl)-2-(4-methyl-1,3-thiazol-5-yl)ethyl]-6-fluorobenzamide |
| 65 | 2-chloro-N-[2-(3,3-difluoroazetidin-1-yl)-2-(4-methyl-1,3-thiazol-5-yl)ethyl]-5-(5-fluoropyrimidin-2-yl)benzamide |
| 66 | 2-chloro-N-[2-(3,3-difluoropiperidin-1-yl)-2-(4-methyl-1,3-thiazol-5-yl)ethyl]-5-(5-fluoropyrimidin-2-yl)benzamide |
| 67 | 2-chloro-N-[2-(4,4-difluoropiperidin-1-yl)-2-[4-(trifluoromethyl)-1,3-thiazol-5-yl]ethyl]-6-fluorobenzamide |
| 68 | 2-chloro-N-[2-(4,4-difluoropiperidin-1-yl)-2-[4-(trifluoromethyl)-1,3-thiazol-5-yl]ethyl]-5-(5-fluoropyrimidin-2- |
| 69 | 2-chloro-N-[2-(4,4-difluoropiperidin-1-yl)-2-[4-methyl($^2$H)-1,3-thiazol-5-yl]ethyl]-5-(5-fluoropyrimidin-2-yl)benzamide |
| 70 | N-[2-(4,4-difluoropiperidin-1-yl)-2-(4-methyl-1,3-thiazol-5-yl)ethyl]-2-fluoro-5-(5-fluoropyrimidin-2-yl)benzamide |
| 71 | N-[2-(4,4-difluoropiperidin-1-yl)-2-(4-methyl-1,3-thiazol-5-yl)ethyl]-5-(5-fluoropyrimidin-2-yl)-2-methoxybenzamide |
| 72 | 2-chloro-N-[2-(4,4-difluoropiperidin-1-yl)-2-(4-methyl-1,3-thiazol-5-yl)ethyl]-5-(pyrazin-2-yl)benzamide |
| 73 | 2-chloro-5-(5-fluoropyrimidin-2-yl)-N-[2-(4-methyl-1,3-thiazol-5-yl)-2-(4-phenoxypiperidin-1-yl)ethyl]benzamide |
| 74 | 2-chloro-N-[2-(4,4-difluoropiperidin-1-yl)-2-(4-methyl-1,3-thiazol-5-yl)ethyl]-5-(6-methylpyridin-2-yl)benzamide |
| 75 | (+)-2-chloro-N-[2-(4,4-difluoropiperidin-1-yl)-2-(4-methyl-1,3-thiazol-5-yl)ethyl]-5-(5-fluoropyrimidin-2-yl)benzamide |
| 76 | (−)-2-chloro-N-[2-(4,4-difluoropiperidin-1-yl)-2-(4-methyl-1,3-thiazol-5-yl)ethyl]-5-(5-fluoropyrimidin-2-yl)benzamide |
| 77 | 2-chloro-N-[2-(4,4-difluoropiperidin-1-yl)-2-(4-methyl-1,3-thiazol-5-yl)ethyl]-5-(5-fluoropyrimidin-2-yl)-N- |
| 78 | 2-chloro-N-[2-(4,4-difluoropiperidin-1-yl)-2-(2-methyl-1,3-thiazol-5-yl)ethyl]-5-(pyrazin-2-yl)benzamide |
| 79 | 2-chloro-N-[2-(4,4-difluoropiperidin-1-yl)-2-(2-methyl-1,3-thiazol-5-yl)ethyl]-5-(6-methylpyridin-2-yl)benzamide |
| 80 | N-[2-(4,4-difluoropiperidin-1-yl)-2-(2-methyl-1,3-thiazol-5-yl)ethyl]-2-fluoro-5-(5-fluoropyrimidin-2-yl)benzamide |
| 81 | 2-chloro-N-[2-(4,4-difluoropiperidin-1-yl)-2-[2-(trifluoromethyl)-1,3-thiazol-5-yl]ethyl]-6-fluorobenzamide |
| 82 | 2-chloro-N-[2-(4,4-difluoropiperidin-1-yl)-2-[2-(trifluoromethyl)-1,3--1,3-thiazol-5-yl]ethyl]-5-(5- |
| 83 | N-[2-(4,4-difluoropiperidin-1-yl)-2-(2-ethyl-1,3-thiazol-5-yl)ethyl]-2-fluoro-6-(5-fluoropyrimidin-2-yl)benzamide |
| 84 | 2-chloro-N-[2-(4,4-difluoropiperidin-1-yl)-2-(2-ethyl-1,3-thiazol-5-yl)ethyl]-6-(5-fluoropyrimidin-2-yl)benzamide |
| 85 | 2-chloro-N-[2-(4,4-difluoropiperidin-1-yl)-2-(2-ethyl-1,3-thiazol-5-yl)ethyl]-6-fluorobenzamide |
| 86 | N-[2-(2-cyclopropyl-1,3-thiazol-5-yl)-2-(4,4-difluoropiperidin-1-yl)ethyl]-2-fluoro-5-(5-fluoropyrimidin-2-yl)benzamide |
| 87 | 2-chloro-N-[2-(2-cyclopropyl-1,3-thiazol-5-yl)-2-(4,4-difluoropiperidin-1-yl)ethyl]-5-(5-fluoropyrimidin-2- |
| 88 | 2-chloro-N-[2-(2-cyclopropyl-1,3-thiazol-5-yl)-2-(4,4-difluoropiperidin-1-yl)ethyl]-6-fluorobenzamide |
| 89 | 2-chloro-4-(5-fluoropyrimidin-2-yl)-N-[2-(2-methyl-1,3-thiazol-5-yl)-2-(1,4-oxazepan-4-yl)ethyl]benzamide |
| 90 | 2-chloro-6-fluoro-N-[2-(4-methyl-1,3-thiazol-5-yl)-2-{2-[2-(trifluoromethyl)phenyl]morpholin-4-yl}ethyl]benzamide |
| 91 | 2-chloro-N-{2-[2-(2,4-difluorophenyl)morpholin-4-yl]-2-(4-methyl-1,3-thiazol-5-yl)ethyl}-6-fluorobenzamide |
| 92 | 2-chloro-6-fluoro-N-[2-(4-methyl-1,3-thiazol-5-yl)-2-[2-(1-methyl-1H-pyrazol-4-yl)morpholin-4-yl]ethyl]benzamide |
| 93 | 2-chloro-5-(5-fluoropyrimidin-2-yl)-N-[2-(4-methyl-1,3-thiazol-5-yl)-2-{5-oxa-8-azaspiro[3.5]nonan-8-yl}ethyl]benzamide |
| 94 | 2-fluoro-5-(5-fluoropyrimidin-2-yl)-N-[2-(4-methyl-1,3-thiazol-5-yl)-2-{5-oxa-8-azaspiro[3.5]nonan-8-yl}ethyl]benzamide |
| 95 | 2-chloro-N-{2-[4-(difluoromethyl)-1,3-thiazol-5-yl]-2-(4,4-difluoropiperidin-1-yl)ethyl}-6-fluorobenzamide |
| 96 | 2-chloro-6-fluoro-N-[2-(4-methyl-1,3-thiazol-5-yl)-2-{5-oxa-8-azaspiro[3.5]nonan-8-yl}ethyl]benzamide |
| 97 | 2-chloro-5-(5-fluoropyrimidin-2-yl)-N-[2-(4-methyl-1,3-thiazol-5-yl)-2-[2-(1-methyl-1H-pyrazol-4-yl)morpholin-4- |
| 98 | 2-fluoro-5-(5-fluoropyrimidin-2-yl)-N-[2-(4-methyl-1,3-thiazol-5-yl)-2-[2-(1-methyl-1H-pyrazol-4-yl)morpholin-4- |
| 99 | N-{2-[2-(2,4-difluorophenyl)morpholin-4-yl]-2-(4-methyl-1,3-thiazol-5-yl)ethyl}quinoline-5-carboxamide |
| 100 | 2-chloro-N-{2-[2-(2,4-difluorophenyl)morpholin-4-yl]-2-(4-methyl-1,3-thiazol-5-yl)ethyl}-6-methylbenzamide |
| 101 | 2-chloro-N-{2-[2-(2,4-difluorophenyl)morpholin-4-yl]-2-(4-methyl-1,3-thiazol-5-yl)ethyl}-6-methylbenzamide |

| Compound | IUPAC NAME |
|---|---|
| 102 | 2-chloro-N-{2-[4-(difluoromethyl)-1,3-thiazol-5-yl]-2-(4,4-difluoropiperidin-1-yl)ethyl}-5-(5-fluoropyrimidin-2-yl)benzamide |
| 103 | 2-chloro-N-[2-(4,4-difluoro-2-methylpiperidin-1-yl)-2-(4-methyl-1,3-thiazol-5-yl)ethyl]-5-(5-fluoropyrimidin-2-yl)benzamide |
| 104 | 2-chloro-N-[2-(4,4-difluoro-2-methylpiperidin-1-yl)-2-(4-methyl-1,3-thiazol-5-yl)ethyl]-6-fluorobenzamide, |
| 105 | N-[2-(2-cyclobutyl-1,3-thiazol-5-yl)-2-(4,4-difluoropiperidin-1-yl)ethyl]quinoline-5-carboxamide |
| 106 | N-[2-(2-cyclobutyl-1,3-thiazol-5-yl)-2-(4,4-difluoropiperidin-1-yl)ethyl]-2-fluoro-5-(5-fluoropyrimidin-2-yl)benzamide |
| 107 | 2-chloro-N-[2-(4,4-difluoropiperidin-1-yl)-2-(2-propyl-1,3-thiazol-5-yl)ethyl]-5-(5-fluoropyrimidin-2-yl)benzamide |
| 108 | N-[2-(4,4-difluoropiperidin-1-yl)-2-(2-propyl-1,3-thiazol-5-yl)ethyl]quinoline-5-carboxamide |
| 109 | 2-chloro-N-[2-(4,4-difluoropiperidin-1-yl)-2-(2-propyl-1,3-thiazol-5-yl)ethyl]-6-fluorobenzamide |
| 110 | 2-chloro-N-[2-(2-cyclobutyl-1,3-thiazol-5-yl)-2-(4,4-difluoropiperidin-1-yl)ethyl]-6-fluorobenzamide |
| 111 | 2-chloro-N-[2-(2-cyclobutyl-1,3-thiazol-5-yl)-2-(4,4-difluoropiperidin-1-yl)ethyl]-5-(5-fluoropyrimidin-2- |
| 112 | 2-chloro-N-[2-(4,4-difluoropiperidin-1-yl)-2-[2-(hydroxymethyl)-1,3-thiazol-5-yl]ethyl]-5-(5-fluoropyrimidin-2- |
| 113 | 2-chloro-N-[2-(4,4-difluoro-2-methylpiperidin-1-yl)-2-(2-methyl-1,3-thiazol-5-yl)ethyl]-5-(5-fluoropyrimidin-2-yl) |
| 114 | 2-chloro-N-[2-(4,4-difluoropiperidin-1-yl)-2-(4-methyl-1,3-thiazol-5-yl)ethyl]-4-(1,1-dioxo-1$\square^6$,2-thiazolidin-2- |
| 115 | N-{2-[2-(4,4-difluorocyclohexyl)-1,3-thiazol-5-yl]-2-(morpholin-4-yl)ethyl}quinoline-6-carboxamide |
| 116 | 2-chloro-N-{2-[2-(4,4-difluorocyclohexyl)-1,3-thiazol-5-yl]-2-(morpholin-4-yl)ethyl}-6-fluorobenzamide |
| 117 | 2-chloro-N-{2-[2-(4,4-difluorocyclohexyl)-1,3-thiazol-5-yl]-2-(4,4-difluoropiperidin-1-yl)ethyl}-6-fluorobenzamide |
| 118 | N-[2-(2-tert-butyl-1,3-thiazol-5-yl)-2-(4,4-difluoropiperidin-1-yl)ethyl]-2-chloro-6-fluoro-benzamide |
| 119 | 2-chloro-N-[2-(4-cyclopropyl-1,3-thiazol-5-yl)-2-(4,4-difluoropiperidin-1-yl)ethyl]-5-(5-fluoropyrimidin-2- |
| 120 | N-[2-(4,4-difluoropiperidin-1-yl)-2-(4-methyl-1,3-thiazol-5-yl)ethyl]-7-fluoro-2-oxo-1,2,3,4-tetrahydroquinoline-6- |
| 121 | N-[2-(4-cyclopropyl-1,3-thiazol-5-yl)-2-(4,4-difluoropiperidin-1-yl)ethyl]quinoline-5-carboxamide |
| 122 | N-[2-(2-tert-butyl-1,3-thiazol-5-yl)-2-(4,4-difluoropiperidin-1-yl)ethyl]-2-chloro-5-(5-fluoropyrimidin-2-yl)benzamide |
| 123 | 2-chloro-N-[2-(4-cyclopropyl-1,3-thiazol-5-yl)-2-(4,4-difluoropiperidin-1-yl)ethyl]-6-fluorobenzamide |
| 124 | N-[2-(2-tert-butyl-1,3-thiazol-5-yl)-2-(4,4-difluoropiperidin-1-yl)ethyl]quinoline-5-carboxamide |
| 125 | 2-chloro-N-{2-[2-(4,4-difluorocyclohexyl)-1,3-thiazol-5-yl]-2-(morpholin-4-yl)ethyl}-5-(5-fluoropyrimidin-2-yl)benzamide |
| 126 | 2-chloro-N-{2-[2-(4,4-difluorocyclohexyl)-1,3-thiazol-5-yl]-2-(4,4-difluoropiperidin-1-yl)ethyl}-5-(5-fluoropyrimidin-2- |
| 127 | (+)-2-chloro-N-[2-(4,4-difluoro-piperidin-1-yl)-2-(2-methylthiazol-5-yl)ethyl]-5-(5-fluoropyrimidin-2-yl)benzamide |
| 128 | (−)-2-chloro-N-[2-(4,4-difluoro-piperidin-1-yl)-2-(2-methylthiazol-5-yl)ethyl]-5-(5-fluoropyrimidin-2-yl)benzamide |
| 129 | 2-chloro-N-{2-[4-(difluoromethyl)-1,3-thiazol-5-yl]-2-(morpholin-4-yl)ethyl}-5-(5-fluoropyrimidin-2-yl)benzamide |
| 130 | 2-chloro-N-{2-[4-(difluoromethyl)-1,3-thiazol-5-yl]-2-(morpholin-4-yl)ethyl}-6-fluorobenzamide. |

8. A pharmaceutical composition comprising a compound of Formula (I) according to claim 1 and a pharmaceutically acceptable diluent and/or carrier.

\* \* \* \* \*